United States Patent
Park et al.

(10) Patent No.: US 11,045,228 B2
(45) Date of Patent: Jun. 29, 2021

(54) PREOPERATIVELY PLANNING AN ARTHROPLASTY PROCEDURE AND GENERATING A CORRESPONDING PATIENT SPECIFIC ARTHROPLASTY RESECTION GUIDE

(71) Applicant: Howmedica Osteonics Corporation, Mahwah, NJ (US)

(72) Inventors: Ilwhan Park, Walnut Creek, CA (US); Keun Song, Palo Alto, CA (US); Oleg Mishin, Foster City, CA (US); Michael Santarella, Essex Fells, NJ (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

(21) Appl. No.: 16/923,548

(22) Filed: Jul. 8, 2020

(65) Prior Publication Data
US 2020/0337734 A1  Oct. 29, 2020

Related U.S. Application Data

(60) Continuation of application No. 16/803,664, filed on Feb. 27, 2020, which is a continuation of application
(Continued)

(51) Int. Cl.
*A61B 17/70* (2006.01)
*A61B 34/10* (2016.01)
(Continued)

(52) U.S. Cl.
CPC .......... *A61B 17/7013* (2013.01); *A61B 5/055* (2013.01); *A61B 6/032* (2013.01); *A61B 17/1675* (2013.01); *A61B 17/1703* (2013.01); *A61B 34/10* (2016.02); *A61B 90/37* (2016.02);

*B33Y 10/00* (2014.12); *B33Y 50/00* (2014.12); *B33Y 50/02* (2014.12); *B33Y 80/00* (2014.12); *G06F 30/00* (2020.01); *G06F 30/20* (2020.01); *G06K 9/2063* (2013.01); *G06K 9/48* (2013.01); *G06T 7/0012* (2013.01); *G06T 7/12* (2017.01); *G06T 7/13* (2017.01); *G06T 17/00* (2013.01); *G06T 17/20* (2013.01); *G16H 50/50* (2018.01);
(Continued)

(58) Field of Classification Search
USPC ........................................................ 703/11
See application file for complete search history.

(56) References Cited

U.S. PATENT DOCUMENTS

| 2011/0092804 A1* | 4/2011 | Schoenefeld | A61B 17/151 600/416 |
| 2020/0261119 A1* | 8/2020 | Pavlovskaia | G06T 17/20 |

* cited by examiner

*Primary Examiner* — Rodney E Fuller
(74) *Attorney, Agent, or Firm* — Polsinelli PC

(57) ABSTRACT

Methods of manufacturing a custom arthroplasty resection guide or jig are disclosed herein. For example, one method may include: generating MRI knee coil two dimensional images, wherein the knee coil images include a knee region of a patient; generating MRI body coil two dimensional images, wherein the body cod images include a hip region of the patient, the knee region of the patient and an ankle region of the patient; in the knee coil images, identifying first locations of knee landmarks; in the body coil images, identifying second locations of the knee landmarks; run a transformation with the first and second locations, causing the knee coil images and body coil images to generally correspond with each other with respect to location and orientation.

20 Claims, 38 Drawing Sheets

Related U.S. Application Data

No. 16/522,281, filed on Jul. 25, 2019, now Pat. No. 10,575,875, which is a continuation-in-part of application No. 16/229,997, filed on Dec. 21, 2018, now Pat. No. 10,675,063, which is a continuation of application No. 15/581,974, filed on Apr. 8, 2017, now Pat. No. 10,159,513, which is a continuation of application No. 14/946,106, filed on Nov. 19, 2015, now Pat. No. 9,687,259, which is a continuation of application No. 13/731,697, filed on Dec. 31, 2012, now Pat. No. 9,208,263, which is a continuation of application No. 13/374,960, filed on Jan. 25, 2012, now Pat. No. 8,532,361, which is a continuation of application No. 13/066,568, filed on Apr. 18, 2011, now Pat. No. 8,160,345, which is a continuation-in-part of application No. 12/386,105, filed on Apr. 14, 2009, now Pat. No. 8,311,306, said application No. 16/522,281 is a continuation-in-part of application No. 16/017,320, filed on Jun. 25, 2018, now Pat. No. 10,617,475, which is a continuation of application No. 15/802,137, filed on Nov. 2, 2017, now Pat. No. 10,034,714, which is a continuation of application No. 15/469,171, filed on Mar. 24, 2017, now Pat. No. 9,839,485, which is a continuation of application No. 15/242,312, filed on Aug. 19, 2016, now Pat. No. 9,636,120, which is a division of application No. 14/476,500, filed on Sep. 3, 2014, now Pat. No. 9,451,970, which is a continuation of application No. 13/731,850, filed on Dec. 31, 2012, now Pat. No. 8,961,527, which is a continuation of application No. 12/505,056, filed on Jul. 17, 2009, now Pat. No. 8,777,875, said application No. 16/522,281 is a continuation-in-part of application No. 16/211,735, filed on Dec. 6, 2018, which is a continuation of application No. 15/167,710, filed on May 27, 2016, now Pat. No. 10,182,870, which is a continuation-in-part of application No. 14/084,255, filed on Nov. 19, 2013, now Pat. No. 9,782,226, which is a continuation of application No. 13/086,275, filed on Apr. 13, 2011, now Pat. No. 8,617,171, which is a continuation-in-part of application No. 12/760,388, filed on Apr. 14, 2010, now Pat. No. 8,737,700, which is a continuation-in-part of application No. 12/563,809, filed on Sep. 21, 2009, now Pat. No. 8,545,509, and a continuation-in-part of application No. 12/546,545, filed on Aug. 24, 2009, now Pat. No. 8,715,291, said application No. 12/563,809 is a continuation-in-part of application No. 12/111,924, filed on Apr. 29, 2008, now Pat. No. 8,480,679, said application No. 12/546,545 is a continuation-in-part of application No. 11/959,344, filed on Dec. 18, 2007, now Pat. No. 8,221,430, said application No. 12/563,809 is a continuation-in-part of application No. 12/505,056, filed on Jul. 17, 2009, now Pat. No. 8,777,875, and a continuation-in-part of application No. 11/959,344, filed on Dec. 18, 2007, now Pat. No. 8,221,430, said application No. 12/760,388 is a continuation-in-part of application No. 11/959,344, filed on Dec. 18, 2007, now Pat. No. 8,221,430, and a continuation-in-part of application No. 12/111,924, filed on Apr. 29, 2008, now Pat. No. 8,480,679, and a continuation-in-part of application No. 12/505,056, filed on Jul. 17, 2009, now Pat. No. 8,777,875.

(60) Provisional application No. 61/126,102, filed on Apr. 30, 2008, provisional application No. 61/083,053, filed on Jul. 23, 2008, provisional application No. 61/102,692, filed on Oct. 3, 2008.

(51) Int. Cl.

| | | |
|---|---|---|
| *A61B 6/03* | (2006.01) | |
| *A61B 5/055* | (2006.01) | |
| *G06T 7/13* | (2017.01) | |
| *G06T 7/12* | (2017.01) | |
| *G16H 50/50* | (2018.01) | |
| *G06T 7/00* | (2017.01) | |
| *B33Y 50/02* | (2015.01) | |
| *B33Y 10/00* | (2015.01) | |
| *G06T 17/20* | (2006.01) | |
| *G06K 9/20* | (2006.01) | |
| *A61B 17/17* | (2006.01) | |
| *A61B 17/16* | (2006.01) | |
| *G06T 17/00* | (2006.01) | |
| *G06K 9/48* | (2006.01) | |
| *B33Y 80/00* | (2015.01) | |
| *B33Y 50/00* | (2015.01) | |
| *A61B 90/00* | (2016.01) | |
| *G06F 30/00* | (2020.01) | |
| *G06F 30/20* | (2020.01) | |
| *G06T 7/70* | (2017.01) | |
| *A61B 17/15* | (2006.01) | |

(52) U.S. Cl.
CPC ........... *A61B 17/155* (2013.01); *A61B 17/157* (2013.01); *A61B 2017/1602* (2013.01); *A61B 2034/105* (2016.02); *A61B 2034/107* (2016.02); *A61B 2034/108* (2016.02); *A61B 2090/374* (2016.02); *A61B 2090/3762* (2016.02); *G06K 2009/484* (2013.01); *G06K 2209/055* (2013.01); *G06T 7/70* (2017.01); *G06T 2200/08* (2013.01); *G06T 2207/30008* (2013.01); *Y10T 29/49826* (2015.01)

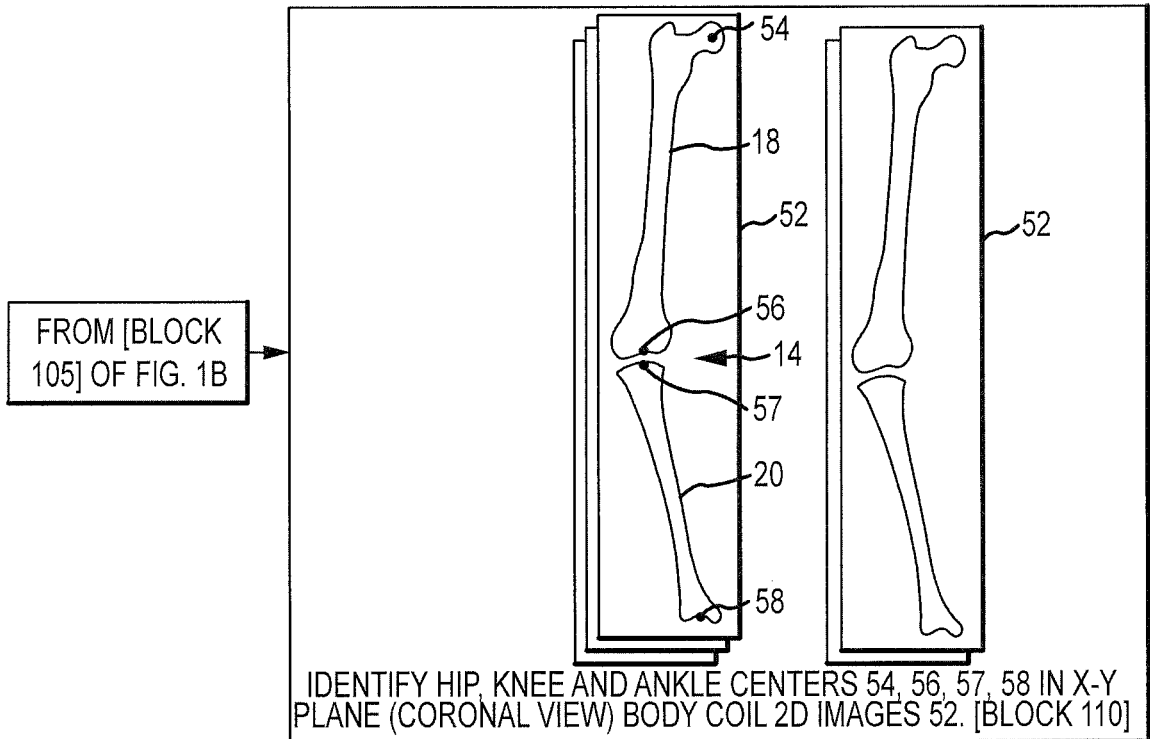

IDENTIFY HIP, KNEE AND ANKLE CENTERS 54, 56, 57, 58 IN X-Y PLANE (CORONAL VIEW) BODY COIL 2D IMAGES 52. [BLOCK 110]

| TABLE A | X GLOBAL COORDINATE LOCATION | Y GLOBAL COORDINATE LOCATION | Z GLOBAL COORDINATE LOCATION |
|---|---|---|---|
| FEMUR HIP CENTER 54 | $X_{54}$ | $Y_{54}$ | $Z_{54}$ |
| FEMUR KNEE CENTER 56 | $X_{56}$ | $Y_{56}$ | $Z_{56}$ |
| TIBIA KNEE CENTER 57 | $X_{57}$ | $Y_{57}$ | $Z_{57}$ |
| TIBIA ANKLE CENTER 58 | $X_{58}$ | $Y_{58}$ | $Z_{58}$ |

STORE LOCATIONS OF HIP, KNEE AND ANKLE CENTERS 54, 56, 57, 58 IN TABLE. [BLOCK 115]

FROM [BLOCK 105] OF FIG. 1B

FROM [BLOCK 175] OF FIG. 1G

TO GENERALLY MAINTAIN THE LOCATION AND ORIENTATION RELATIONSHIPS BETWEEN THE HIP, KNEE AND ANKLE CENTERS 54, 56, 57, 58 AND THE KNEE COIL 2D IMAGES 16 AND THE DESCENDANT 3D BONE MODELS 22, 28 OF THE KNEE COIL 2D IMAGES 16, SUCH LOCATION AND ORIENTATION RELATIONSHIPS BEING ESTABLISHED IN [BLOCK 135], ADJUST X, Y AND Z GLOBAL COORDINATE LOCATIONS AND/OR ORIENTATIONS OF EACH OF THE CENTER POINTS 54, 56, 57, 58 IN "TABLE A" OF [BLOCK 115] FOR ANY 3D LOCATION AND/OR ORIENTATION IMPACT ON THE CENTER POINTS 54, 56, 57, 58 ON ACCOUNT OF ANY OF THE PROCESSES OF [BLOCKS 160, 165 & 170] OR ANY OTHER LOCATION AND/OR ORIENTATION CHANGE TO THE 3D BONE MODELS 22 OR RESTORED BONE MODELS 28. [BLOCK 120]

TO [BLOCK 190] OF FIG. 1H

FIG. 1C

PREOPERATIVELY PLANNING AN ARTHROPLASTY PROCEDURE AND GENERATING A CORRESPONDING PATIENT SPECIFIC ARTHROPLASTY RESECTION GUIDE

CROSS REFERENCE TO RELATED APPLICATIONS

The present application is a continuation application of U.S. patent application Ser. No. 16/803,664, filed Feb. 27, 2020, which application is a continuation of U.S. patent application Ser. No. 16/522,281, filed Jul. 25, 2019, now U.S. Pat. No. 10,575,875, which application is a continuation-in-part application of U.S. patent application Ser. No. 16/229,997, filed Dec. 21, 2018, now U.S. Pat. No. 10,675,063, which is a continuation application of U.S. application Ser. No. 15/581,974 filed Apr. 28, 2017, now U.S. Pat. No. 10,159,513, which application is a continuation of U.S. application Ser. No. 14/946,106 filed Nov. 19, 2015, now U.S. Pat. No. 9,687,259, which application is a continuation of U.S. application Ser. No. 13/731,697 filed Dec. 31, 2012, now U.S. Pat. No. 9,208,263, which application is a continuation of U.S. application Ser. No. 13/374,960 filed Jan. 25, 2012, now U.S. Pat. No. 8,532,361, which application is a continuation of U.S. patent application Ser. No. 13/066,568, filed Apr. 18, 2011, now U.S. Pat. No. 8,160,345, which application is a continuation-in-part application of U.S. patent application Ser. No. 12/386,105 filed Apr. 14, 2009, now U.S. Pat. No. 8,311,306. U.S. application Ser. No. 12/386,105 claims the benefit under 35 U.S.C. § 119(e) of U.S. Provisional Patent Application No. 61/126,102, entitled "System and Method For Image Segmentation in Generating Computer Models of a Joint to Undergo Arthroplasty" filed on Apr. 30, 2008.

U.S. patent application Ser. No. 16/522,281, filed Jul. 25, 2019, is also a continuation-in-part of U.S. patent application Ser. No. 16/017,320, filed Jun. 25, 2018, now U.S. Pat. No. 10,617,475, which is a continuation application of U.S. patent application Ser. No. 15/802,137, filed Nov. 2, 2017, now U.S. Pat. No. 10,034,714, which is a continuation application of U.S. patent application Ser. No. 15/469,171, filed Mar. 24, 2017, now U.S. Pat. No. 9,839,485, which is a continuation application of U.S. patent application Ser. No. 15/242,312, filed Aug. 19, 2016, now U.S. Pat. No. 9,636,120, which is a divisional application of U.S. patent application Ser. No. 14/476,500, filed Sep. 3, 2014, now U.S. Pat. No. 9,451,970, which is a continuation application of U.S. patent application Ser. No. 13/731,850, filed Dec. 31, 2012, now U.S. Pat. No. 8,961,527, which is a continuation application of U.S. patent application Ser. No. 12/505,056, filed Jul. 17, 2009, now U.S. Pat. No. 8,777,875, which claims priority under 35 U.S.C. § 119(e) of U.S. Provisional Patent Application No. 61/081,053, filed Jul. 23, 2008.

U.S. patent application Ser. No. 16/522,281, filed Jul. 25, 2019, is also a continuation-in-part of U.S. patent application Ser. No. 16/211,735, filed Dec. 6, 2018, which is a continuation of U.S. application Ser. No. 15/167,710 filed May 27, 2016, now U.S. Pat. No. 10,182,870, which application is a continuation-in-part of U.S. application Ser. No. 14/084,255 filed Nov. 19, 2013, now U.S. Pat. No. 9,782,226, which application is a continuation of U.S. application Ser. No. 13/086,275 ("the '275 application"), filed Apr. 13, 2011, and titled "Preoperatively Planning an Arthroplasty Procedure and Generating a Corresponding Patient Specific Arthroplasty Resection Guide," now U.S. Pat. No. 8,617,171. The '275 application is a continuation-in-part ("CIP") of U.S. patent application Ser. No. 12/760,388 ("the '388 application"), filed Apr. 14, 2010, now U.S. Pat. No. 8,737,700. The '388 application is a CIP application of U.S. patent application Ser. No. 12/563,809 ("the '809 application), filed Sep. 21, 2009, and titled "Arthroplasty System and Related Methods," now U.S. Pat. No. 8,545,509, which claims priority to U.S. patent application 61/102,692 ("the '692 application"), filed Oct. 3, 2008, and titled "Arthroplasty System and Related Methods." The '388 application is also a CIP application of U.S. patent application Ser. No. 12/546,545 ("the 545 application"), filed Aug. 24, 2009, and titled "Arthroplasty System and Related Methods," now U.S. Pat. No. 8,715,291, which claims priority to the '692 application. The '809 application is also a CIP application of U.S. patent application Ser. No. 12/111,924 ("the '924 application"), filed Apr. 29, 2008, and titled "Generation of a Computerized Bone Model Representative of a Pre-Degenerated State and Useable in the Design and Manufacture of Arthroplasty Devices," now U.S. Pat. No. 8,480,679. The '545 application is also a CIP application of U.S. patent application Ser. No. 11/959,344 ("the '344 application), filed Dec. 18, 2007, and titled "System and Method for Manufacturing Arthroplasty Jigs," now U.S. Pat. No. 8,221,430. The '809 application is a DIP application of U.S. patent application Ser. No. 12/505,056 ("the '056 application"), filed Jul. 17, 2009, and titled "System and Method for Manufacturing Arthroplasty Jigs Having improved Mating Accuracy," now U.S. Pat. No. 8,777,875. The '056 application claims priority to U.S. patent application 61/083,053, filed Jul. 23, 2008, and titled "System and Method for Manufacturing Arthroplasty Jigs Having Improved Mating Accuracy." The '809 application is also a CIP application of the '344 application. The '388 application is also a CIP of the '344 application. The '388 application is also a CIP of the '924 application. And the '388 application is also a CIP of the '056 application.

The present application claims priority to all of the above mentioned applications and hereby incorporates by reference all of the above-mentioned applications in their entireties into the present application.

FIELD OF THE INVENTION

The present invention relates to systems and methods for manufacturing customized arthroplasty cutting jigs. More specifically, the present invention relates to automated systems and methods of manufacturing such jigs.

BACKGROUND OF THE INVENTION

Over time and through repeated use, bones and joints can become damaged or worn. For example, repetitive strain on bones and joints (e g, through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in Unbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state.

It is believed that it is best for the vast majority of patients to have the patient's joint restored to its pre-deteriorated state (i.e., natural (i.e., kinematic) alignment). However, for some patient's, it may not be possible or desirable to restore the patient's joint to it natural (i.e., kinematic) alignment. For example, a physician may determine that the patient's joint assume a zero degree mechanical axis alignment or an alignment between the zero degree mechanical axis alignment and the natural (i.e., kinematic) alignment.

There is a need in the art for a system and method capable of generating customized arthroplasty jigs configured for a variety of alignment results. There is also a need in the art for a system and method capable of communicating joint alignment information to a physician and incorporating into the jig design the physician's input regarding the alignment information.

SUMMARY

Various embodiments of a method of manufacturing a custom arthroplasty resection guide or jig are disclosed herein. In a first embodiment, the method may include: generate MRI knee coil two dimensional images, wherein the knee coil images include a knee region of a patient; generate MRI body coil two dimensional images, wherein the body coil images include a hip region of the patient, the knee region of the patient and an ankle region of the patient; in the knee coil images, identify first locations of knee landmarks; in the body coil images, identify second locations of the knee landmarks; run a transformation with the first and second locations, causing the knee coil images and body coil images to generally correspond with each other with respect to location and orientation.

In a second embodiment, the method may include: preoperatively plan in a three dimensional computer environment a proposed post-surgical joint geometry for a joint, wherein the proposed post-surgical joint geometry is a natural (i.e., kinematic) alignment joint geometry that is generally representative of the joint prior to degeneration; provide a two dimensional coronal view of the proposed post-surgical joint geometry to a physician; employ feedback received from the physician regarding the two dimensional coronal view to arrive at a finalized post-surgical joint geometry that is at least one of: a) the natural alignment joint geometry; b) a zero degree mechanical axis alignment joint geometry, or somewhere between a) and b).

In a third embodiment, the method may include: a) identify in a computer environment hip, knee and ankle centers in a first set of two dimensional images; b) generate in a computer environment a three dimensional knee model from a second set of two dimensional images; c) cause the three dimensional knee model and hip, knee and ankle centers to be positioned relative to each other in a global coordinate system generally as if the three dimensional knee model were generated from the first set of two dimensional images; d) preoperatively plan an arthroplasty procedure with the three dimensional knee model of step c); and e) at least one of maintain or reestablish the positional relationship established in step c) between the three dimensional knee model and the hip, knee and ankle centers to address any positional changes in the global coordinate system for the three dimensional knee model during the preoperatively planning of step d).

In a fourth embodiment, the method may include: a) generating a three dimensional femur bone model from MRI knee coil two dimensional images, wherein the knee coil images include a knee region of a patient; b) identifying a hip center and a femur knee center in MRI body coil two dimensional images, wherein the body coil images include a hip region of the patient and the knee region of the patient; c) causing the three dimensional femur bone model and hip center and femur knee center to generally correspond with each other with respect to location and orientation; d) defining relative to the three dimensional femur bone model a femoral mechanical axis via the femur knee center and the hip center; e) identifying a most distal condylar point of the three dimensional femur bone model; f) defining a distal plane that is orthogonal to the femoral mechanical axis in a coronal view of the three dimensional femur bone model, wherein the distal plane also passes through the most distal condylar point; g) and defining a resection plane that is parallel to the distal plane and proximally offset from the distal plane; and h) using data associated with the resection plane to define a resection guide in the custom arthroplasty resection guide.

In a fifth embodiment, the method may include: a) generating a three dimensional tibia bone model from MRI knee coil two dimensional images, wherein the knee coil images include a knee region of a patient; b) identifying an ankle center and a tibia knee center in MRI body coil two dimensional images, wherein the body coil images include an ankle region of the patient and the knee region of the patient; c) causing the three dimensional tibia bone model and ankle center and tibia knee center to generally correspond with each other with respect to location and orientation; d) defining relative to the three dimensional tibia bone model a tibial mechanical axis via the tibia knee center and the ankle center; e) identifying a condylar point of the three dimensional tibia bone model; f) defining a proximal plane that is orthogonal to the tibial mechanical axis in a coronal view a the three dimensional tibia bone model, wherein the proximal plane also passes through a condylar point; g) defining a resection plane that is parallel to the proximal plane and distally offset from the proximal plane; and h) using data associated with the resection plane to define a resection guide in the custom arthroplasty resection guide.

In a sixth embodiment, the method may include: a) identify in a computer environment hip, knee and ankle centers in a first set of two dimensional images; b) generate in a computer environment a three dimensional knee model from a second set of two dimensional images; c) cause the three dimensional knee model and hip, knee and ankle centers to be positioned relative to each other in a global coordinate system generally as if the three dimensional knee model were generated from the first set of two dimensional images; d) preoperatively plan an arthroplasty procedure with the three dimensional knee model of step c) via a method including: i) defining a mechanical axis relative to the three dimensional knee model via a pair of points including the knee center and at least one of the hip center or ankle center; and ii) defining a resection plane parallel to, and offset from, a reference plane that: 1) is orthogonal to the mechanical axis in a coronal view and 2) extends through a condylar point on the three dimensional knee model; and e) using data associated with the resection plane to define a resection guide in the custom arthroplasty resection guide.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1K are flow chart diagrams outlining the jig production method disclosed herein.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

The methods and systems disclosed herein allow a resulting jig 2 to generate surgical resections that allow implanted arthroplasty prosthetic femoral and tibial joint components to achieve a joint alignment that is: (1) generally representative of the patient's pre-degenerative joint line; generally corresponding to a zero mechanical axis alignment; or (3) somewhere between (1) and (2). Whether the resections result in a joint alignment that is (1), (2) or somewhere between (1) and (2) may be a result of an input and modification of the natural (i.e., kinematic) joint alignment calculated during preoperative planning ("POP").

Figure 4:
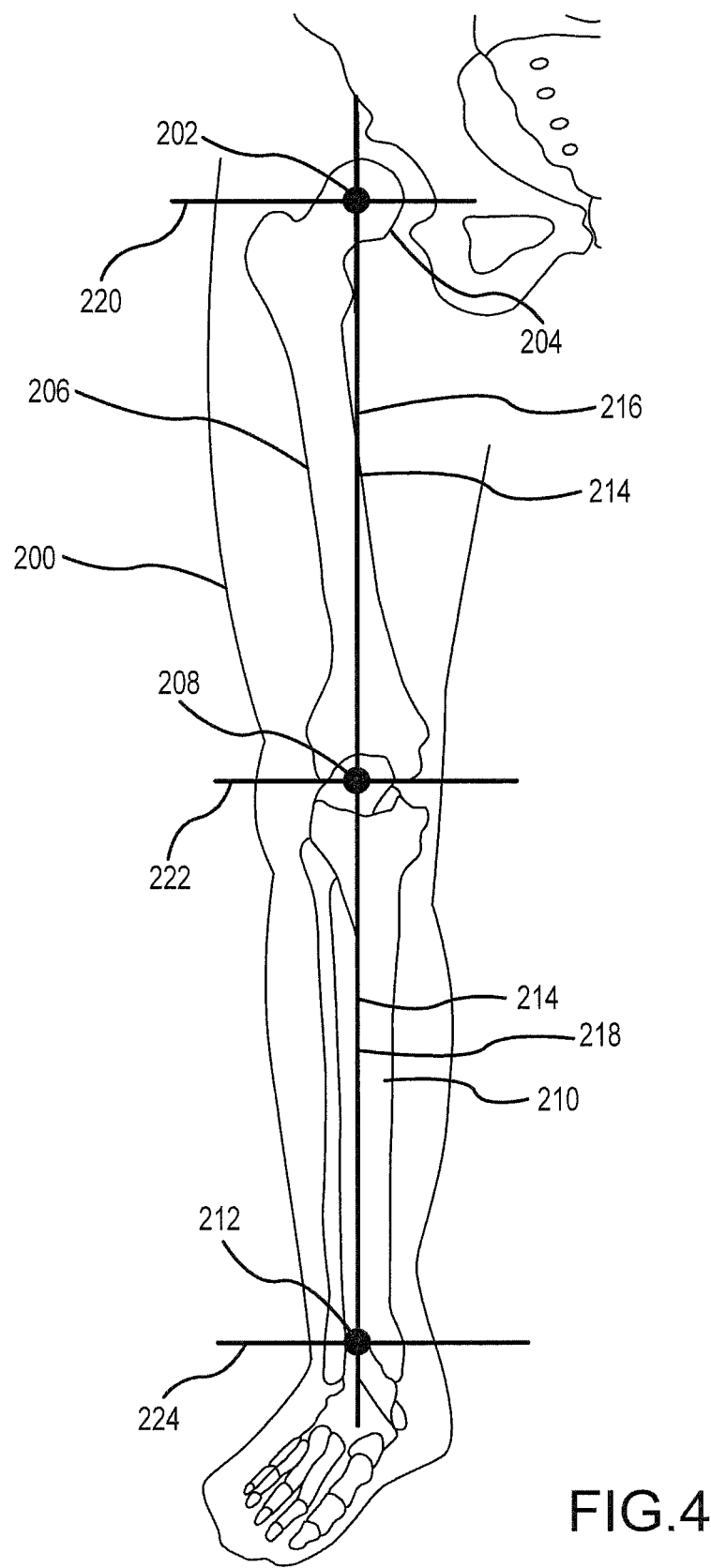
FIG. 4 is a coronal view of a patient's leg having a zero-degree mechanical axis knee joint geometry.

As can be understood from FIG. 4, which is a coronal view of a patient's leg 200, in zero-degree mechanical axis theory, the center of the hip 202 (located at the head 204 of the femur 206), the center of the knee 208 (located at the notch where the intercondylar tubercle of the tibia 210 meets the femur 206), and the center of ankle 212 form a straight line which defines the mechanical axis ("MA") 214 of the leg skeletal structure. As a result, the femoral mechanical axis ("FMA") 216, which extends from the hip center 202 to the knee center 208, is coextensively aligned with the MA 214. Similarly, the tibial mechanical axis (TMA") 218, which extends from the knee center 208 to the ankle center 212, is coextensively aligned with the MA 214. When the patient's leg 200 is standing in full extension and viewed from the front, the MA 214, MIA 216 and TMA 218 are perpendicular to the hip center axis 220, the knee joint line axis 222, and the ankle center axis 224.

Figure 5:
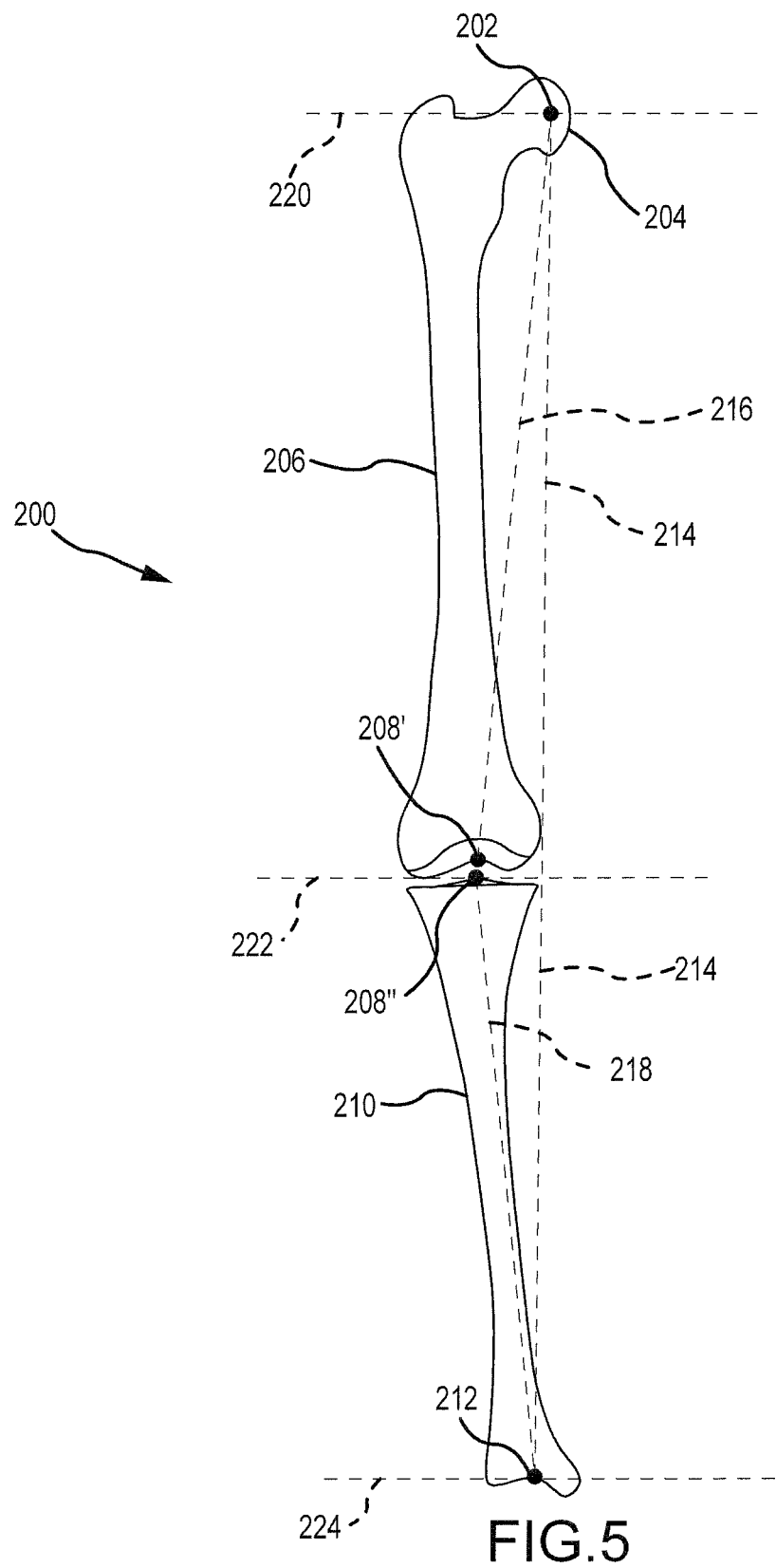
FIG. 5 is a coronal view of a patient's leg having a varus knee joint geometry.

In reality, only approximately two percent of the human population has the zero-degree mechanical axis ("neutral") leg skeletal structure depicted in FIG. 4. The other approximately 98 percent of the human population has a leg skeletal structure that is slightly varus (bow legged), as depicted in FIG. 5, or slightly valgus (knocked knee). Thus, for such varus or valgus leg skeletal structures, the FMA 214 and TMA 216 will not be coextensively aligned with the MA 214 or perpendicular to the knee joint line axis 222.

A knee arthroplasty procedure may be considered a natural alignment or kinematic alignment procedure when the knee arthroplasty procedure is preoperatively planned such that the prosthetic knee implants implanted during the knee arthroplasty procedure generally return the patient's knee geometry to the geometry that existed before the patient's knee geometry was impacted via deterioration of the knee joint. For example, if the patient's pre-deteriorated knee geometry was varus, such as depicted in FIG. 5, then the knee arthroplasty procedure is preoperatively planned such that the implanted prosthetic knee implants result in a knee geometry that is generally the same extent varus. Similarly, if the patient's pre-deteriorated knee geometry was valgus, then the knee arthroplasty procedure is preoperatively planned such that the implanted prosthetic knee implants result in a knee geometry that is generally the same extent valgus. Finally, if the patient's pre-deteriorated knee geometry was neutral, such as depicted in FIG. 4, then the knee arthroplasty procedure is preoperatively planned such that the implanted prosthetic knee implants result in a knee geometry that is generally neutral.

In natural or kinematic alignment, the goal may be to create a prosthetic knee joint line 222 that recreates the patient's pre-degenerated knee joint line 222, which may have been parallel to the ground during a two legged stance in the frontal plane (feet approximated and parallel to the ground during gait). Studies suggest that with the feet approximated in two-legged stance, the joint line is parallel to the ground, and the mechanical axis is positioned with a two to three degree inward inclination.

A knee arthroplasty procedure may be considered a zero-degree mechanical axis or neutral alignment procedure when the knee arthroplasty procedure is preoperatively planned such that the prosthetic knee implants implanted during the knee arthroplasty procedure generally result in a neutral knee geometry for the patient, regardless of whether the patient's pre-deteriorated knee geometry was varus, valgus or neutral. In zero-degree mechanical axis alignment, the goal may be to create a prosthetic knee joint line 222 that is perpendicular to the TMA 218, the TMA 218 coinciding with the MA 214.

A patient's natural pre-degenerated knee geometry may have served the patient well prior to knee joint degeneration. However, a physician may determine that it is in the patient's best interest to receive a post-surgical knee geometry that is a natural alignment, neutral alignment, or something in between, depending on the physician's assessment of the patient's deteriorated bone geometry and condition, the applicability of available prosthetic implants, and other factors. Consequently, there is a need for the systems and methods disclosed herein.

Figure 1A:
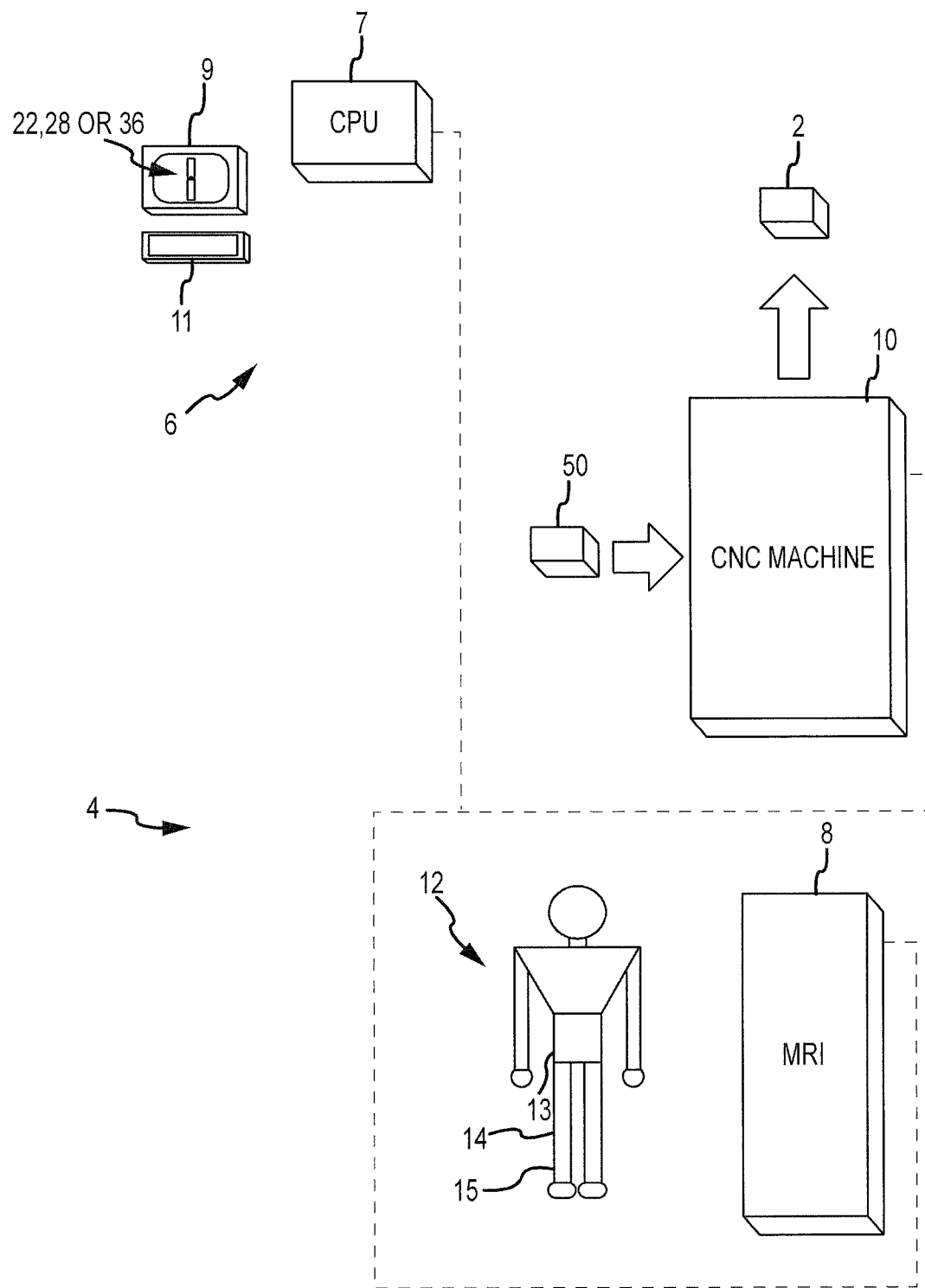
FIG. 1A is a schematic diagram of a system for employing the automated jig production method disclosed herein.

To provide an overall understanding of the systems 4 for, and methods of, producing the customized arthroplasty jigs 2, reference is made to FIGS. 1A-1K. FIG. 1A is a schematic diagram of a system 4 for employing the automated jig production method disclosed herein. FIGS. 1B-1K are flow chart diagrams outlining the jig production method disclosed herein. The systems 4 for, and methods of, producing the customized arthroplasty jigs 2 can be broken into six sections.

The first section, which is discussed with respect to FIG. 1A and [Blocks 100-115 and 125-135] of FIGS. 1B-1E, pertains to example methods of generating two-dimensional ("2D") body coil MRI images 52 and 2D knee coil MRI images 16, identifying hip, knee and ankle center points 54, 56, 57, 58 in the 2D body coil MRI images 52, and matching the 2D knee coil MRI images 16 to the 2D body coil MRI images 52 with respect to location and orientation in a global coordinate system 63.

Figure 1B:
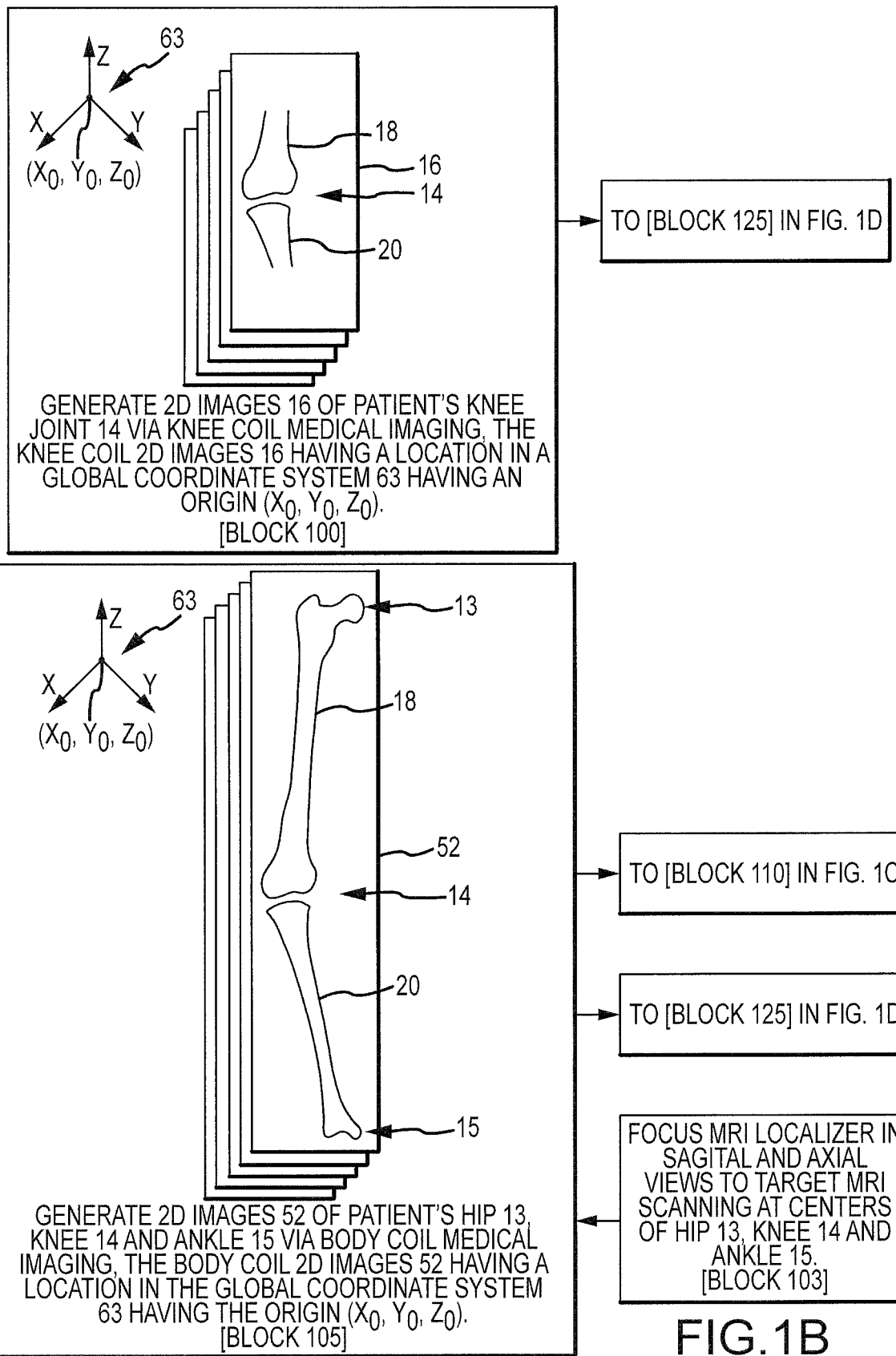
Figure 1D:
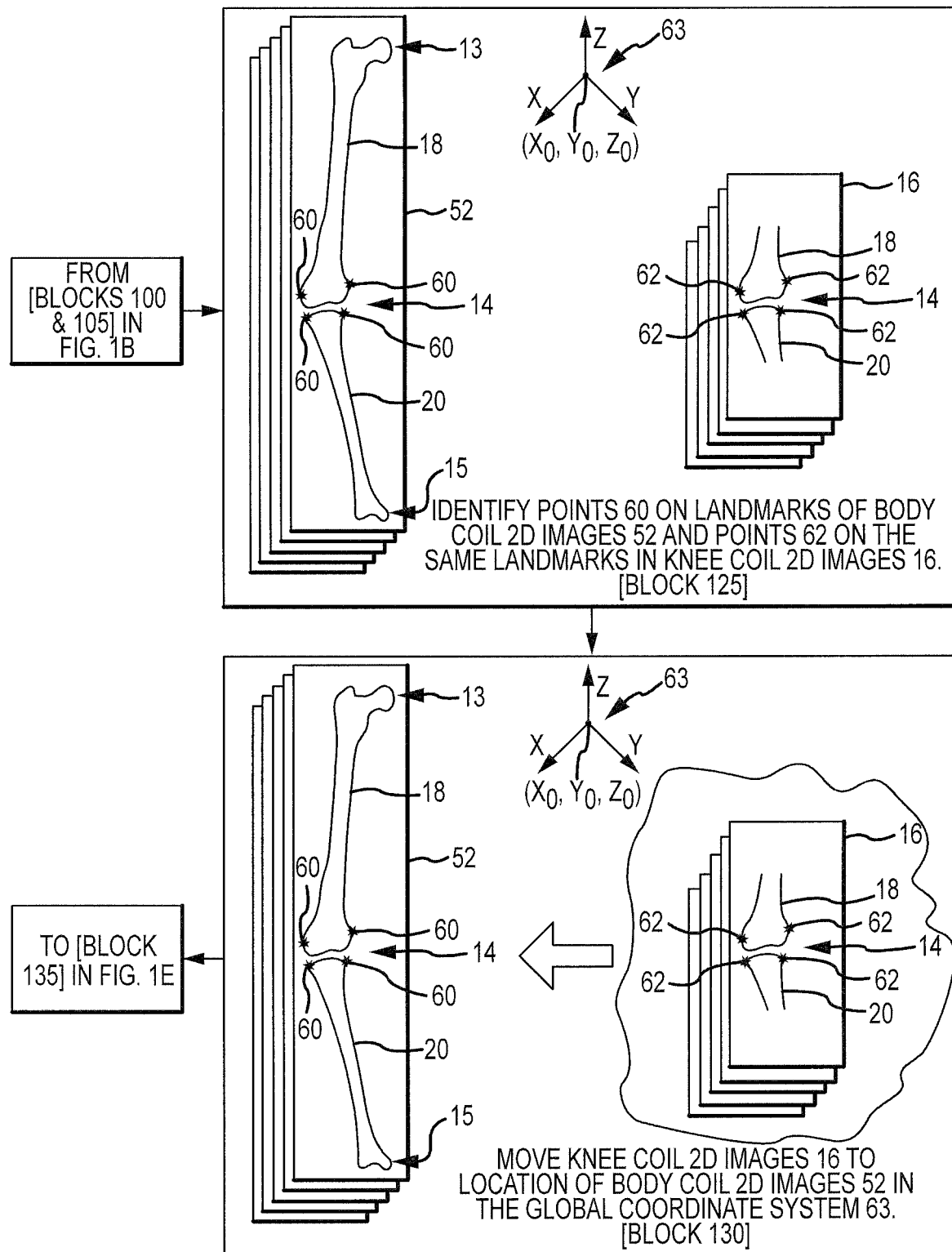
Figure 1E:
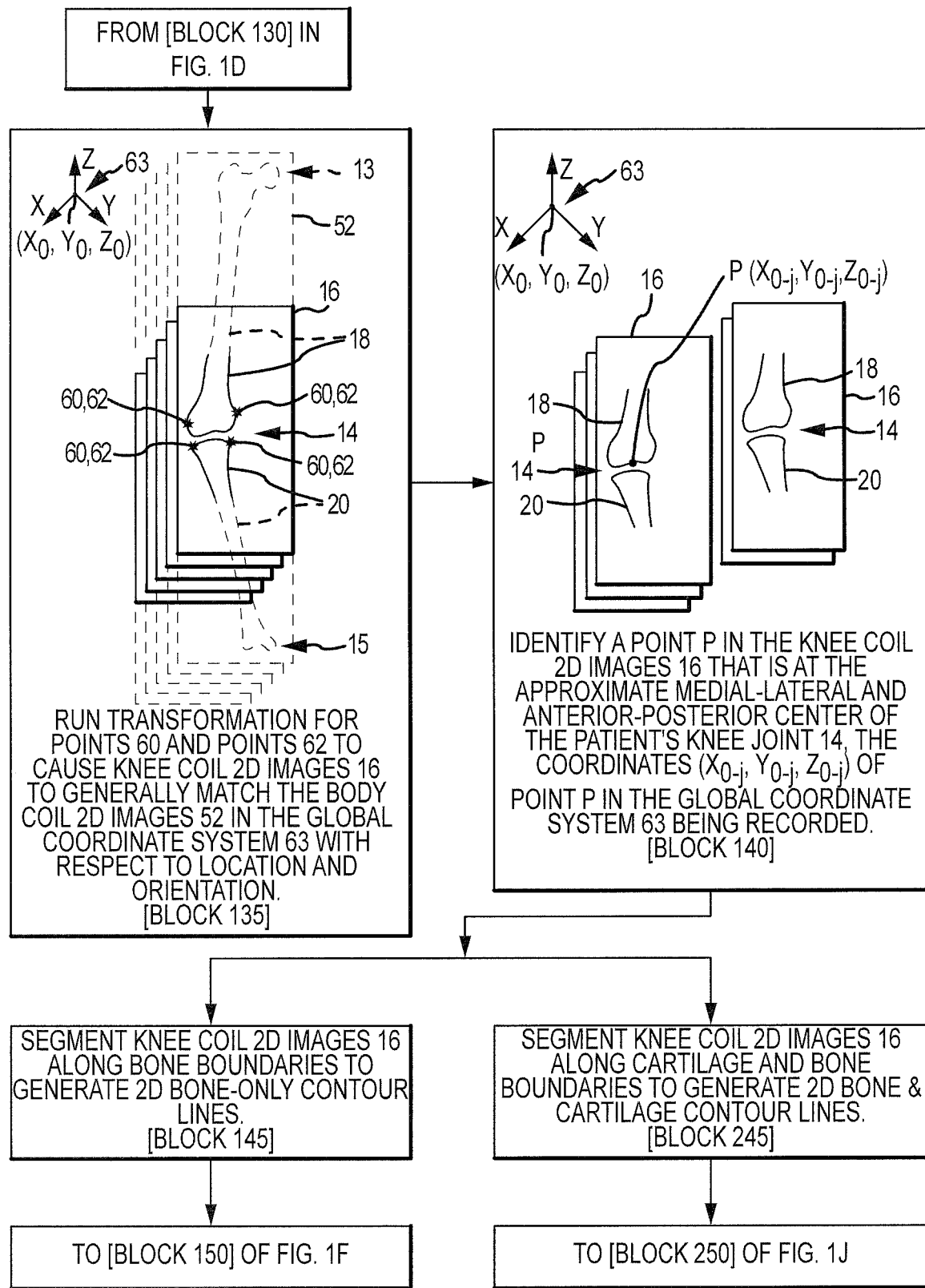
Figure 1F:
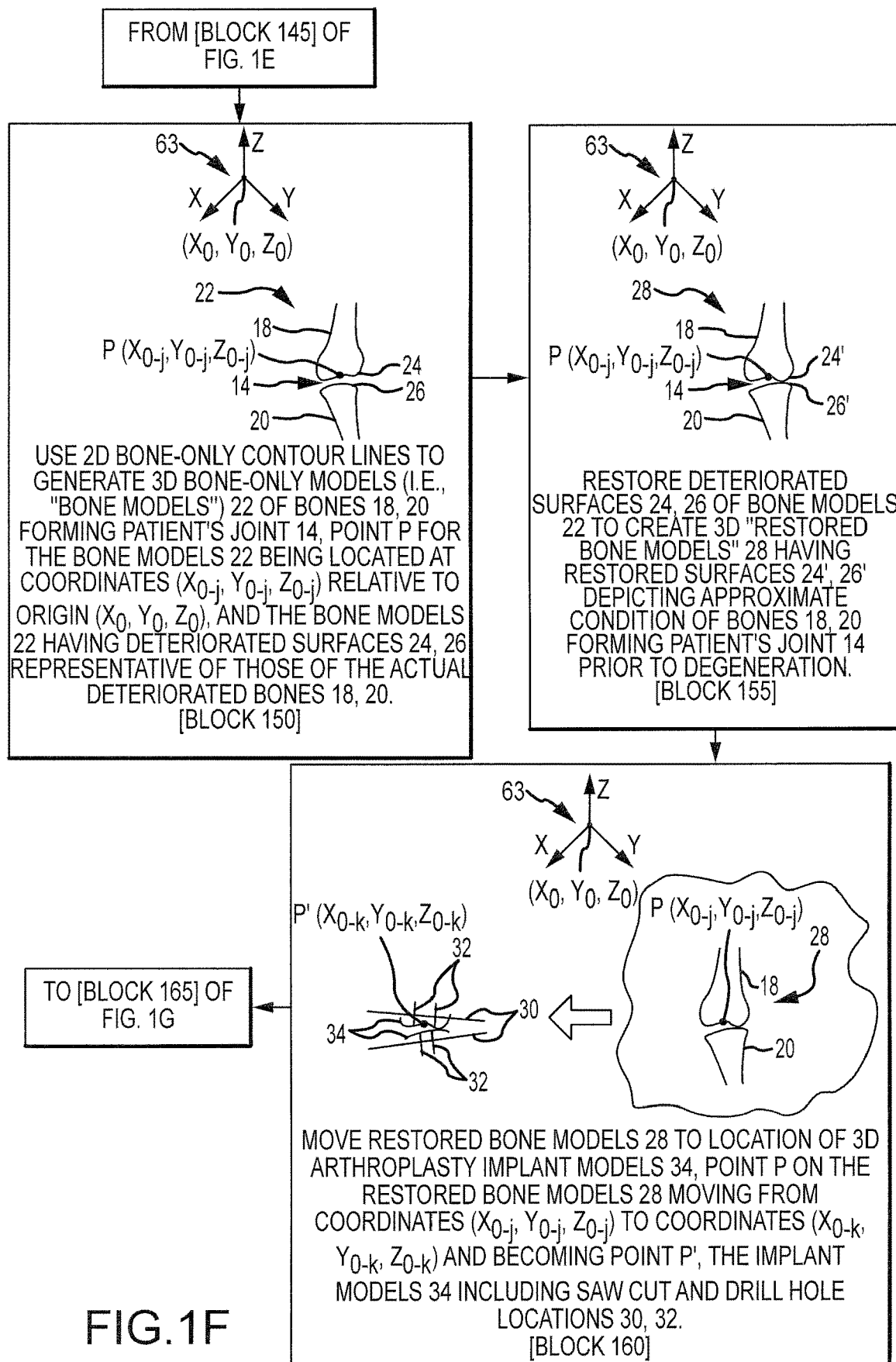
Figure 1G:
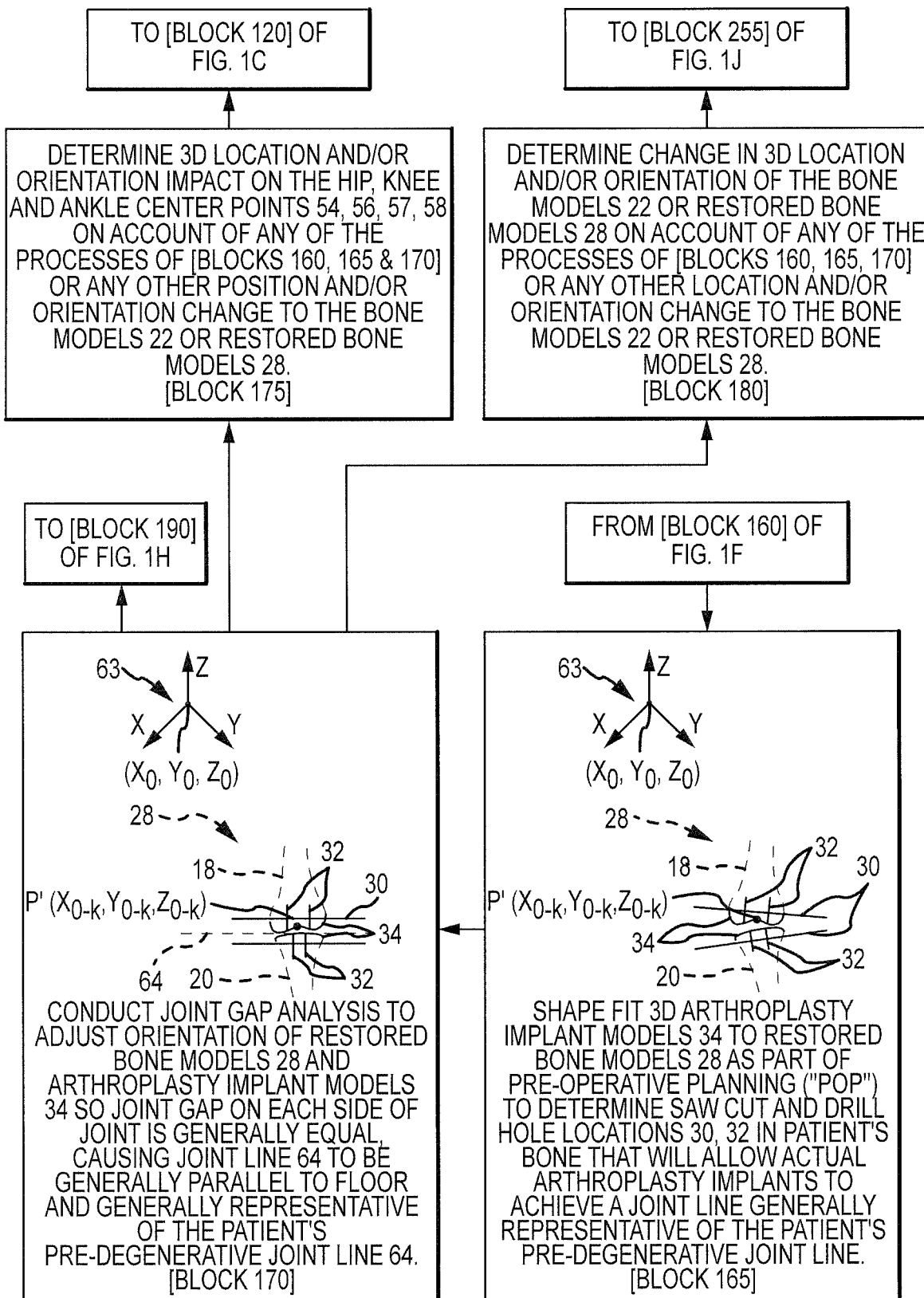

The second section, which is discussed with respect to FIG. 1A and [Blocks 140-170] of FIGS. 1E-1G, pertains to example methods of pre-operative planning ("POP") to determine bone resection locations and orientations in a knee arthroplasty. For example, the second section includes establishing a reference point P in the 2D knee coil MRI images 16, segmenting the 2D knee coil MRI images 16, generating 3D bone models 22 from the segmented images, generating 3D restored bone models 28 from the bone models 22, shape matching the 3D restored bone models 28 to 3D implant models 34 in a 3D computer model environment, noting the location and orientation of saw cut (bone resection) and drill hole locations 30, 32, and adjusting for ligament balance.

The resulting "saw cut and drill hole data" 44 is referenced to the restored bone models 28 to provide saw cuts and drill holes that will allow arthroplasty implants to achieve a joint alignment that is: (1) generally representative of the patient's pre-degenerative joint line (i.e., natural alignment); generally corresponding to a zero mechanical axis alignment, or (3) somewhere between (1) and (2). Whether the resections result in a joint alignment that is (1), (2) or somewhere between (1) and (2) may be a result of physician input and modification of the natural joint alignment calculated during POP.

Figure 1H:
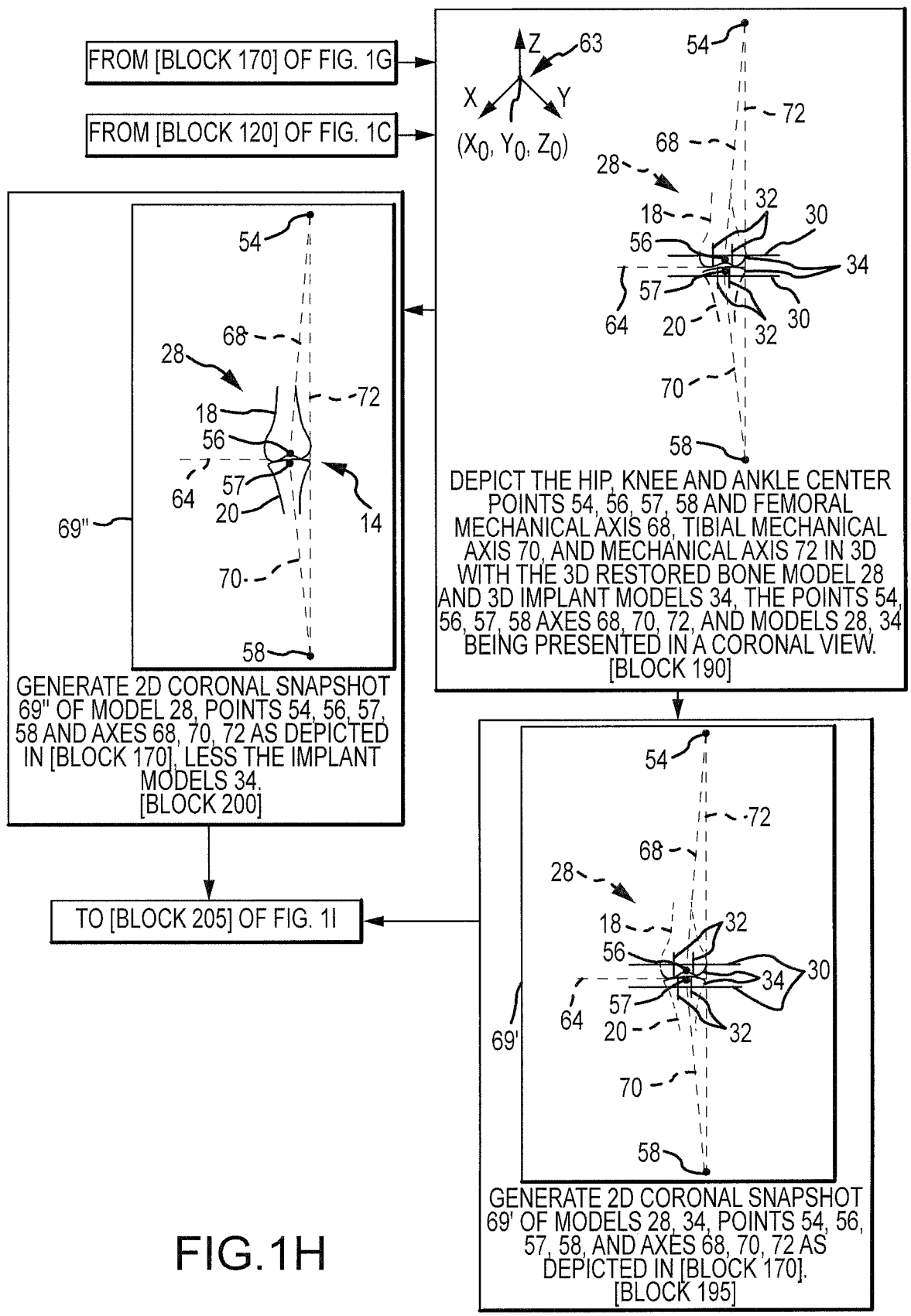
Figure 1I:
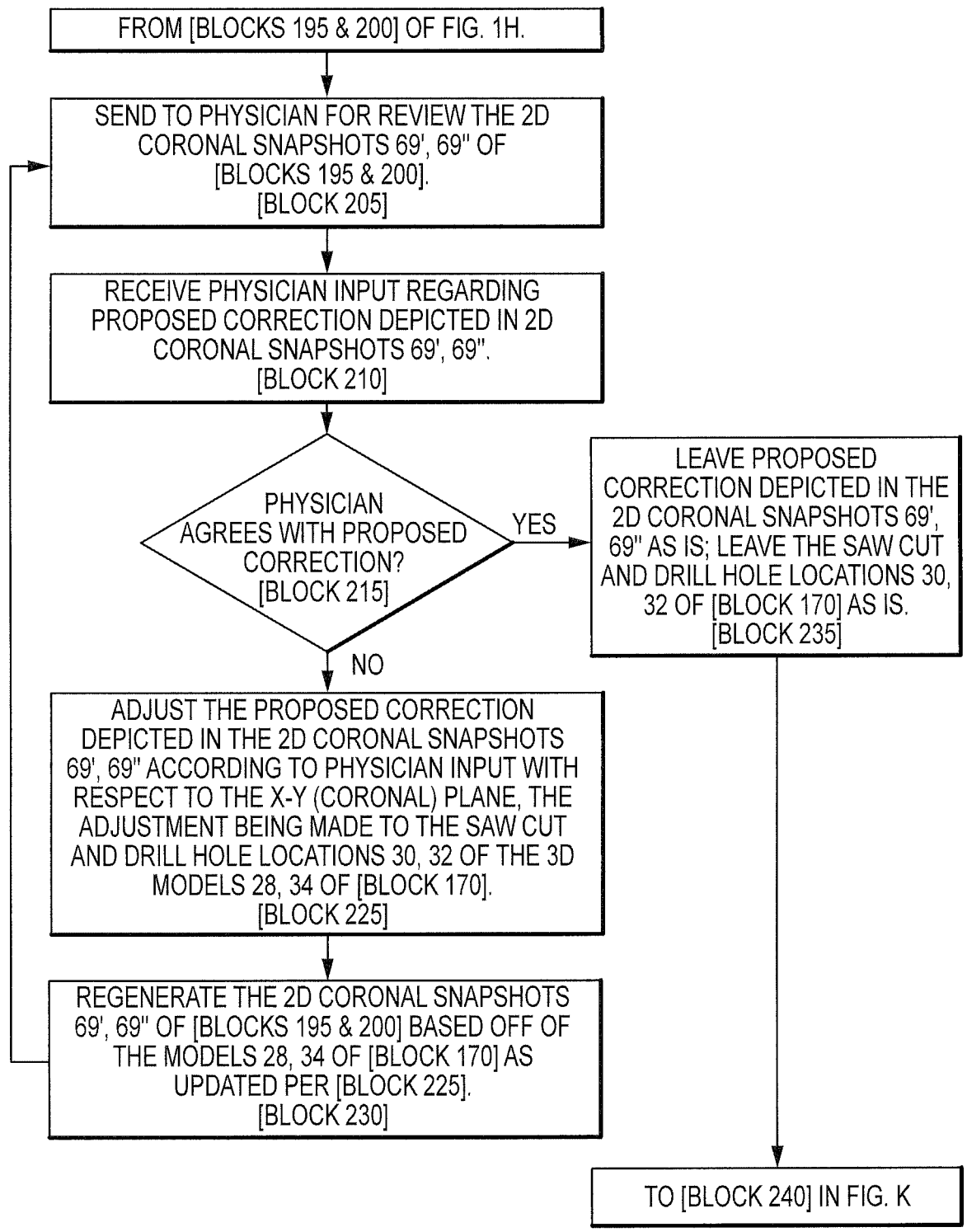

The third section, which is discussed with respect to [Blocks 190-235] of FIGS. 1H-1I, pertains to example methods of presenting information to the surgeon regarding the POP and, more specifically, the resections 30, joint line 64, femoral mechanical axis ("FMA") 68, tibial mechanical axis ("TMS") 70, and mechanical axis ("MA") 72. The surgeon provides approval of the present POP information or directions to modify the POP The fourth section, which is discussed with respect to [Blocks 120, 175, 180 and 255] of FIGS. 1C, 1G and 1J, pertains to examples of methods of maintaining location and orientation relationships between the various 3D models 22, 28, 36 and center points 54, 56, 57, 58 as the various 3D models 22, 28, 36 are modified or otherwise manipulated.

Figure 1J:
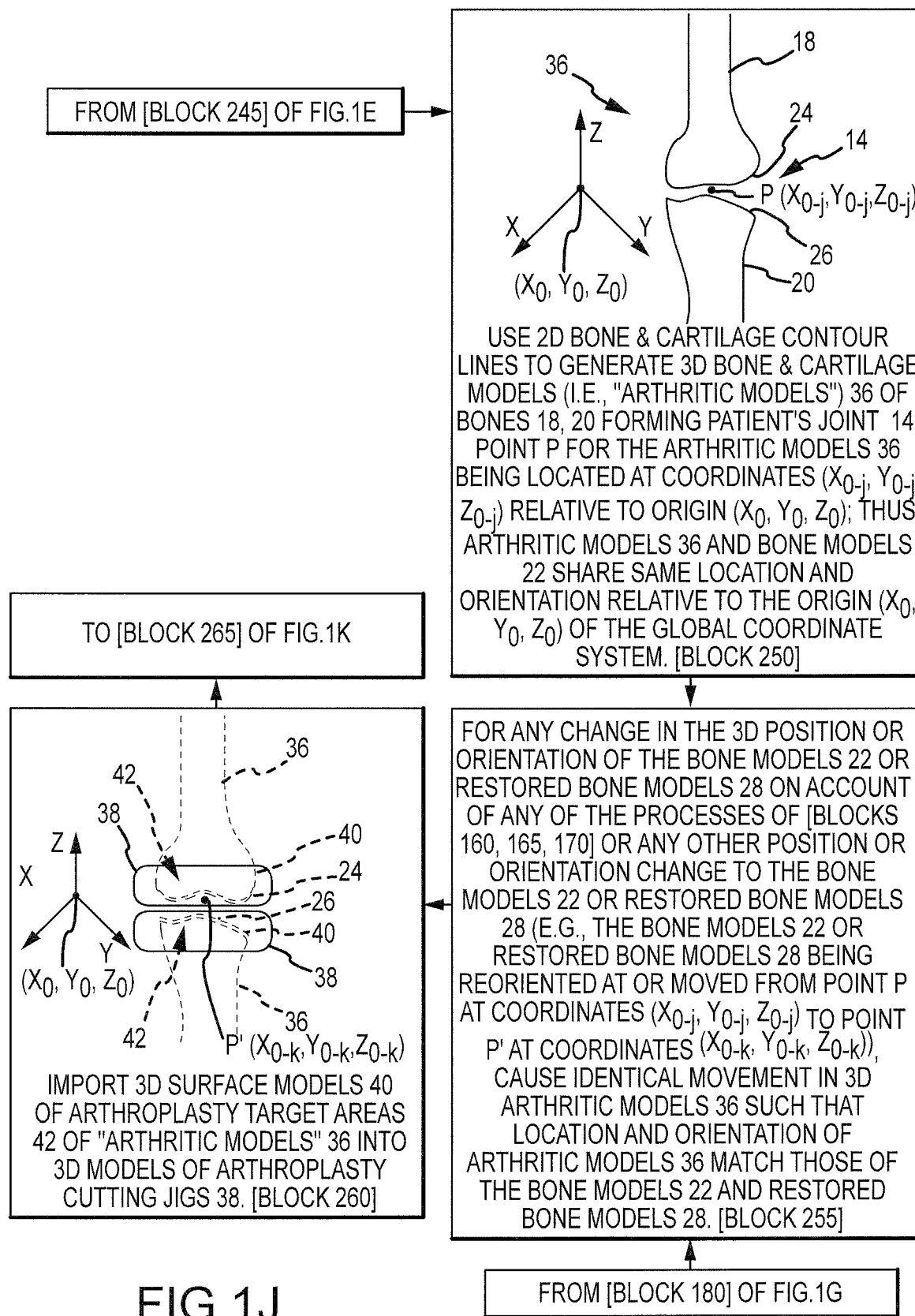

The fifth section, which is discussed with respect to FIG. 1A and [Blocks 180 and 245-260] of FIGS. 1E, 1G and 1J, pertains to example methods of generating 3D arthritic models 36 from the segmented images, importing into the 3D computer generated jig models 38 3D computer generated surface models 40 of arthroplasty target areas 42 of the 3D computer generated arthritic models 36 of the patients joint bones, and updating the location and orientation of the these models 36, 38, 40 to maintain the location and position relationship with the bone models 22, 28 that are manipulated during POP. The resulting "jig data" 46 is used to produce a jig customized to matingly receive the arthroplasty target areas of the respective bones of the patient's joint.

Figure 1K:
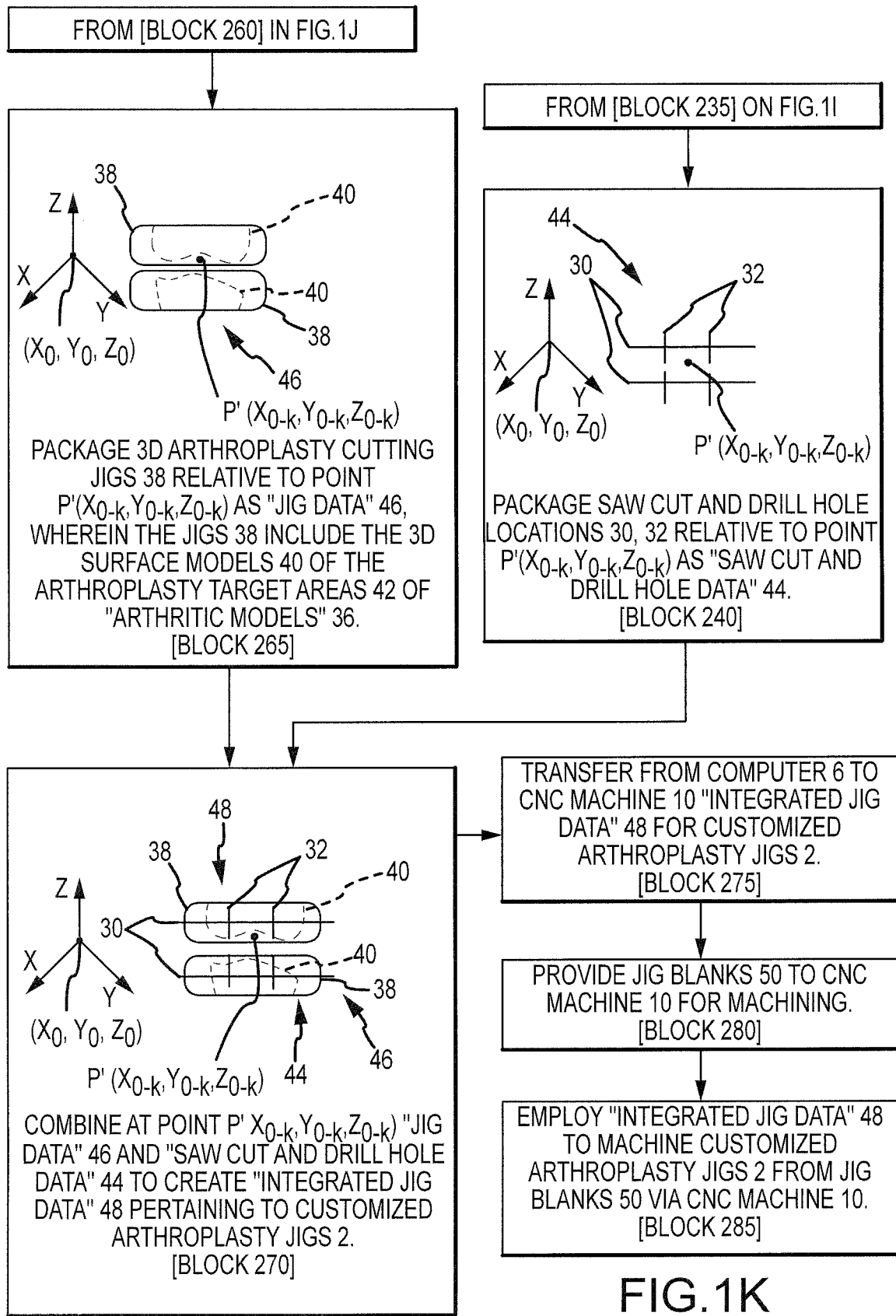

The sixth section, which is discussed with respect to FIG. 1A and [Blocks 240 and 265-285] of FIG. 1K, pertains to methods of combining or integrating the "saw cut and drill hole data" 44 with the "jig data" 46 to result in "integrated jig data" 48. The "integrated jig data" 48 is provided to the CNC machine 10 or another automated production machine, such as, for example, a rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to achieve a predetermined or desired joint alignment. Depending on the physician's review and input as outlined in [Blocks 190-235] of FIGS. 1H-1I, the predetermined or desired joint alignment will: generally restore the patient's joint line to its pre-degenerated state or natural alignment state; generally correspond to a zero degree mechanical axis alignment or be somewhere between natural alignment and zero degree mechanical axis alignment.

As shown in GIG. 1A, the system 4 includes a computer 6 having a CPU 7, a monitor or screen 9 and operator interface controls 11. The computer 6 is linked to a medical imaging system 8, such as a CT or MRI machine 8, and a computer controlled manufacturing system 10, such as a CNC milling machine 10.

As indicated in FIG. 1A, a patient 12 has a hip joint 13, a knee joint 14, and an ankle joint 15, wherein the knee joint 14 is to be the subject of the arthroplasty procedure. In other embodiments, the joint 14 to be replaced may be another type of joint, for example, an elbow, ankle, wrist, hip, shoulder, skull/vertebrae or vertebrae/vertebrae interface, etc. As discussed in greater detail below, in one embodiment, the patient 12 has the hip, knee and ankle joints 13, 14, 15 scanned in the imaging machine 8. The imaging machine 8 makes a plurality of scans of the joints 13, 14, 15 wherein each scan pertains to a thin slice of a single joint or multiple joints.

Figure 6:
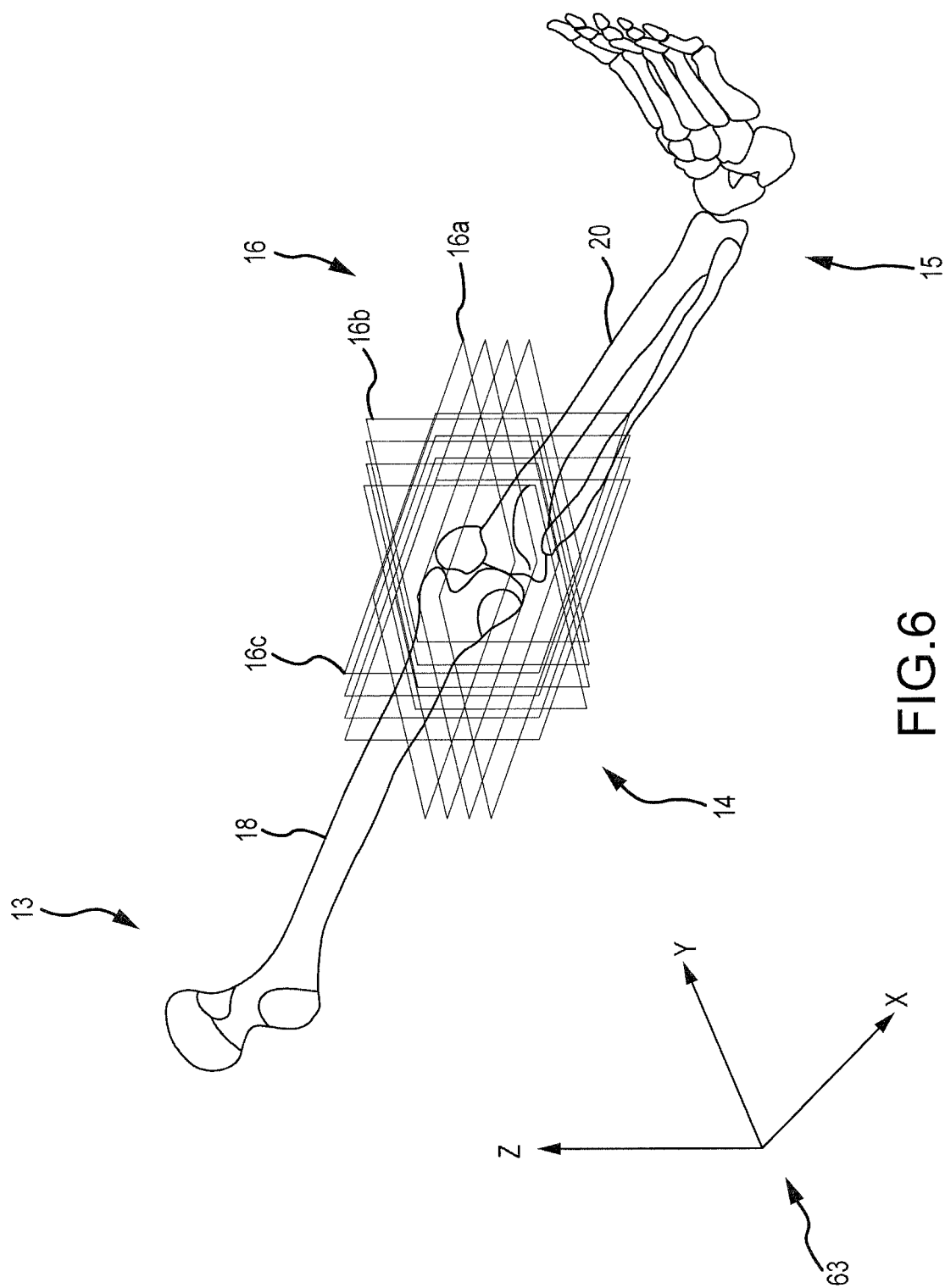
FIG. 6 is an isometric view of the patient's leg bone structure illustrating knee coil images.

As can be understood from FIG. 1B, in one embodiment, the patient's leg bone structure undergoes two types of scanning in the imaging machine 8. Specifically, as indicated in FIG. 6, which is an isometric view of the patient's leg bone structure, in one embodiment, the patient's knee 14, including portions of the femur 18 and tibia 20, is scanned in a MRI knee coil to generate a plurality of two dimensional ("2D") knee coil NMI images 16 of the patient's knee 14 [Block 100]. In one embodiment, the knee coil 2D images 16 include a plurality of coronal images 16*a*, a plurality of axial images 16*b* and a plurality of sagittal images 16*c*. In other embodiments, the knee coil 2D images 16 may be any combination of coronal, sagittal and/or axial views; for example, the views making up the images 16 may be coronal plus sagittal, coronal plus sagittal plus axial, coronal plus axial, etc. The knee coil 2D images 16 have a location and orientation in a global coordinate system 63 having an origin (X0, Y0, Z0). In one embodiment, the MRI imaging spacing for the 2D knee coil images 16 may range from approximately 2 mm to approximately 6 mm.

Figure 7:
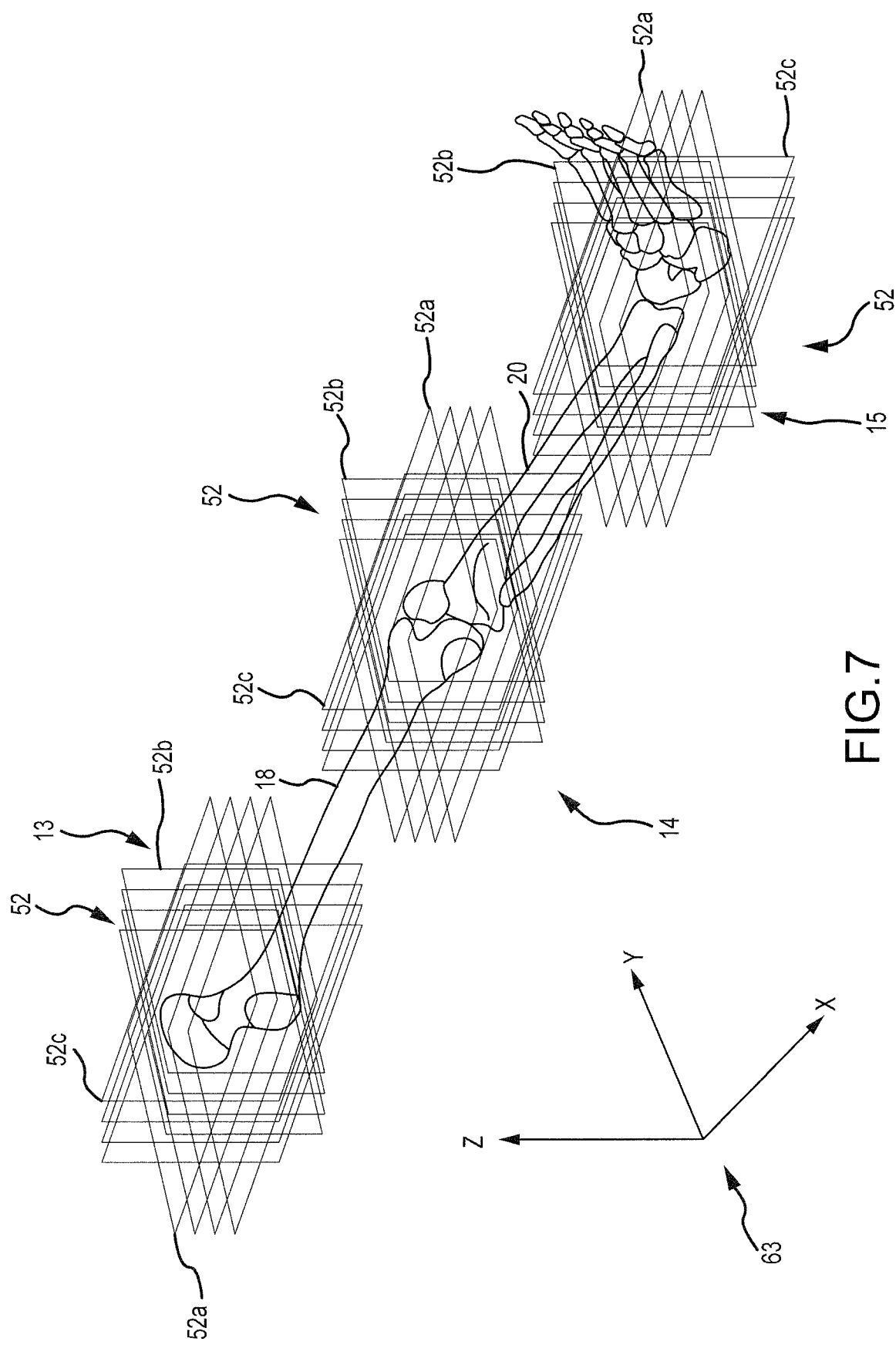
FIG. 7 is an isometric view of the patient's leg bone structure illustrating body coil images.

As illustrated in FIG. 7, which is an isometric view of the patient's leg bone structure, in one embodiment, the patient's entire leg length, or portions thereof that include the patient's hip 13, knee 14 and ankle 15, is scanned in a MRI body coil to generate a plurality of 2D body coil MSI images 52 of the patient's entire leg length or, at least, a plurality of body coil 2D Mill images 52 at each of the patient's the hip 13, knee 14 and ankle 15 [Block 105]. In other words, the body coil 2D images 52 include all of hip 13, knee 14 and ankle 15 or, at least, certain portions thereof. In one embodiment, the body coil 2D images 52 include a plurality of coronal images 52a, a plurality of axial images 52b and a plurality of sagittal images 52c at each of the hip 13, knee 14 and ankle 15. In other embodiments, the body coil 2D images 52 may be any combination of coronal, sagittal and/or axial views; for example, the views making up the images 52 may be coronal plus sagittal, coronal plus sagittal plus axial, coronal plus axial, etc. The body coil 2D images 52 have a location and orientation in the global coordinate system 63 having the origin (X0, Y0, Z0). In one embodiment, the MRI imaging spacing for the 2D body coil images 52 may range from approximately 0.5 mm to approximately 5 mm. As a result, the number of generated MRI imaging slices for the knee coil approach is larger than the body coil approach. In other words, the numbers N for the knee coil and M for the body coil of MRI slices may be expressed as follows: N(coronal slices)>>M(coronal slices); N(sagittal slices)>>M(sagittal slices); and N(axial slices)>>M(axial slices).

As can be understood from FIG. 1B, in one embodiment, before performing the MRI scanning that will result in the body coil 2D images 52, the MRI localiser may be employed in the sagittal and axial views of the patient's leg bone structure to target the MRI scanning process at the centers of the patient's hip 13, knee 14 and ankle 15 [Block 103]. Thus, the MRI body coil scanning may be caused to focus at the centers of the hip, knee and ankle, increasing the likelihood of generating coronal body coil images that are adequate for identifying the centers of the hip, knee and ankle as discussed below.

While the embodiment is discussed in the context of the imaging being via MRI, in other embodiments the imaging is via. CT or other medical imaging methods and systems. In One embodiment employing MRI, the imaging process may be as disclosed in U.S. patent application Ser. No. 11/946, 002 to Park, which is titled "Generating MRI Images Usable For The Creation Of 3D Bone Models Employed To Make Customized Arthroplasty Jigs," was filed Nov. 27, 2007 and is incorporated by reference in its entirety into this Detailed Description.

Figure 14:
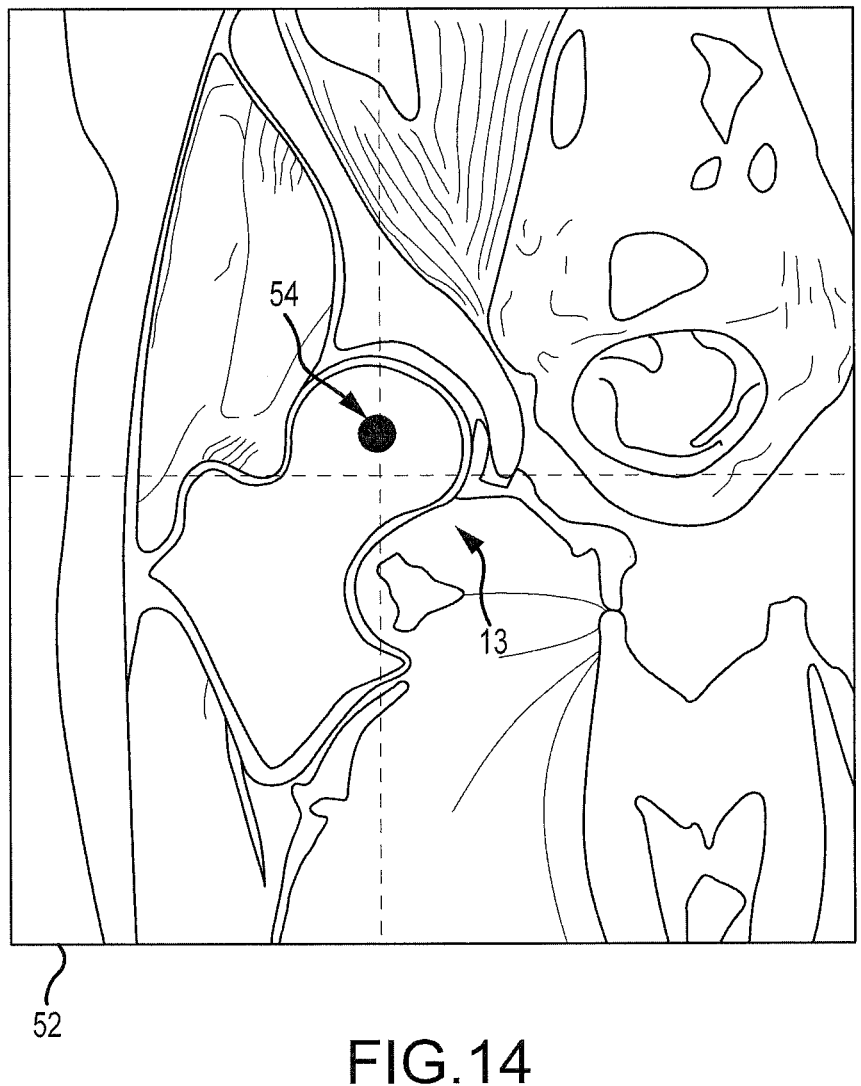
FIG. 14 is a coronal 2D body coil image of the hip with the center of the femoral head indicated.
Figure 15:
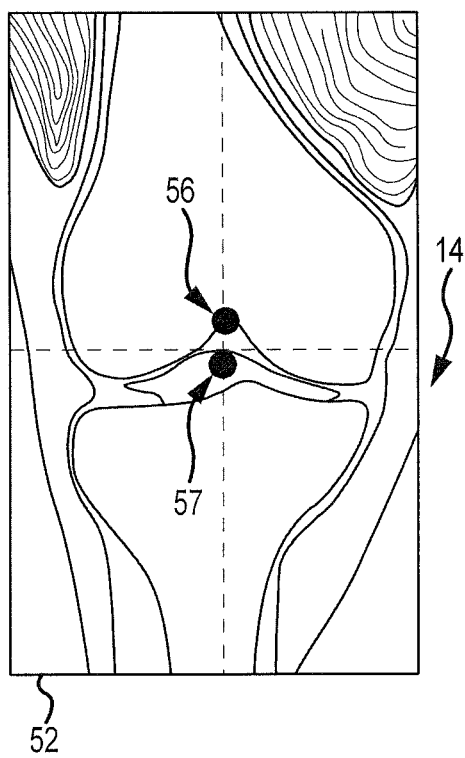
FIG. 15 is a coronal 2D knee coil image of the knee with the centers of the femur and tibia indicated.
Figure 16:
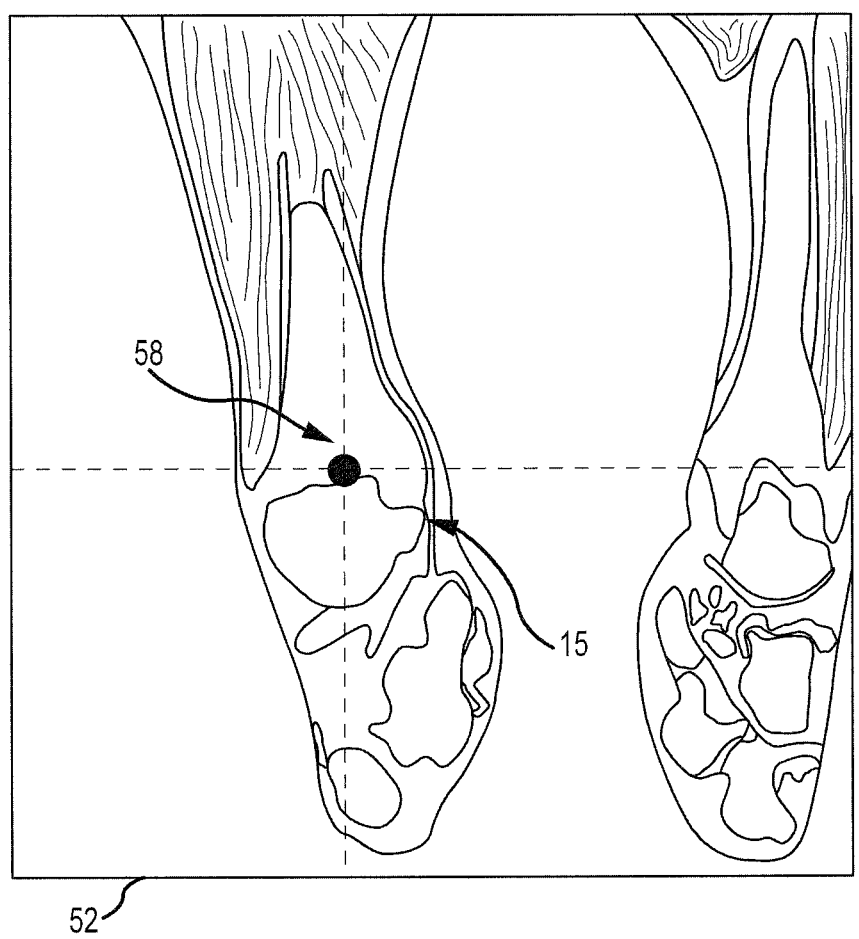
FIG. 16 is a coronal 2D body coil image of the ankle with the center of the ankle joint indicated.

As can be understood from FIG. 1A, the 2D images 16, 52 are sent to the computer 6 for analysis and modeling. As indicated in FIG. 1C, hip, knee and ankle centers 54, 56, 57, 58 are identified in the body coil 2D images 52 [Block 110]. For example, as indicated FIGS. 14-16, which are coronal 2D body coil images 52 of the hip 13, knee 15 and ankle 16, respectively, a person sitting in front of the monitor 9 of the work station 6 tabs through the various coronal 2D body coil images 52 at each of the hip, knee and ankle to determine visually an image 52 at each of the hip, knee and ankle that is near the center of each of these joints 13, 14, 15. When the operator visually identifies such an image for each of the joints 13, 14, 15, the operator electronically marks the centers 54, 56, 57, 58 for each of these joints 13, 14, 15, as indicated in FIGS. 14-16, causing the location of the centers 54, 56, 57, 58 to be electronically stored relative to the global coordinate system 63.

In one embodiment, the hip, knee and ankle centers 54, 56, 57, 58 are identified only in the coronal views of the body coil 2d images 52. In one embodiment, the X, Y and Z global coordinate locations for each of the femur hip center 54, femur knee center 56, tibia knee center 57 and tibia ankle center 58 are stored, for example, in a table or matrix in a computer file separate from the 3D bone models 22 or 3D restored bone models 28, discussed below [Block 115]. In other embodiments, the X, and Z global coordinate locations for each of the femur hip center 54, femur knee center 56, tibia knee center 57 and tibia ankle center 58 are stored with or as part of the 3D bone models 22 or 3D restored bone models 28, discussed below.

In one embodiment, the hip center can be the approximate center point of the femur head via visual examination. The ankle center can be the approximate center point of the cortical bone rim of the ankle plafond (i.e., the distal articular surface of tibia) via visual examination. The knee center can be the approximate center point close to the intercondylar groove of the distal femur and/or the approximate center point of the tibia spine in the 3D restored knee model. The centers of the hip and ankle in the 2D body coil images 52 may be identified. The approximate joint center coordinates of the hip, ankle and 3D knee model may be recorded as (x'1-3, y'1-3, z'1-3). For example, the joint center coordinates for each of hip, knee, and ankle, may be, respectively, (x'1, y'1, z'1), (x'2, y'2, z'2), and (x'3, y'3, z'3).

Figure 8:
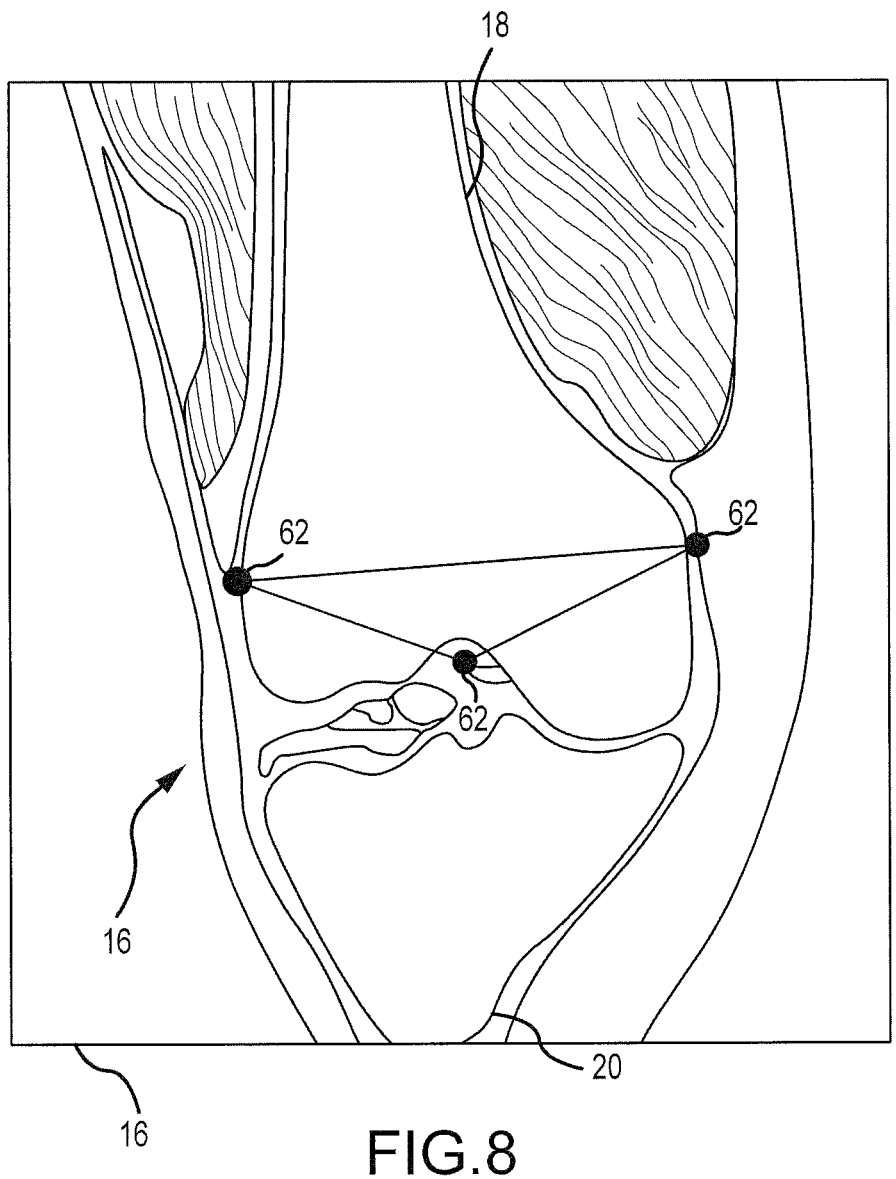
FIG. 8 is a coronal 2D knee coil image with points identified on landmarks of the knee region of the femur.

As shown in FIG. 1D, points 60 and 62 are identified respectively on corresponding landmarks in the 2D body coil images 52 and 2D knee coil images 16 [Block 125]. For example, as shown in FIG. 8, which is a coronal 2D knee coil image 16, points 62 are identified on landmarks of the knee region of the femur 18. In some embodiments, the 2D knee coil image 16 used to identify the landmarks of the knee region of the femur 18 is the 2D knee coil image 16 of the set of knee coil images 16 having the widest and most clear or definite depiction of the femur 18 in the knee region. For example, a person viewing the 2D knee coil images 16 via the monitor 9 of the work station 6 may tab through the various coronal 2D knee coil images 16 to determine the specific coronal 2D knee coil image 16 in which the femur 18 is depicted with the largest and most clear condyle contour. The person then marks or identifies the points 62 of the femur landmarks. As shown in FIG. 8, examples of such landmarks on the knee region of the femur may include the center of the femur condyle region near the trochlear groove, the most medial and lateral points of the epicondyles, or other identifiable landmarks.

Figure 9:
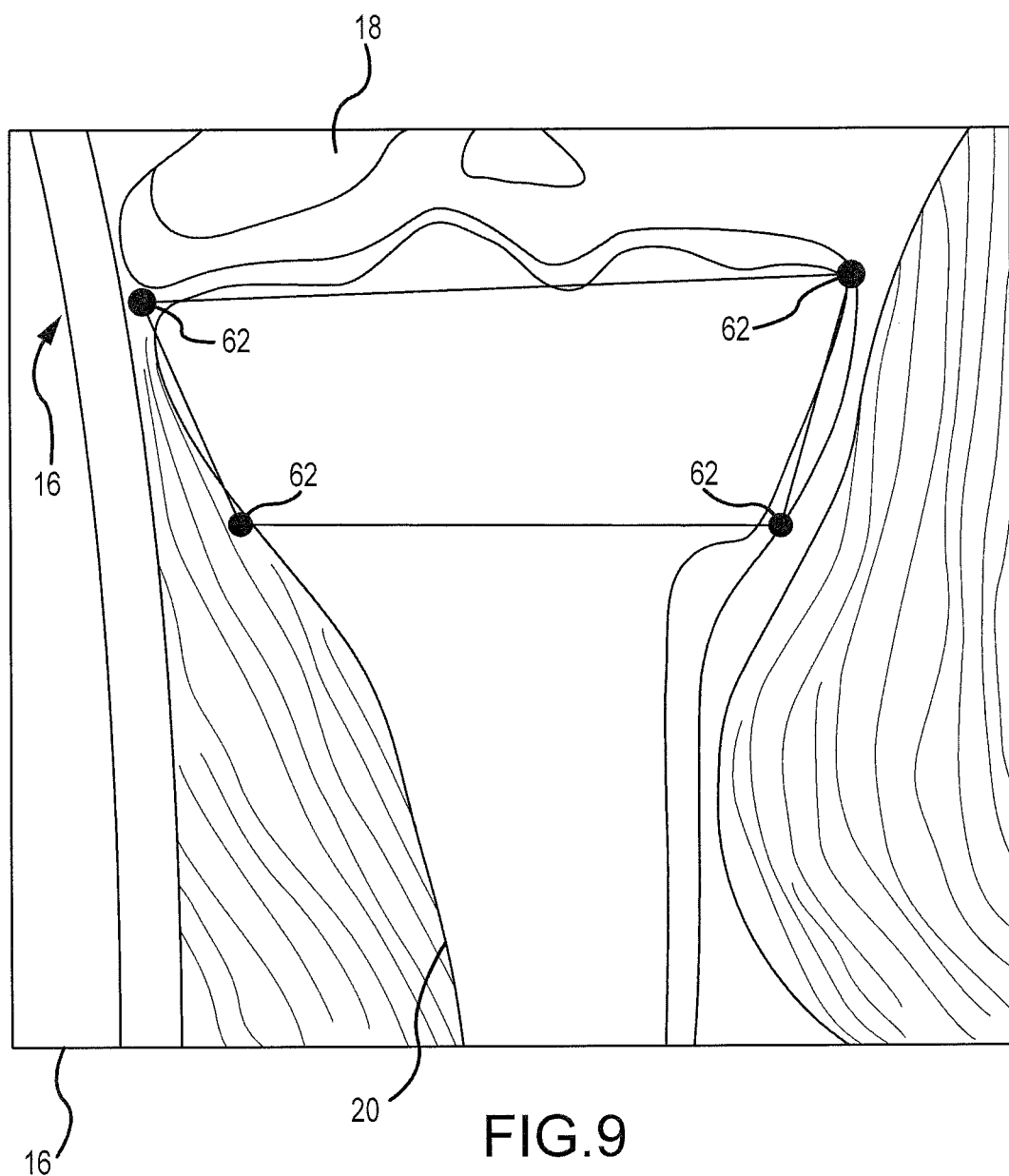
FIG. 9 is a coronal 2D knee coil image with points identified on landmarks of the knee region of the tibia.

As shown in FIG. 9, which is a corona 2D knee coil image 16, points 62 may also be identified on landmarks of the knee region of the tibia 20. In some embodiments, the 2D knee coil image 16 used to identify the landmarks of the knee region of the tibia 20 is the 2D knee coil image 16 of the set of knee coil images 16 having the widest and most clear or definite depiction of the tibia 20 in the knee region. For example, a person viewing the 2D knee coil images 16 via the monitor 9 of the work station 6 may tab through the various coronal 2D knee coil images 16 to determine the specific coronal 2D knee coil image 16 in which the tibia 20 is depicted with the largest and most clear condyle contour. The person then marks or identifies the points 62 of the tibia landmarks. As shown in FIG. 9, examples of such landmarks on the knee region of the tibia may include the medial and lateral edges of the tibial condyles, the medial and lateral transitions from the tibial plateau to the tibial shaft, or other identifiable landmarks.

Figure 10:
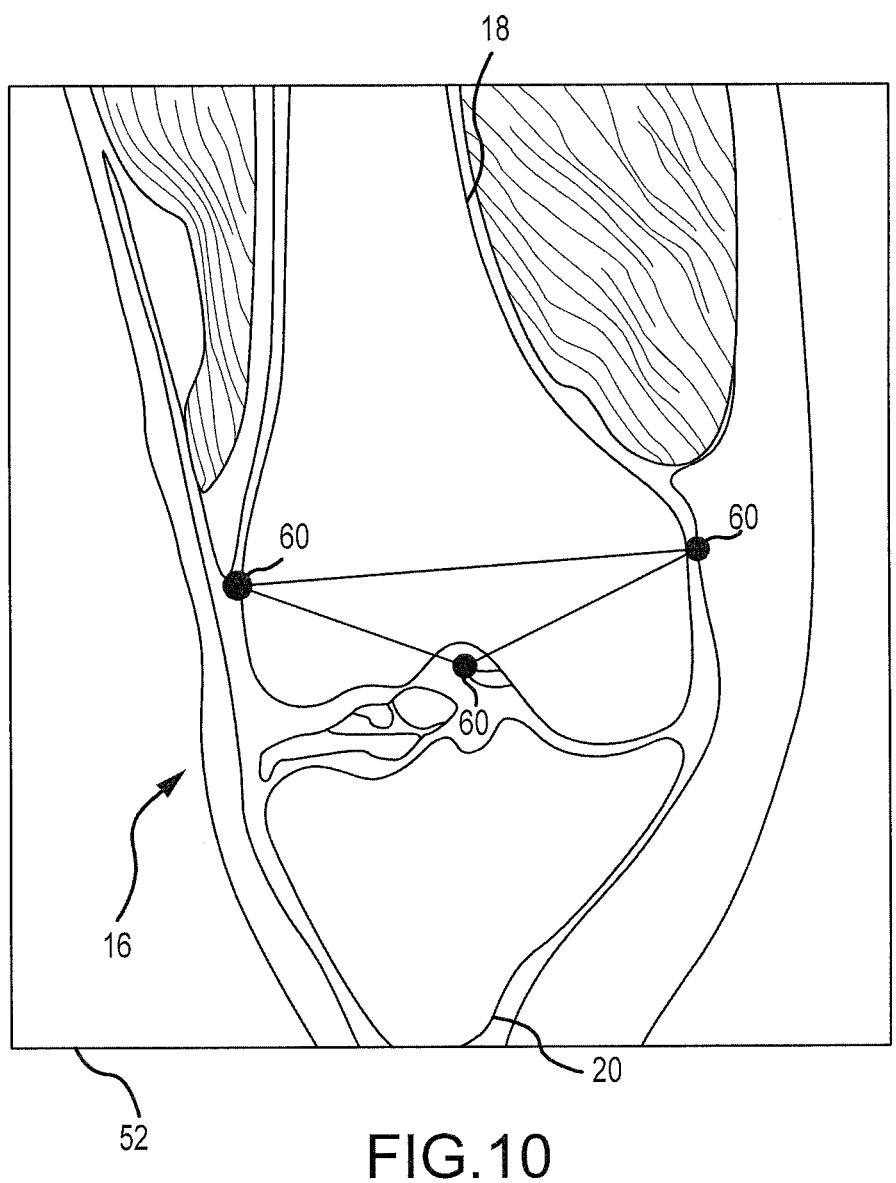
FIG. 10 is a coronal 2D body coil image with points identified on landmarks of the knee region of the femur.

As shown in FIG. 10, which is a coronal 2D body coil image 52, points 60 are identified on landmarks of the knee region of the femur 18. In some embodiments, the 2D body coil image 52 used to identify the landmarks of the knee region of the femur 18 is the 2D body coil image 52 of the set of body coil images 52 having the widest and most clear or definite depiction of the femur 18 in the knee region. For example, a person viewing the 2D body coil images 52 via the monitor 9 of the work station 6 may tab through the various coronal 2D body coil images 52 to determine the specific coronal 2D body coil image 52 in which the femur 18 is depicted with the largest and most clear condyle contour. The person then marks or identifies the points 60 of the femur landmarks, which, as can be understood from a comparison of FIGS. 10 and 8, will be selected to be at least generally the same as the points 62 of the femur landmarks identified in the coronal 2D knee coil image 16.

Figure 11:
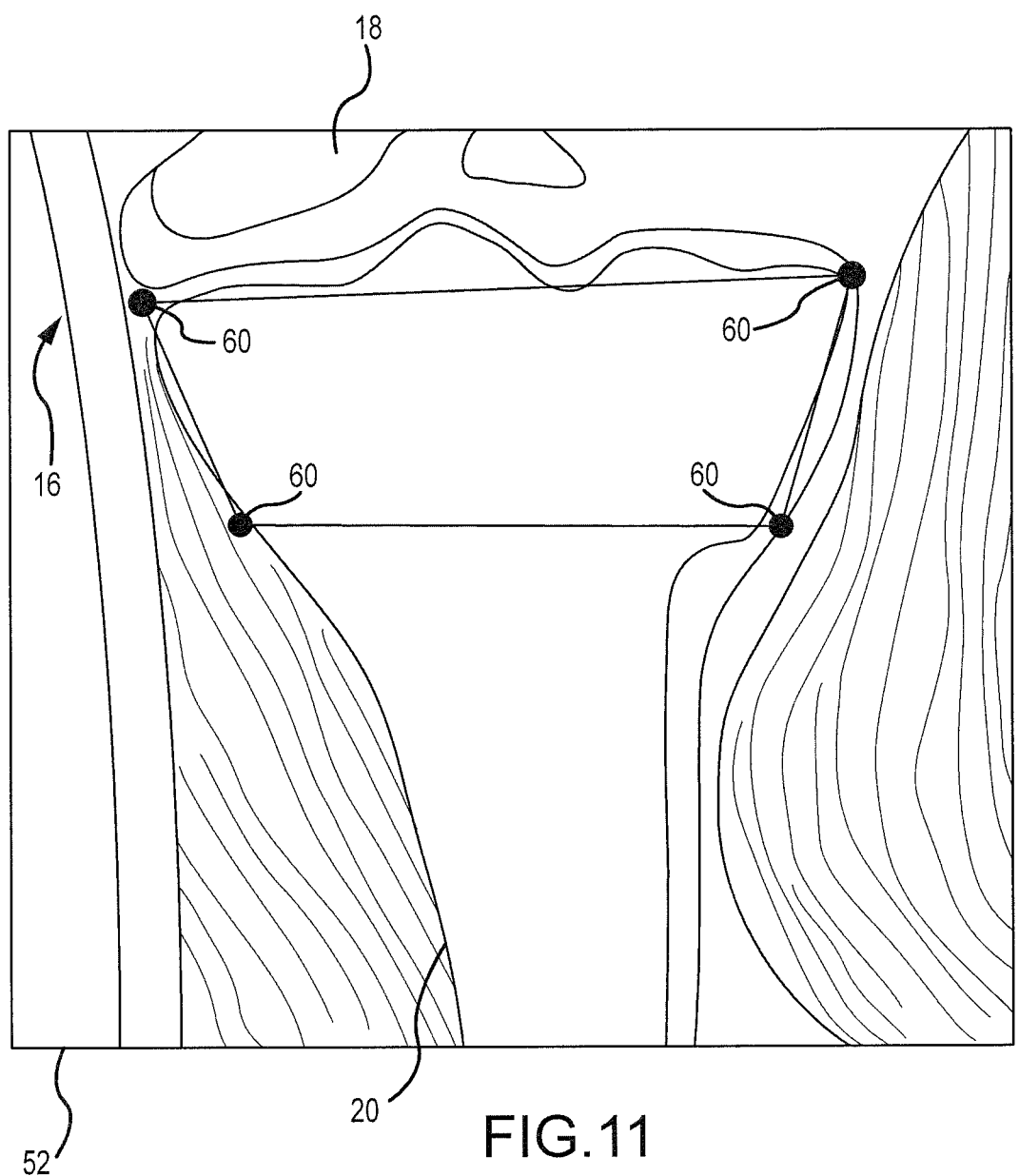
FIG. 11 is a coronal 2D body coil image with points identified on landmarks of the knee region of the tibia.

As shown in FIG. 11, which is a coronal 2D body coil image 52, points 60 are also identified on landmarks of the knee region of the tibia 20. In some embodiments, the 2D body coil image 52 used to identify the landmarks of the knee region of the tibia 20 is the 2D body coil image 52 of the set of body coil images 52 having the widest and most clear or definite depiction of the tibia 20 in the knee region. For example, a person viewing the 2D body coil images 52 via the monitor 9 of the work station 6 may tab through the various coronal 2D body coil images 52 to determine the specific coronal 2D body coil image 52 in which the tibia 20 is depicted with the largest and most clear condyle contour. The person then marks or identifies the points 60 of the tibia landmarks, which, as can be understood from a comparison of FIGS. 11 and 9, will be selected to be at least generally the same as the points 62 of the tibia landmarks identified in the coronal 2D knee coil image 16.

In one embodiment, three or more points 62 are identified in the respective 2D knee coil images 16 of FIGS. 8 and 9, and three or more points 60 are identified in the respective 2D body coil images 52 of FIGS. 10 and 11. The three or more femur points 62 may be in the same coronal 2D knee coil image 16, as illustrated in FIG. 8, and the three or more tibia points 62 may be in the same coronal 2D knee coil image 16, as depicted in FIG. 9. Similarly, the three or more femur points 60 may be in the same coronal 2D body coil image 52, as illustrated in FIG. 10, and the three or more tibia points 60 may be in the same coronal 2D body coil image 52, as depicted in FIG. 11.

In other embodiments, the three or more points 60, 62 may be distributed across multiple coronal images 16, 52. For example, the three or more femur points 62 may be distributed across two or more coronal 2D knee coil images 16, and the three or more tibia points 62 may be distributed across two or more coronal 2D knee coil images 16. Similarly, the three or more femur points 60 may be distributed across two or more coronal 2D body coil images 52, and the three or more tibia points 60 may be distributed across two or more coronal 2D body coil images 52.

In yet other embodiments, the three or more points 60, 62 may be distributed across different types of images 16, 52, such as, for example, a combination of coronal, axial and/or sagittal. For example, the three or more femur points 62 may be distributed across one or more coronal 2D knee coil image 16, one or more sagittal knee coil image, and/or one or more axial knee coil image, and the three or more tibia points 62 may be distributed across one or more coronal 2D knee coil image 16, one or more sagittal knee coil image, and/or one or more axial knee coil image. Similarly, the three or more femur points 60 may be distributed across one or more coronal 2D body coil image 52, one or more sagittal body coil image, and/or one or more axial body coil image, and the three or more tibia points 60 may be distributed across one or more coronal 2D body coil image 52, one or more sagittal body coil image, and/or one or more axial body coil image.

Regardless of how many points 60, 62 are located and in which type of image views and combinations of views, in one embodiment, the coordinate locations of the points 60, 62 in the global coordinate system 63 are stored for use with the transformation process discussed below.

Figure 12:
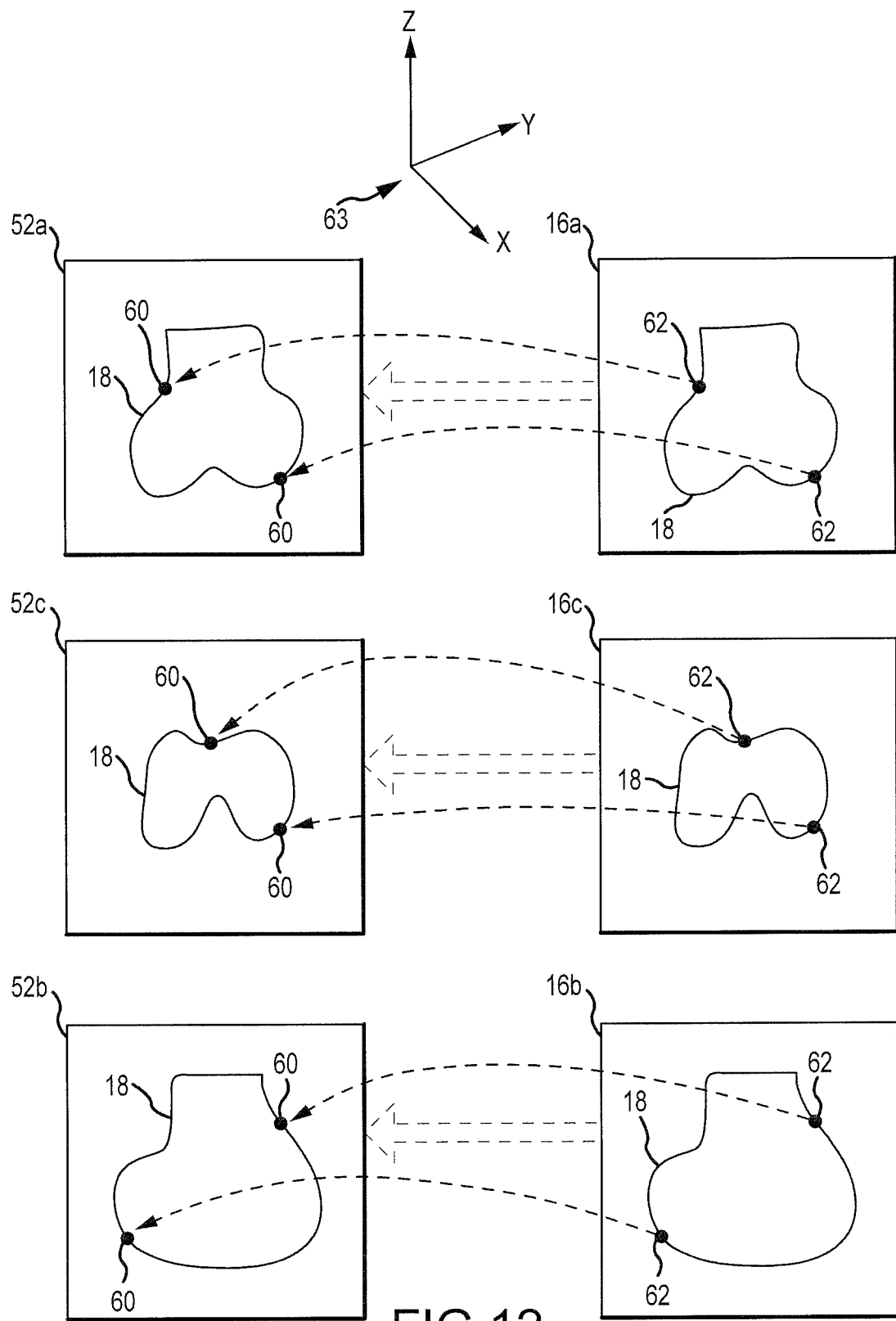
FIG. 12 is a diagrammatic depiction of the femur 2D knee coil images being transformed to the femur 2D body coil images.

As can be understood from FIG. 1D, the 2D knee coil images 16 are moved to the location of the 2D body coil images 52 in the global coordinate system 63, or vice versa [Block 130] As can be understood from FIG. 1E, a transformation is run for the points 60, 62 to cause the 2D knee coil images 16 to generally positionally match the 2D body coil images 52 with respect to both location and orientation [Block 135]. Specifically, as can be understood from FIG. 12, which is a diagrammatic depiction of the femur images 16, 52 being transformed, the transformation, in one embodiment, causes the coronal 2D knee coil images 16a to move to and positionally match the coronal 2D body coil images 52a by positioning the points 62 of the coronal 2D knee coil images 16a at the positions of the corresponding points 60 of the coronal 2D body coil images 52a in the global coordinate system 63. The embodiment of the transformation also causes the axial 2D knee coil images 16b to move to and positionally match the axial 2D body coil images 52b by positioning the points 62 of the axial 2D knee coil images 16b at the positions of the corresponding points 60 of the axial 2D body coil images 52b in the global coordinate system 63. The embodiment of the transformation also causes the sagittal 2D knee coil images 16c to move to and positionally match the sagittal 2D body coil images 52c by positioning the points 62 of the sagittal 2D knee coil images 16c at the positions of the corresponding points 60 of the sagittal 2D body coil images 52c in the global coordinate system 63.

Figure 13:
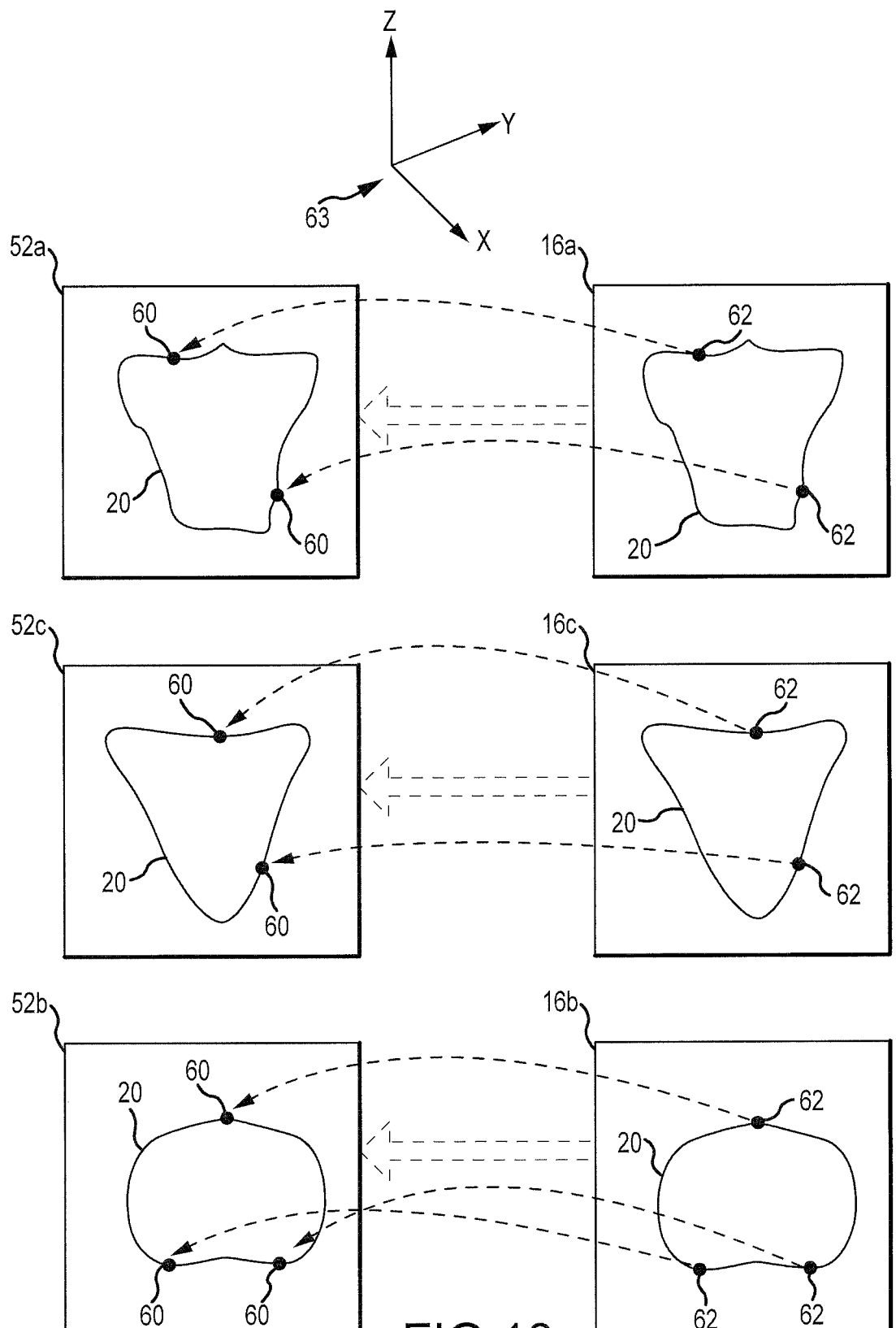
FIG. 13 is a diagrammatic depiction of the tibia 2D knee coil images being transformed to the tibia 2D body coil images.

As can be understood from FIG. 13, which is a diagrammatic depiction of the tibia images 16, 52 being transformed, the transformation, in one embodiment, causes the coronal 2D knee coil images 16a to move to and positionally match the coronal 2D body coil images 52a by positioning the points 62 of the coronal 2D knee coil images 16a at the positions of the corresponding points 60 of the coronal 2D body cod images 52a in the global coordinate system 63. The embodiment of the transformation also causes the axial 2D knee coil images 16b to move to and positionally match the axial 2D body coil images 52b by positioning the points 62 of the axial 2D knee coil images 16b at the positions of the corresponding points 60 of the axial 2D body coil images 52b in the global coordinate system 63. The embodiment of the transformation also causes the sagittal 2D knee coil images 16c to move to and positionally match the sagittal 2D body coil images 52c by positioning the points 62 of the sagittal 2D knee coil images 16c at the positions of the corresponding points 60 of the sagittal 2D body coil images 52c in the global coordinate system 63.

Whether the transformation operates on points in a particular view (e.g., coronal, axial and/or sagittal) or on a particular bone (e.g., femur and/or tibia) will depend on which landmarks the points 60, 62 are identified and in which views, as discussed above with respect to [Block 125] of FIG. 1D.

In one embodiment, the MRI coordinates of the points 60 on the bone landmarks of the region of the knee 14 in the 2D body coil images 52 may be illustrated as (x, y, z) and stored for further analysis. Similarly, the MRI coordinates of the points 62 on the bone landmarks of the region of the knee 14 in the 2D knee coil images 16 may be illustrated as $(\hat{x}, \hat{y}, \hat{z})$ and stored for further analysis. In one embodiment, the landmarks on which the points 60, 62 are located may be the epicondylar points of the distal femur, the approximate center of distal femur, the approximate center of proximal tibia, or other recognizable landmarks. In another embodiment, the points 60, 62 can be located anywhere on the area of distal femur and proximal tibia. The points for both the knee coil images 16 and body coil images 52 are in approximately similar locations via visual examination.

Once the points 60, 62 are similarly located in the images 16, 52, the transformation or optimization of the points 60, 62 and associated images 16, 52 takes place by brining as close as possible the points 62 of the 2D knee coil images 16, which are stored as $(\hat{x}, \hat{y}, \hat{z})$, to the points of the 2D body coil images 52, which are stored as $(x, y, z)$. In other words, for example, the closeness of the two sets of points may be evaluated as the sum of squared distances from points in the first set to the whole second set. The manipulations of rotation and translation are applied to the points and associated images for the distal femur and proximal tibia.

In one embodiment, the transformation employs the Iterative Closest Point ("ICP") algorithm, gradient descent optimization or other optimization algorithms or transformations.

While [Blocks 125-135] of FIGS. 1D-1E and the preceding discussion illustrate a first positional matching embodiment wherein the 2D knee coil images 16 are positionally matched to the 2D body coil images 52 via the positional matching of landmark points 60, 62, other embodiments may employ other positional matching methods. For example, in a second positional matching embodiment and in a manner similar to that discussed below with respect to [Blocks 1415-150] of FIGS. 1E-1F, the 2D knee coil images 16 are segmented and converted into a 3D bone model 22. Landmark points 60 are identified in the 2D body coil images 52 and these landmark points 60 are positionally matched to corresponding landmark points 62 in the 3D bone model 22 via the ICP.

A third positional matching embodiment employs a contour to contour positional matching approach. In one version of the third positional matching embodiment, splines are defined along the bone contours in the 2D body coil images 52 and along the bone contours in the 2D knee coil images 16. In another version of the third positional matching embodiment, the 2D knee coil images 16 are segmented and converted into a 3D bone model 22, and splines are defined along the bone contours in the 2D body coil images 52.

In some versions of the third positional matching embodiment, the splines are generally limited to the bone contours at specific landmarks. In other versions of the third positional matching embodiment, the splines extend along a substantial portion, if not the entirety, of the bone contours. Regardless of which version of the third positional matching embodiment is employed, the splines of the bone contours of the 2D body coil images 52 are positionally matched to bone contours of the 2D knee coil images 16 or the descendent 3D bone model 22 via the ICP algorithm or one of the other above-mentioned transformations. In one version of the third positional matching embodiment, the contours employed exist in both coronal and sagittal image slices.

In a fourth positional matching embodiment, image intensity variations in the 2D knee coil images 16 are identified and positionally matched to corresponding image intensity variations identified in the 2D body coil images 52. For example, image registration techniques are employed that are similar to those described in U.S. patent application Ser. No. 12/386,105, which was filed Apr. 4, 2009, titled System and Method for Image Segmentation in Generating Computer Models of a Joint to Undergo Arthroplasty, and is hereby incorporated by reference into the present application in its entirety. Specifically, a bone 18, 20 in the 2D knee coil images 16 is segmented by a technician. Additionally, a technician may provide an initial approximate transform by specifying one or more landmarks in each of the knee coil and body coil images. The group of the rigid 3D transform with 6 parameters P (3 rotational angle+3 translation parameters) is parameterized. The function to be optimized is defined (see application Ser. No. 12/386,105—local image correlation function F). In one version of the fourth positional matching embodiment, a set of points S is defined in the knee coil images to be used in function F (e.g., the set of points S might be all the voxel points within 3-5 mm distance from the segmentation contours or some subset of such voxel points (e.g., a random subsample of such voxel points)). For every 6-dimensional parameter p in P, transform T(p) is applied to the set S to compute correlation F in the transformed set $f(p)=F(T(p)(S))$. Standard optimization techniques are applied in order to maximize f over parameters p. For example, when a technician provides an initial approximate transform, a gradient descent optimization method may be employed.

As can be understood from the preceding discussion, the various positional matching embodiments may employ a rigid 3D transform that best aligns the femur 18 in the 2D knee coil images 16 to the femur 18 in the 2D body coil images 52. A similar rigid 3D transform may also be employed in the various positional matching embodiments to best align the tibia 20 in the 2D knee coil images 16 to the tibia 20 in the 2D body coil images 52.

A given transform can be applied to the images 16, 52. In other words, a first image can be resampled over the transform. The transformed first image can be overlapped with the second image with the goal of the transform being that the two overlapped images match as close as possible in the region of femur bone. The transform process can be similarly run for the tibia.

While, in some embodiments, the transformed knee coil images and the body coil images may not match precisely because every MRI has a number of its own artifacts that degrade the image differently in different areas, the positional matching will be sufficient to allow the rest of the POP to continue as described herein.

As a general summary, in one embodiment, a few distinguished landmarks in the knee coil images are positional matched to similar or corresponding landmarks in the body coil images. In another embodiment, a larger number of points on the bone boundary in the body coil images are matched to the whole bone boundary (e.g., to the mesh surface in 3D) in the knee coil images. In yet another embodiment, the contours on the bone boundary in the body coil images are matched to the whole boundary of the knee coil images or, alternatively, the descendent 3D bone model. In the yet another embodiment, the image intensity variations around the bone boundary in the body coil images are matched to the image intensity variations in the knee coil images.

Each of embodiments one through three of the positional matching method may be done via a combination of manual and automated methodology or via an entirely automated methodology. The fourth embodiment of the positional matching method may be entirely automated.

As indicated in FIG. 1E in one embodiment, point P is identified in the 2D knee coil images 16 once the 2D knee coil images 16 are positionally matched to the 2D body coil images 52 [Block 140]. In one embodiment, point P may be at the approximate medial-lateral and anterior-posterior center of the patient's knee joint 14. In other embodiments, point P may be at any other location in the 2D knee coil images 16, including anywhere on, near or away from the bones 16, 20 or the joint 14 formed by the bones 18, 20.

As described below with respect to [Blocks 180 and 255] of FIGS. 1G and 1J, respectively, point P may be used to locate the computer generated 3D models 22, 28, 36 created from the 2D knee coil images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D knee images 16.

As indicated in FIG. 1E, the 2D knee coil images 16 are segmented along the bone surface boundaries to generate 2D bone-only contour lines [Block 145]. The 2D knee coil images 16 are also segmented along cartilage and bone surface boundaries to generate 2D bone and cartilage contour lines [Block 245]. In one embodiment, the bone surface contour lines and cartilage-and-bone surface contour lines of the bones 18, 20 depicted in the 2D knee coil image slices 16 may be auto segmented via an image segmentation process as disclosed in U.S. patent application Ser. No. 12/386,105, which was filed Apr. 4, 2009, is titled System and Method for image Segmentation in Generating Computer Models of a Joint to Undergo Arthroplasty, and is hereby incorporated by reference into the present application in its entirety.

At, can be understood from FIG. 1F, the 2D bone-only contour lines segmented from the 2D knee coil images 16 are employed to create computer generated 3D bone-only (i.e., "bone models") 22 of the bones 18, 20 forming the patient's knee 14 [Block 150]. The bone models 22 are located such that point P is at coordinates (X0-j, Y0-j, Z0-j) relative to an origin (X0, Y0, Z0) of the global coordinate system 63. In one embodiment, the bone models 22 incorporate the hip, knee and ankle centers 54, 56, 57, 58, and these centers 54, 56, 58 are positioned so as to reflect their correct respective locations with respect to the orientation and location of the bone models 22. In another embodiment, the hip, knee and ankle centers 54, 56, 57, 58 are not incorporated into the bone models 22, but are linked to the bone models 22 such that the hip, knee and ankle centers 54, 56, 57, 58 may be toggled on or off to display with the bone models 22 or be hidden. In such an embodiment, the hip, knee and ankle centers 54, 56, 57, 58 are positioned so as to reflect their correct respective locations with respect to the orientation and location of the bone models 22 when the centers 54, 56, 57, 58 are toggled on to be visible with the bone models 22.

Regardless of whether the centers 54, 56, 57, 58 are part of the bone models 22 or separate from the bone models 22 but capable of being shown with the bone models 22, the bone models 22 depict the bones 18, 20 in the present deteriorated condition with their respective degenerated joint surfaces 24, 26, which may be a result of osteoarthritis, injury, a combination thereof etc. Also, the hip, knee and ankle centers 54, 56, 57, 58 and bone surfaces 24, 26 are positioned relative to each other as would generally be the case with the patient's long leg anatomy in the present deteriorated state. That the centers 54, 56, 57, 58 are correctly oriented with respect to the bone models 22 to represent the patient's long leg anatomy in the present deteriorated state is made possible, at least in part, via the transformation process described above with respect to [Blocks 125-135] of FIGS. 1D-1E and FIGS. 8-13.

In one embodiment, the systems and methods disclosed herein create the 3D computer generated bone models 22 from the bone-only contour lines segmented from the 2D knee coil images 16 via the systems and methods described in U.S. patent application Ser. No. 12/386,105, which was filed Apr. 4, 2009, is entitled System and Method for image Segmentation in Generating Computer Models of a Joint to Undergo Arthroplasty, and is hereby incorporated by reference into the present application in its entirety. In other embodiments the systems and methods disclosed herein employ any one or more of the following computer programs to create the 3D computer generated bone models 22 from the bone-only contour lines segmented from the 2D knee coil images 16: Analyze from AnalyzeDirect, Inc., Overland Park, Kans.; Insight Toolkit, an open-source software available from the National. Library of Medicine insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1F, the 3D computer generated bone models 22, or associated bone-only contour lines, are utilized to create 3D computer generated "restored bone models" or "planning bone models" 28 wherein the degenerated surfaces 24, 26 are modified or restored to approximately their respective conditions prior to degeneration [Block 155]. Thus, the bones 18, 20 of the restored bone models 28 and their respective restored bone surfaces 24', 26' are reflected in approximately their condition prior to degeneration. The restored bone models 28 are located such that point P is at coordinates (X0-j, Y0-j, Z0-j) relative to the origin (X0, Y0, Z0) of the global coordinate system 63. Thus, the restored bone models 28 share the same orientation and positioning relative to the origin (X0, Y0, Z0) of the global coordinate system 63 as the bone models 22.

As with the bone models 22 discussed above, the hip, knee and ankle centers 54, 56, 57, 58 may be incorporated into the restored bone models 28 or stored separately from the restored bone models 28, but capable of being toggled on or off to be displayed relative to the restored bone models 28 or hidden.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the above-described bone restoration process is generally or completely automated, as disclosed in U.S. patent application Ser. No. 12/111,924 to Park, which is titled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description. In other words, a computer program may analyze the bone models 22 and their degenerated surfaces 24, 26 to determine how and to what extent, the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1F, once the restored bone models 28 have been generated as discussed above with respect to [Block 155], the restored bone models 28 are employed in a pre-operative planning ("POP") procedure to determine saw cut (bone resection) locations 30 and drill hole locations 32 in the patient's bones that will allow the arthroplasty joint implants to generally restore the patient's joint line to its pre-degenerative alignment. Specifically, the POP process begins by moving the restored bone models 28 to the location of 3D models 34 of arthroplasty implant models proposed for use in the actual arthroplasty procedure [Block 160]. In moving the restored bone models 28 to the implant models 34, point p on the restored bone models 28 moves from coordinates (X0-j, Y0-j, Z0-j) to coordinates (X0-k, Y0-k, Z0-k) and becoming point P'. The implant models 34 include planar surfaces representative of the planar surfaces of the actual implants that intersect resected bone surfaces. These planar surfaces of the implant models 34 are used to determine resection or saw cut locations 30 during the POP. Also, the implant models 34 include screw holes representative of the screw holes of the actual implants that hold bone screws for retaining the actual implant in place on the resected bone. These holes of the implant models 34 are used to determine drill hole locations 32 during POP.

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. As can be understood from FIG. 1G, by superimposing the implant models 34 over the restored bone models 28, or vice versa, the joint surfaces of the implant models 34 can be aligned, shape fit, or otherwise caused to correspond with the joint surfaces of the restored bone models 28 [Block 165]. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. In one embodiment, the above-described POP process is generally or completely automated, as disclosed in U.S. patent application Ser. No. 12/563,809 to Park, which is titled Arthroplasty. System and Related Methods, was filed Sep. 21, 2009 and is incorporated by reference in its entirety into this Detailed Description. In other words, a computer program may manipulate computer generated 3D implant models 34 femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' (X0-k, Y0-k, Z0-k) relative to the origin (X0, Y0, Z0) of the global coordinate system 63, and the restored bone models 28 are located at point P (X0-j, Y0-j, Z0-j). To cause the joint surfaces of the models 28, 34 to correspond, the computer program may move the restored bone models 28 from point P (X0-j, Y0-j, Z0-j) to point P' (X0-k, Y0-k, Z0-k), or vice versa [Block 160]. Once the joint surfaces of the models 28, 34 are in close proximity, the joint surfaces of the implant models 34 may be shape-matched to align or correspond with the joint surfaces of the restored bone models 28 [Block 165]. By causing the joint surfaces of the models 28, 34 to so align, the implant models 34 are positioned relative to the restored bone models 28 such that the saw cut locations 30 and drill hole locations 32 can be determined relative to the restored bone models 26. As a result of this POP process, the resection locations 30 will be such that the actual implants will generally restore the patient's knee geometry to what it was prior to degeneration.

As depicted in FIG. 1G, in one embodiment, a joint gap analysis is conducted to adjust orientation of the restored bone models 28 and arthroplasty, implant models 34 so the joint gap on each side of joint is generally equal, causing the joint line 64 to be generally parallel to floor and generally representative of the patient's pre-degenerative joint line 64 [Block 170]. Further detail regarding the joint gap analysis is provided in U.S. patent application Ser. No. 12/563,809 to Park, which is titled Arthroplasty System and Related Methods, was filed Sep. 21, 2009 and is incorporated by reference in its entirety into this Detailed Description.

As indicated in FIG. 1G, once the POP process is completed, a determination is made regarding the 3D location and/or orientation impact on the hip, knee and ankle center points 54, 56, 57, 58 on account of any of the processes of [Blocks 160, 165 & 170] or any other position and/or orientation change to the bone models 22 or restored bone models 28 [Block 175]. As discussed above with respect to [Block 135] of FIG. 1E, the location and orientation relationships between the hip, knee and ankle centers 54, 56, 57, 58 and the knee coil 2D images 16 are established. These location and orientation relationships between the hip, knee and ankle centers 54, 56, 57, 58 and the knee coil 2D images 16 and the descendant 3D bone models 22, 28 of the knee coil 2D images 16 are maintained throughout the various processes described herein. Thus, as indicated in FIG. 1C, the X, Y and Z global coordinate locations and/or orientations of each of the center points 54, 56, 57, 58 in "Table A" of [Block 115] are updated for any 3D location and/or orientation impact on the center points 54, 56, 57, 58 on account of any of the processes of [Blocks 160, 165 & 170] or any other location and/or orientation change to the 3D bone models 22 or restored bone models 28 [Block 120].

For example, after the joint gap analysis and manipulation is complete as recited in [Block 170], the coordinates for the joint centers of the restored 3D knee model are changed from (x'2, y'2, z'2) because of the manipulation of the models 28, 34 in bringing the joint line parallel to the ground. After completion of the joint gap analysis and manipulation, the joint line 64 is set up and is perpendicular to the center of distal femur and perpendicular to the center of proximal tibia. Such manipulation can be done for both the distal femur and proximal tibia. As a result, the coordinates of the joint centers of this newly aligned 3D knee model (with joint line references and joint center points) may be further identified and recorded as (x"2, y"2, z"2).

As indicated in FIG. 1G, once the POP process is completed, a determination is made regarding the change in the 3D location and/or orientation of the bone models 22 or restored bone models 28 on account of any of the processes of [blocks 160, 165, 170] or any other location and/or orientation change to the bone models 22 or restored bone models 28 [Block 180]. Such a determination is employed to update the location and orientation of the arthritic models 36, as discussed below in [Block 255] of FIG. 1J.

As illustrated in FIG. 1H, the hip, knee and ankle center points 54, 56, 57, 58 and femoral mechanical axis 68, tibial mechanical axis 70, and mechanical axis 72 are depicted in 3D with the 3D restored bone models 28 and 3D implant models 34 [Block 190]. This may be achieved where the center points 54, 56, 57, 58 are part of the 3D restored bone models 28 or the center points are separate from the restored bone models 28, but capable of being toggled on to be viewable in 3D with the restored bone models 2$. The points 54, 56, 57, 58, axes 68, 70, 72, and models 28, 34 are presented in a coronal view [Block 190]. By employing the restored bone models 28 in the POP process and maintaining the proper location and orientation of the hip, knee and ankle centers 54, 56, 57, 58 during the POP process, the models 28, 34 and centers 54, 56, 57, 58 illustrate a general approximation of the patient's knee geometry prior to deterioration, both respect to the joint line 64 and the various axes 68m, 70, 72.

Figure 17:
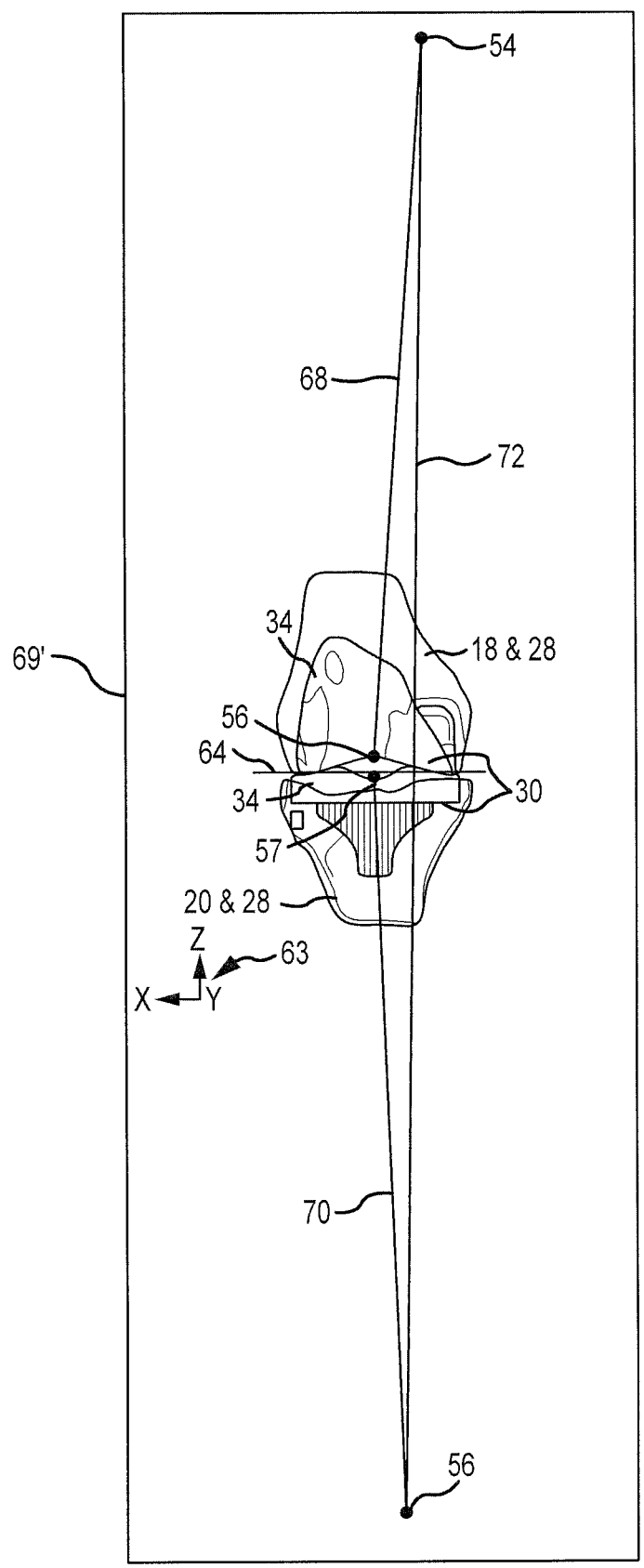
FIG. 17 is a coronal snapshot of the restored bone models, the implant models, the joint center points, and the femur mechanical axis, the tibia mechanical axis and the mechanical axis.

In one embodiment, a 2D coronal snapshot 69' of the models 28, 34, points 54, 56, 57, 58, and axes 68, 70, 72 is created [Block 195]. An example of such a coronal snapshot 69' is depicted in FIG. 17. Also, in one embodiment, a 2D coronal snapshot 69" of the models 28, points 54, 56, 57, 58, and axes 68, 70, 72, less the implant models 34, is created [Block 200]. Each of these snapshots 69', 69" depict the patient's joint geometry in natural alignment or, in other words, as the patient's joint geometry is believed to have generally existed prior to degeneration.

Figure 19:
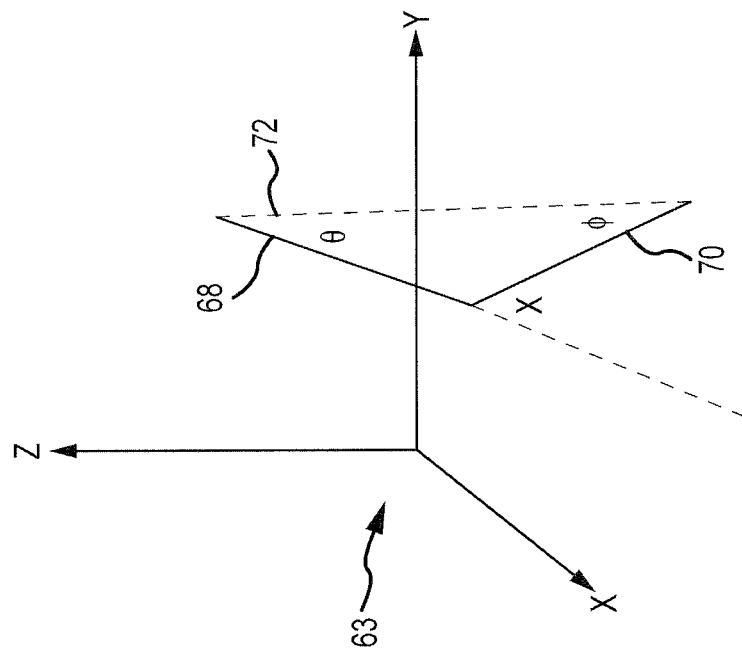
FIG. 19 is a diagrammatic depiction of the axes and their relationship to each other in the global coordinate system.
Figure 18:
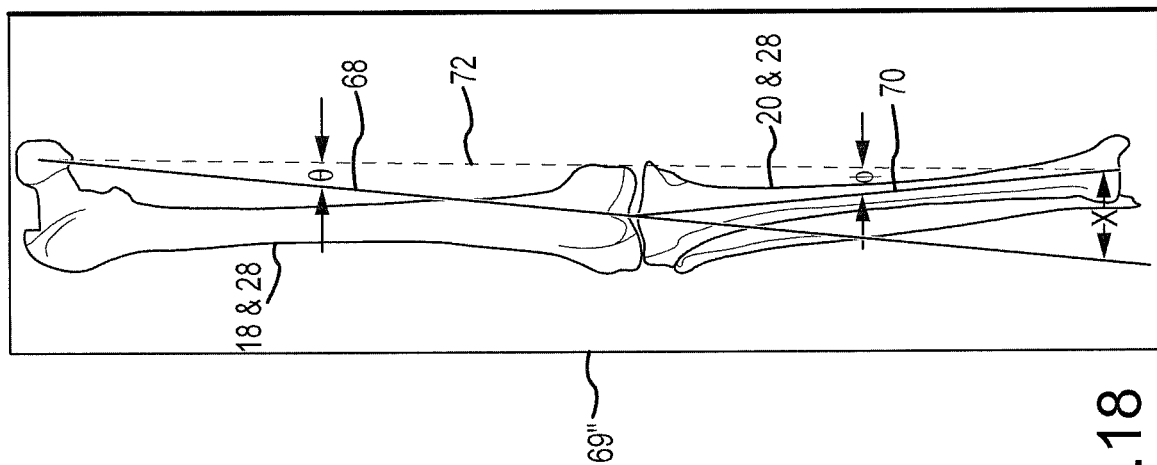
FIG. 18 is another version of the 2D coronal snapshot that may be provided to the physician.

FIG. 18 is another version of the 2D coronal snapshot 69" that may be provided to the physician, and FIG. 19 is a diagrammatic depiction of the axes 68, 70, 72 and their relationship to each other in the global coordinate system 63. The snapshot 69", which illustrates the natural alignment knee geometry and depicts the varus/valgus ("v/v") measurement, may be employed by the physician to determine the amount of correction needed to bring the knee geometry to a neutral geometry or a geometry between natural and neutral the physician considers desirable.

As shown in FIGS. 18 and 19, the v/v angle θ for the femur 18 is measured between the FMA 68 and MA 72. The FMA 68 is a line extending between the center of the femoral head to the center of the knee region of the femur 18. The v/v angle φ for the tibia 20 is measured between the TMA 70 and the MA 72. The TMA 70 is a line extending between the center of the ankle to the center of the knee region of the tibia 20. The MA 72 is a line extending between the center of the femoral head to the center of the ankle. When the knee geometry is in a zero degree mechanical axis or neutral geometry, the FMA 68, TMA 70 and MA 72 will be generally coextensively aligned with each other.

In one embodiment, if the v/v angles fall into an acceptable range wherein θ, φ<±3°, then the snapshot 69''' has an acceptable natural geometry and can be forwarded to the physician. If the v/v angles do not fall into an acceptable range wherein θ, φ<±3°, then the POP process is run again to arrive: at a natural geometry that is acceptable.

As shown in FIGS. 18 and 19, the angle X approximately equal to the sum of angles θ and φ.

As indicated in FIG. 1I, in one embodiment, one more of the 2D coronal snapshots 69', 69", 69''' are provided to the physician for review [Block 205]. The physician reviews the proposed correction and associated natural alignment depicted in the received snapshot(s) 69', 69", 69''' and provides feedback regarding the proposed correction [Block 210]. If the physician approves of the proposed correction and associated natural alignment depicted in the received snapshot(s) 69', 69", 69''' [Block 215], then the proposed correction is left as is [Block 235].

However, as can be understood from FIG. 1I, if the physician disapproves of the proposed correction and associated natural alignment depicted in the received snapshot(s) 69', 69" [Block 215], then the proposed correction and associated natural alignment is adjusted in the X-Y (coronal) plane according to physician input [Block 225], the adjustment being made to the saw cut and drill hole locations 30, 32 of the 3D models 28, 34 of [Block 170]. In other words, the proposed correction and associated natural alignment is adjusted to a new proposed correction, wherein the new proposed correction is associated with a zero degree mechanical axis (neutral) alignment or an alignment somewhere between the originally proposed natural alignment and a neutral alignment.

Figure 20:
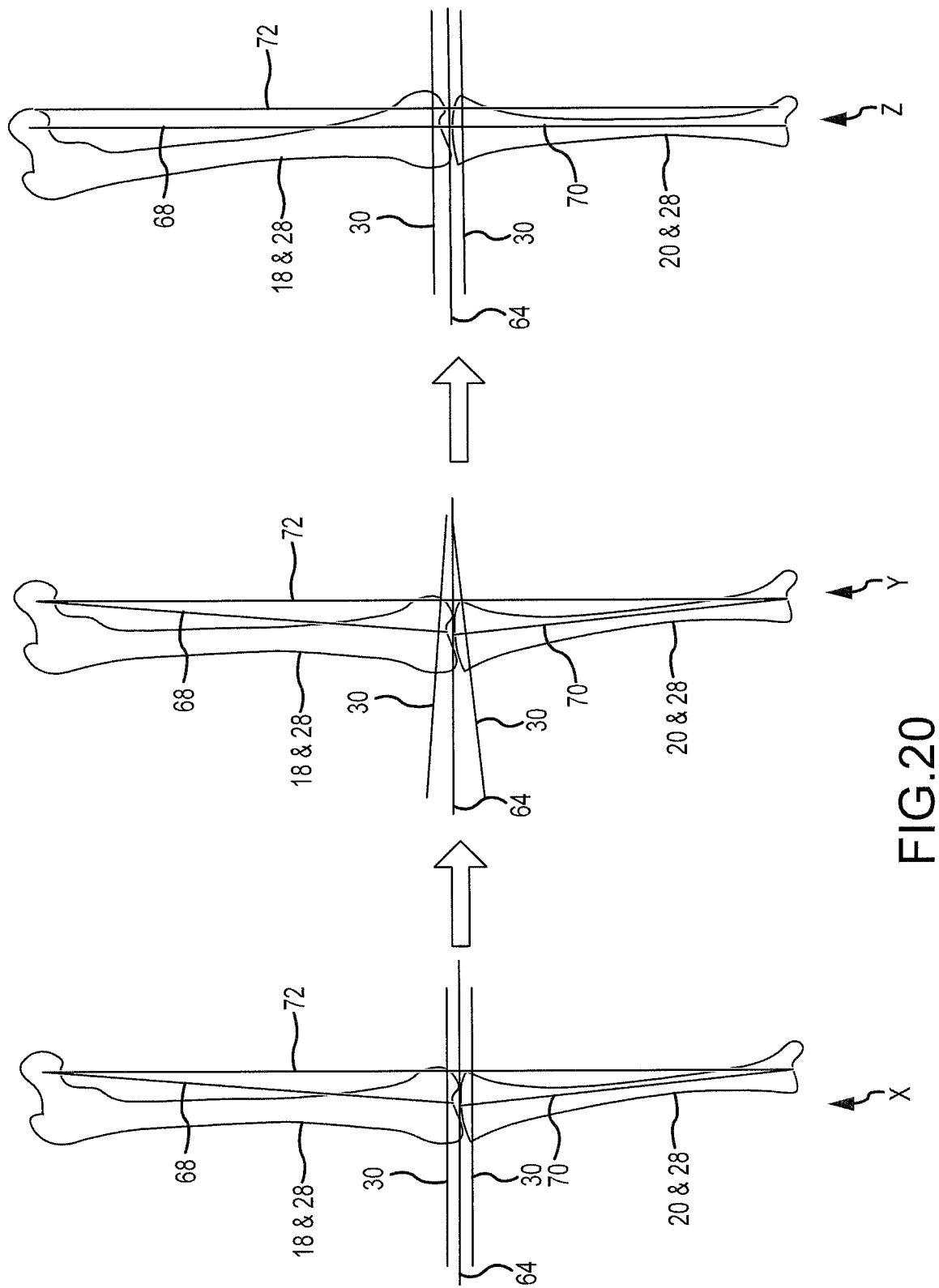
FIG. 20 is a diagrammatic depiction of a process of adjusting resection lines based on joint geometry information conveyed via the 2D coronal snapshots.

As can be understood from FIG. 20, which is a diagrammatic depiction of a process of adjusting resection lines based on joint geometry information conveyed via the 2D coronal snapshots 69', 69", 69''', the knee joint geometry is depicted in natural alignment at X, the joint line 64 being generally parallel to the ground and the FMA 68 and TMA 70 being angled relative to the MA 72. Upon review, the physician may determine the resection lines 30 in image X should be adjusted to be as indicated in images Y to cause the knee joint geometry to assume an alignment that is closer to neutral. As shown in image Z, where the resection lines 30 have been adjusted per the physician's direction and the bones 18, 20 realigned, the joint line 64 is generally parallel to the floor and the FMA 68 and TMA 70 are generally parallel to the MA 72, which is shown off of the bones 18, 20 for clarity purposes.

Thus, in summary of the events at [Block 215] of FIG. 1I, the physician may determine that the natural alignment is desirable and, as a result, the alignment of the restored bone model 28 is not changed [Block 235], or the physician may determine that the restored bone model 28 should be realigned from natural alignment to an alignment that is closer to zero degree mechanical axis [Block 225].

If the alignment is updated as in [Block 225], then per [Block 230], the 2D coronal snapshots 69', 69" of [Blocks 195 and 200] are regenerated off of the models 28, 34 of [Block 170] as updated per [Block 225]. The updated coronal snapshots 69', 69" are again sent to the physician [Block 205] and the process repeats itself as recited above with respect to [Blocks 210-230], until the physician agrees with the proposed correction [Block 215] and the proposed correction is found to be desirable, no further correction being deemed necessary by the physician [Block 235].

As indicated in FIG. 1K, in one embodiment, the data 44 regarding the saw cut and drill hole locations 30, 32 relative to point P' (X0–k, Y0–k, Z0–k) is packaged or consolidated as the "saw cut and drill hole data" 44 [Block 240]. The "saw cut and drill hole data" 44 is then used as discussed below with respect to [Block 270] in FIG. 1K.

As mentioned above with respect to FIG. 1E, the 2D knee coil images 16 are segmented along cartilage and bone boundaries to generate 2D bone and cartilage contour lines [Block 245]. As can be understood from FIG. 1J, the bone and cartilage contour lines are used to create computer generated 3D bone and cartilage models (i.e., "arthritic models") 36 of the bones 18, 20 forming the patient's joint 14 [Block 250]. Like the above-discussed bone models 22, the arthritic models 36 are located such that point P is at coordinates (X0–j, Y0–j, Z0–j) relative to the origin (X0, Y0, Z0) of the global coordinate system 63 [Block 190]. Thus, the bone and arthritic models 22, 36 share the same location and orientation relative to the origin (X0, Y0, Z0) of the global coordinate system 63. This position/orientation relationship is generally maintained throughout the process discussed with respect to FIGS. 1E-1K. Accordingly, reorientations or movements relative to the origin (X0, Y0, Z0) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, 20 in the present deteriorated condition with their respective degenerated joint surfaces 24, 26, Which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1J and already mentioned above, to coordinate the positions/orientations of the bone and arthritic models 22, 36 and their respective descendants, any reorientation or movement of the restored bone models 28 from point P to point P''' is tracked to cause a generally identical displacement for the "arthritic models" 36 [Block 255]. Thus, for any change in the 3D position or orientation of the bone models 22 or restored bone models 28 on account of any of the processes of [Blocks 160, 165, 170] or any other position or orientation change to the bone models 22 or restored bone models 28 (e.g., the bone models 22 or restored bone models 28 being reoriented at or moved from point P at coordinates (X0-j, Y0-j, Z0-j) to point P' at coordinates (X0-k, Y0-k, Z0-k)), an identical movement is caused in the 3D arthritic models 36 such that the location and orientation of arthritic models 36 match those of the bone models 22 and restored bone models 28.

As depicted in FIG. 1J, computer generated 3D surface models 40 of the arthroplasty target areas 42 of the arthritic models 36 are imported into computer generated 3D arthroplasty jig models 38 [Block 260]. Thus, the jig models 38 are configured or indexed to matingly (matchingly) receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly (matchingly) receive the arthroplasty target areas 42 of the arthritic models 36. Point P' (X0–k, Y0–k, Z0–k) can also be imported into the jig models 38, resulting in jig models 38 positioned and oriented relative to point P' (X0–k, Y0–k, Z0–k) to allow their integration with the bone cut and drill hole data 44 of [Block 240].

In one embodiment, the procedure for indexing the jig models 38 to the arthroplasty target areas 42 is generally or completely automated, as disclosed in U.S. patent application Ser. No. 11/959,344 to Park, which is titled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' (X0–k, Y0–k, Z0–k) into the jig models 38, resulting in the jig models 38 being indexed to matingly receive the arthroplasty target areas 42 of the arthritic models 36. The resulting jig models 38 are also positioned and oriented relative to point P' (X0–k, Y0–k, Z0–k) to allow their integration with the bone cut and drill hole data 44 of [Block 240].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is titled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 1K, in one embodiment, the data regarding the jig models 38 and surface models 40 relative to point P' (X0–k, Y0–k, Z0–k) is packaged or consolidated as the "jig data" 46 [Block 265]. The "jig data" 46 is then used as discussed below with respect to [Block 270] in FIG. 1K.

As can be understood from FIG. 1K, the "saw cut and drill hole data" 44 is integrated with the "jig data" 46 to result in the "integrated jig data" 48 [Block 270]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to achieve a joint alignment that is: (1) generally representative of the patient's pre-degenerative joint line (i.e., natural alignment); generally corresponding to a zero mechanical axis alignment; or (3) somewhere between (1) and (2), depending the input the physician provided in the process discussed above with respect in FIG. 1I.

As can be understood from FIGS. 1A and 1K, the "integrated jig data" 48 is transferred from the computer 6 to the CNC machine 10 [Block 275]. Jig blanks 50 are provided to the CNC machine 10 [Block 280], and the CNC machine 10 employs the "integrated jig data" to machine the arthroplasty jigs 2 from the jig blanks 50 [Block 285].

Figure 2A:
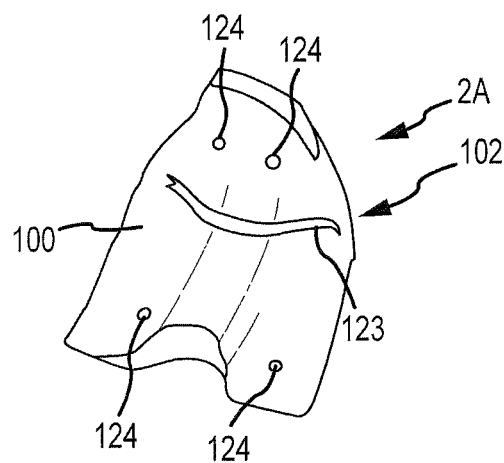
FIGS. 2A and 2B are, respectively, bottom and top perspective views of an example customized arthroplasty femur jig.
Figure 3A:
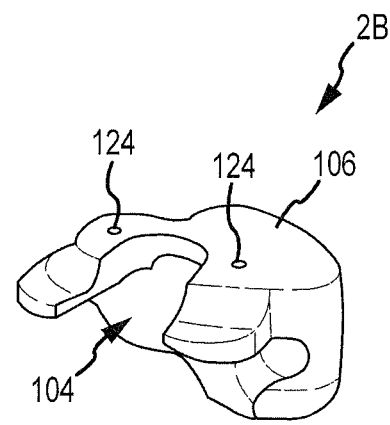
FIGS. 3A and 3B are, respectively, bottom and top perspective views of an example customized arthroplasty tibia jig.
Figure 2B:
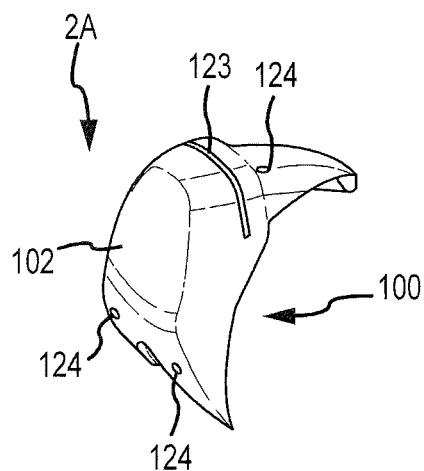
Figure 3B:
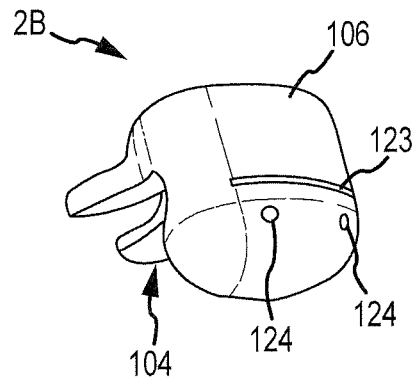

For a discussion of example customized arthroplasty cutting jigs 2 capable of being manufactured via the above-discussed process, reference is made to FIGS. 2A-3B. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 2A-3B are for total knee replacement ("TKR" or partial knee ("uni-knee") replacement procedures. Thus, FIGS. 2A and 2B are, respectively, bottom and top perspective views of an example customized arthroplasty femur jig 2A, and FIGS. 3A and 3B are, respectively, bottom and top perspective views of an example customized arthroplasty tibia jig 2B.

As indicated in FIGS. 2A and 2B, a femur arthroplasty jig 2A may include an interior side or portion 100 and an exterior side or portion 102. When the femur cutting jig 2A is used in a TKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR surgery, the surfaces of the target area 42 and the interior portion 100 match. In other words, the surface of the interior portion 100 of the femur jig 2A is generally a negative of the target area 42 of the patient's femur 18 and will matingly or matchingly receive the target area 42.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 3A and 3B, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match. In other words, the surface of the interior portion 104 of the tibia jig 2B is generally a negative of the target area 42 of the patient's tibia 20 and will matingly or matchingly receive the target area 42.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

Another embodiment of the methods and systems for manufacturing the jigs 2A, 2B will now be described, the another embodiment having a shorthand designation of "MA alignment", wherein the embodiment described above with respect to FIGS. 1A-20 can have a shorthand designation of "natural alignment". The MA alignment embodiment is configured to provide a post-surgical joint alignment that is generally a zero mechanical axis alignment. For the MA alignment embodiment, the methods and systems for manufacturing the jigs 2A, 2B are generally the same as described above with respect to the natural alignment embodiment, except the POP for the MA alignment embodiment does not first calculate a post-surgical joint alignment that is (1) generally representative of the patient's pre-degenerative joint line and then allowing the surgeon to keep such an alignment or modify the alignment to correspond (2) generally to a zero mechanical axis alignment or (3) an alignment that is somewhere between (1) and (2). Instead, the MA alignment embodiment has POP that first achieves a post-surgical joint alignment that is generally representative of a zero mechanical axis alignment and then allows the surgeon to keep such an alignment or modify the alignment as desired.

The MA alignment embodiment begins by following generally the same process as described above with respect to FIGS. 1A-IE, arriving at Block 145 and Block 245 of FIG. 1E, wherein the knee coil 2D images 16 are segmented along bone boundaries to generate 2D bone-only contour lines [Block 145] and segmented along cartilage and bone boundaries to generate 2D bone and cartilage contour lines [Block 245]. As can be understood from FIGS. 1F and 1J, the 2D bone-only contour lines are then used to generate the 3D bone models (i.e., planning models) 22 [Block 150], and the 2D bone and cartilage contour lines are used to generate the 3D bone and cartilage models (i.e., arthritic models) 36 [Block 250]. Before being used to generate the 3D arthritic models 36, the 2D bone and cartilage contour lines generated during Block 245 are subjected to an overestimation process as disclosed in U.S. Non-Provisional patent application Ser. No. 12/505,056, which is titled System and Method for Manufacturing Arthroplasty Jigs Having Improved Mating Accuracy, was flied by Park Jul. 17, 2009, and is hereby incorporated by reference in its entirety into this Detailed Description.

Figure 21:
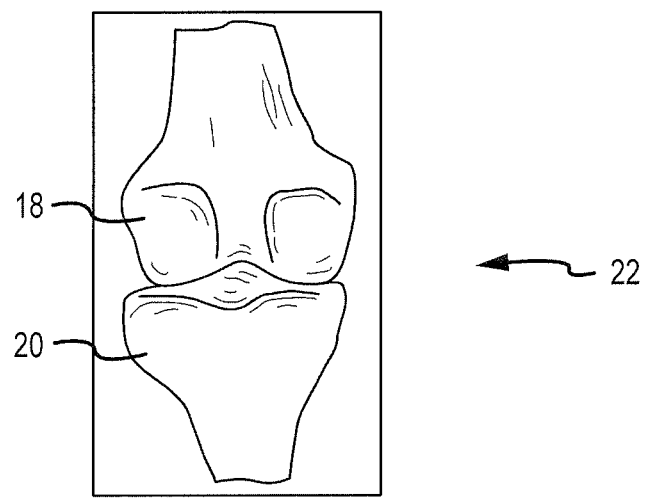
FIG. 21 is coronal view of 3D planning or bone models.
Figure 22:
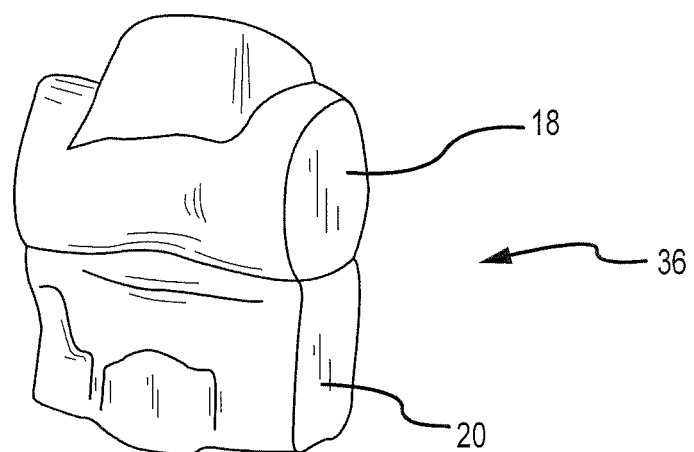
FIG. 22 is a coronal-sagittal isometric view of 3D overestimated arthritic models.

FIG. 21 shows an example of 3D bone models 22 resulting from the 2D bone-only contour lines. FIG. 22 shows an example of the 3D arthritic models 36 resulting from the overestimated 2D bone and cartilage contour lines. Due to the overestimation process applied to the bone and cartilage contour lines, surfaces of the arthritic models 36 are overestimated (i.e., pushed outwardly from the interior of the model 36) in regions of the model 36 that correspond to (1) regions of the images that are associated with low accuracy due to limitations in the imaging processes or (2) regions of the model that are unlikely to be manufactured accurately into a jig blank due to limitations of, for example, the milling process.

Figure 23:
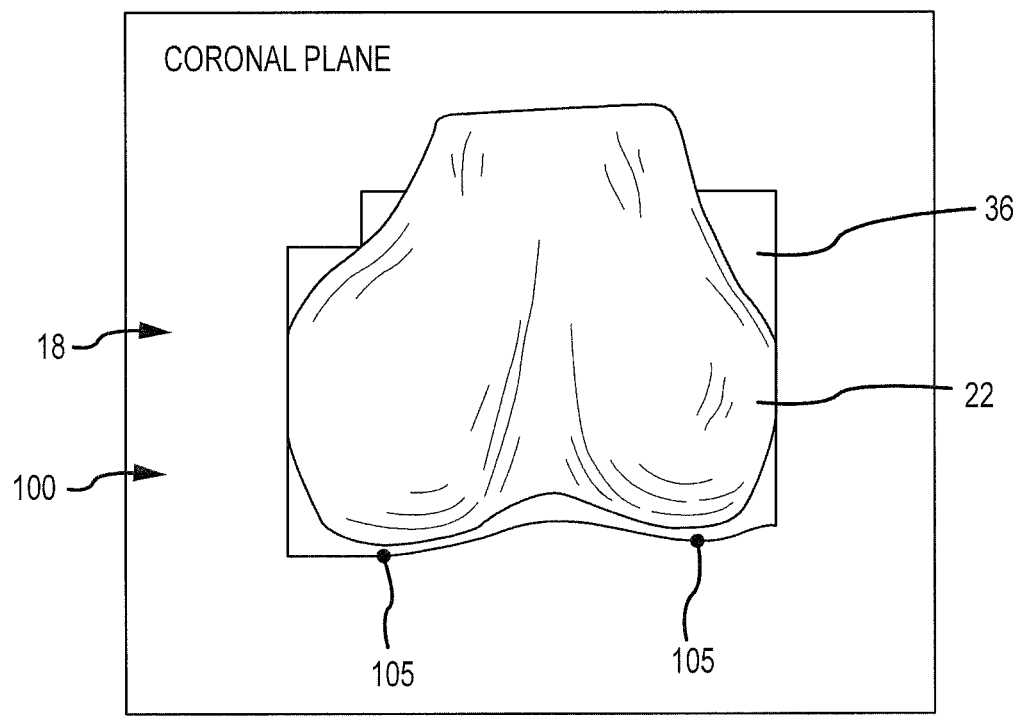
FIG. 23 is a coronal view of a 3D femoral superimposed model formed of the 3D femoral bone and overestimated arthritic models superimposed.
Figure 24:
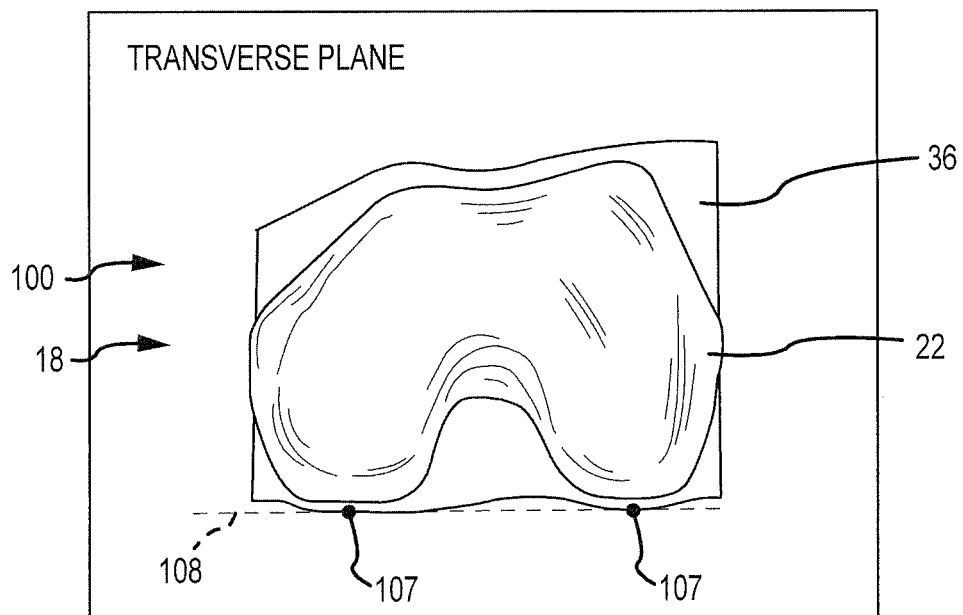
FIG. 24 is an axial view of the 3D femoral superimposed model of FIG. 23.

As can be understood from FIGS. 23 and 24, which are, respectively, coronal and axial views of the models 22, 36 of the femur 18, the femoral models 22, 36 are superimposed to begin the POP process of the MA alignment embodiment. Similarly, as can be understood from FIGS. 25 and 26, which are, respectively, coronal and axial views of the models 22, 36 of the tibia 20, the tibial models 22, 36 are superimposed to begin the POP process of the MA alignment embodiment. In other words, POP for the MA alignment embodiment employs both the bone models 22 and the arthritic models 36. The bone models 22 identify the cortical and subchondral bone boundaries, and the arthritic models 36 identify the cartilage boundaries. By employing both types of models 22, 36, the full definition of the knee anatomy is achieved with distinct cartilage and bony anatomical landmarks for the femur 18 and tibia 20. From here on in this discussion regarding the MA alignment embodiment, the models 22, 26 when superimposed together for purposes of POP will be referred to as superimposed models 100.

As indicated in FIG. 23, a most distal femoral condylar point 105 is identified on each of the condyles of the femoral arthritic model 36 of the femoral superimposed model 100. Similarly, as indicated in FIG. 24, a most posterior point 107 is identified on each of the condyles of the femoral arthritic model 36 of the femoral superimposed model 100. A posterior condylar line 108 connects the most posterior condylar points 107.

Figure 25:
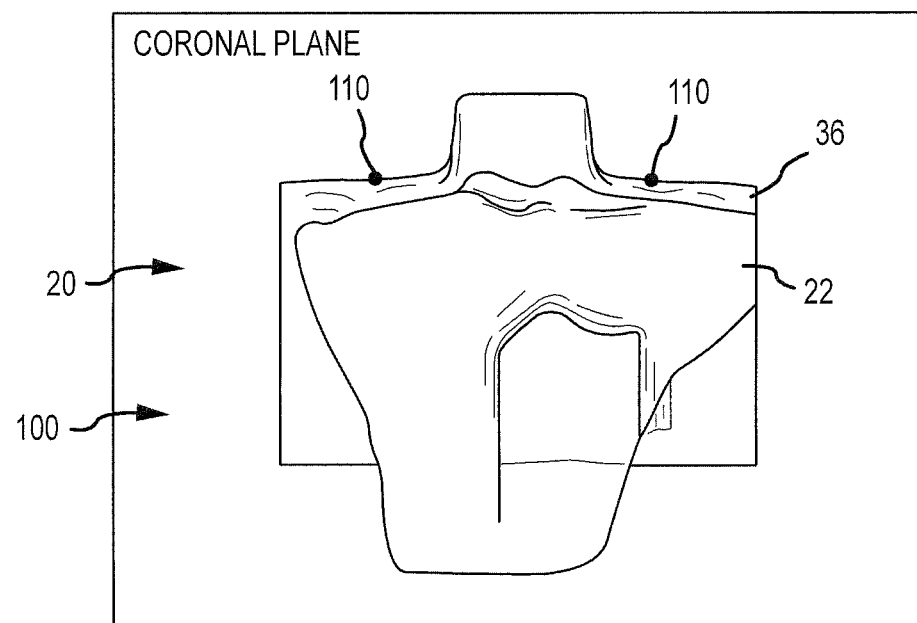
FIG. 25 is a coronal view of a 3D tibial superimposed model formed of the 3D tibial bone and overestimated arthritic models superimposed.
Figure 26:
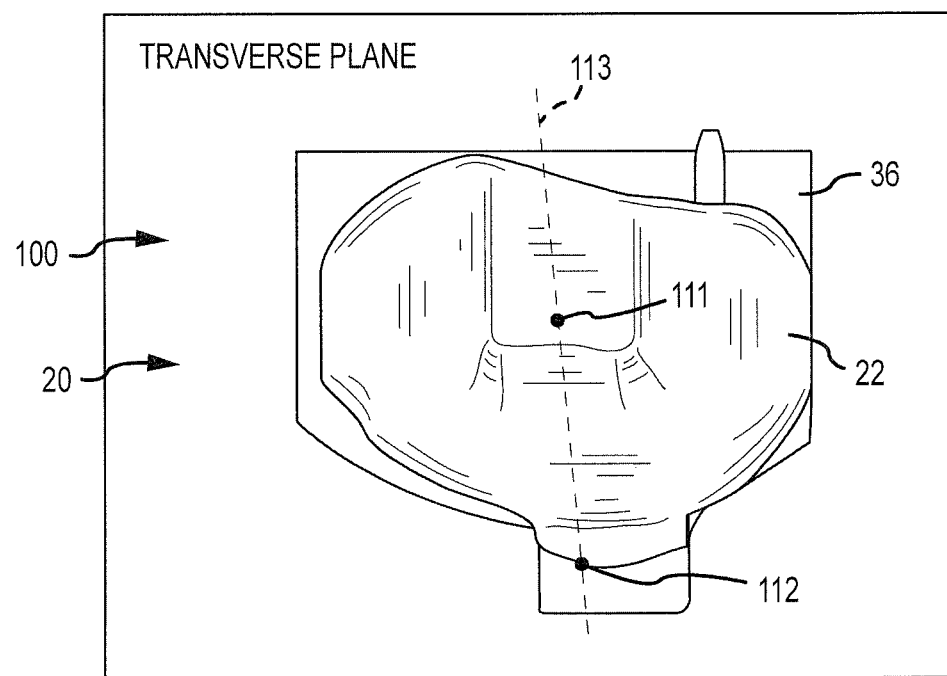
FIG. 26 is an axial view of the 3D tibial superimposed model of FIG. 25.

As indicated in FIG. 25, a most proximal tibial condylar point 110 is identified on each of the condyles of the tibial arthritic model 36 of the tibial superimposed model 100. As indicated in FIG. 26, a center point 111 of the tibial plateau and a point 112 at the medial third of the tibial tuberosity are identified on the bone model 22 of the femoral tibial superimposed model 100. A rotational tibial reference line 113 connects the points 111 and 112.

Figure 1L:
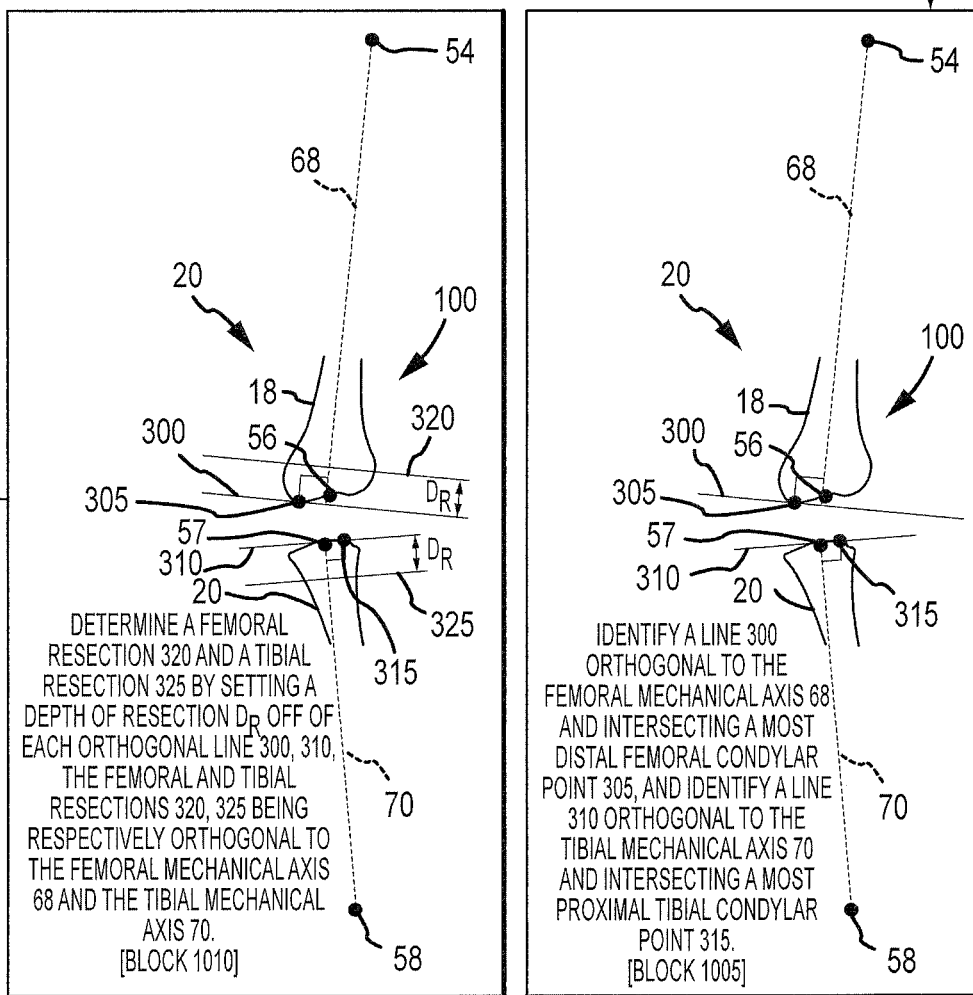
FIGS. 1L-1M are flow chart diagrams outlining an alternative embodiment of a portion of the jig production method disclosed herein.

As can be understood from FIG. 1L, the hip, knee and ankle center points 54, 56, 57, 58 and the femoral mechanical axis 68, tibial mechanical axis 70 and mechanical axis 72 are depicted in 3D with the 3D superimposed models 100 presented in a coronal view [Block 1000]. The center points 54, 56, 57 and 58 are obtained and positionally referenced to the models 100 as discussed above with respect to FIGS. 1A-1E.

As can be understood from FIG. 1L, a most distal point 305 of the two distal femoral condylar points 105 identified in FIG. 23 is identified, and a line 300 orthogonal to the femoral mechanical axis 68 and intersecting the most distal femoral condylar point 305 is provided [Block 1005]. Similarly, a most proximal point 315 of the two proximal tibial condylar points 110 identified in FIG. 25 is identified, and a line 310 orthogonal to the tibial mechanical axis 70 and intersecting the most proximal tibial condylar point 305 is provided [Block 1005].

As indicated in FIG. 1L, a femoral resection plane 320 and a tibial resection plane 325 are determined by setting a depth of resection DR off of each orthogonal line 300, 310, the femoral and tibial resection planes 320, 325 being respectively orthogonal to the femoral mechanical axis 68 and the tibial mechanical axis 70 in the coronal view [Block 1010]. The superior/inferior translation is now established for the POP.

In one embodiment, the depth of resection DR for the femur may be approximately 8 mm, plus or minus 1-3 mm depending on the depth of the implant intended to be implanted. For example, the depth of resection DR for the femur may be based on the thickness of the femoral implant form the most distal point of the medial or lateral condyle to the other side of the flange.

In one embodiment, the depth of resection DR for the tibia may be approximately 11 mm, plus or minus 1-3 mm depending on the depth of the implant intended to be implanted. For example, the depth of resection DR for the tibia may be based on the thickness of the tibia implant form the most proximal point of the medial or lateral condyle to the other side of the base plate and its liner.

Figure 27:
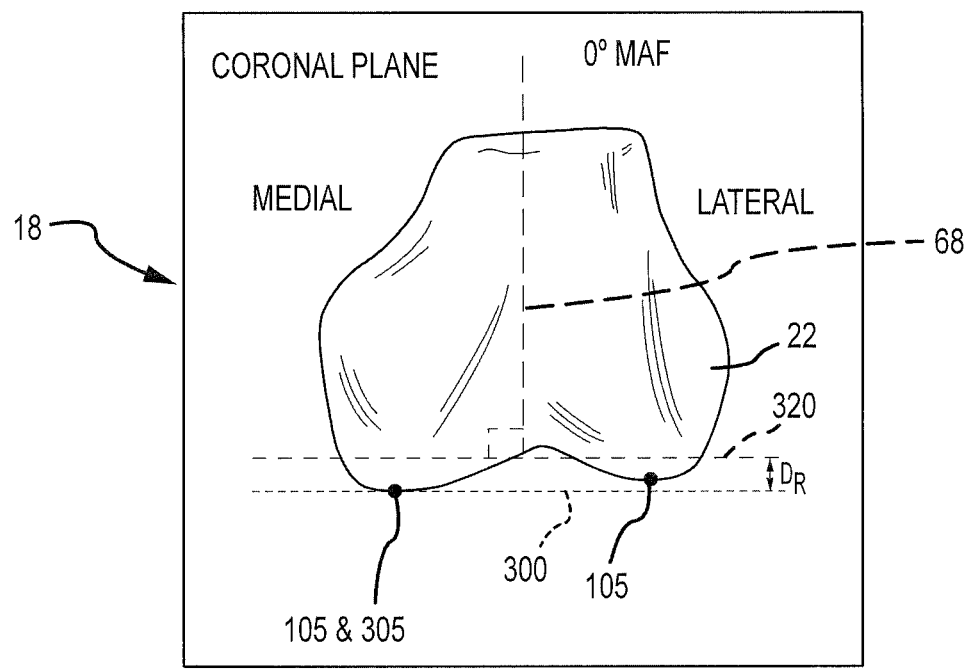
FIG. 27 is a coronal view of the 3D femoral bone model with the superior/inferior depth of resection depicted to achieve the desired varus/valgus resection orientation.
Figure 28:
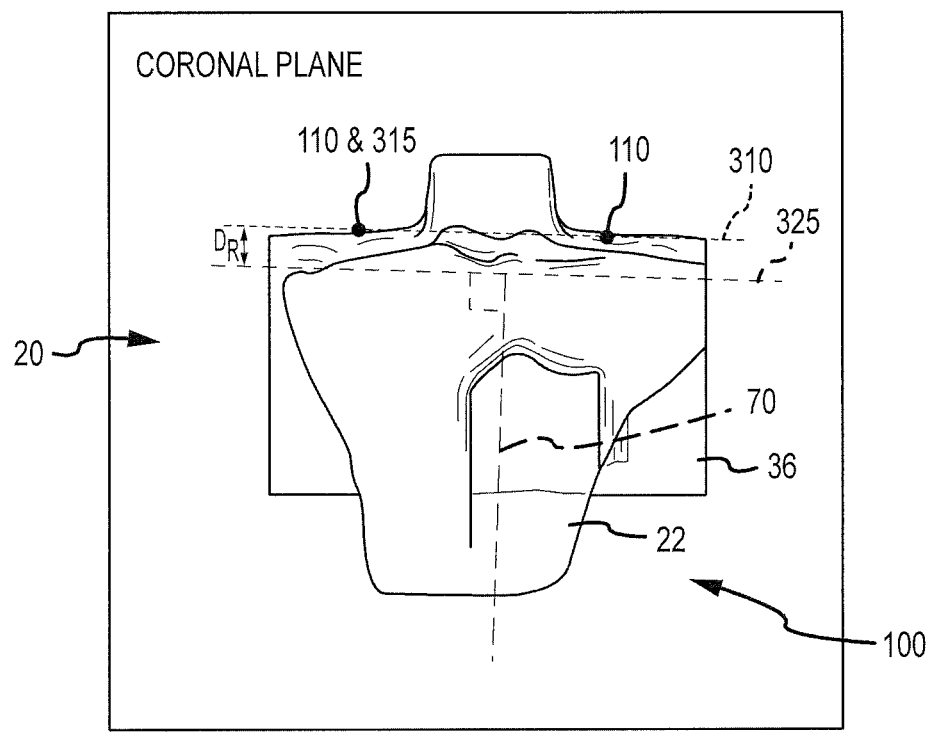
FIG. 28 is a coronal view of the 3D tibial superimposed model (i.e., 3D tibial bone model superimposed with the 3D tibial arthritic model) with the superior/inferior depth of resection depicted to achieve the desired varus/valgus resection orientation.

FIG. 27 is an enlarged coronal view of the femoral bone model 22 illustrating the results of the operations of Blocks 1000-1010 in FIG. 1L with respect to the femur 18. FIG. 28 is an enlarged coronal view of the tibial superimposed model 100 illustrating the results of the operations of Blocks 1000-1010 in FIG. 1L with respect to the tibia 18.

Figure 29:
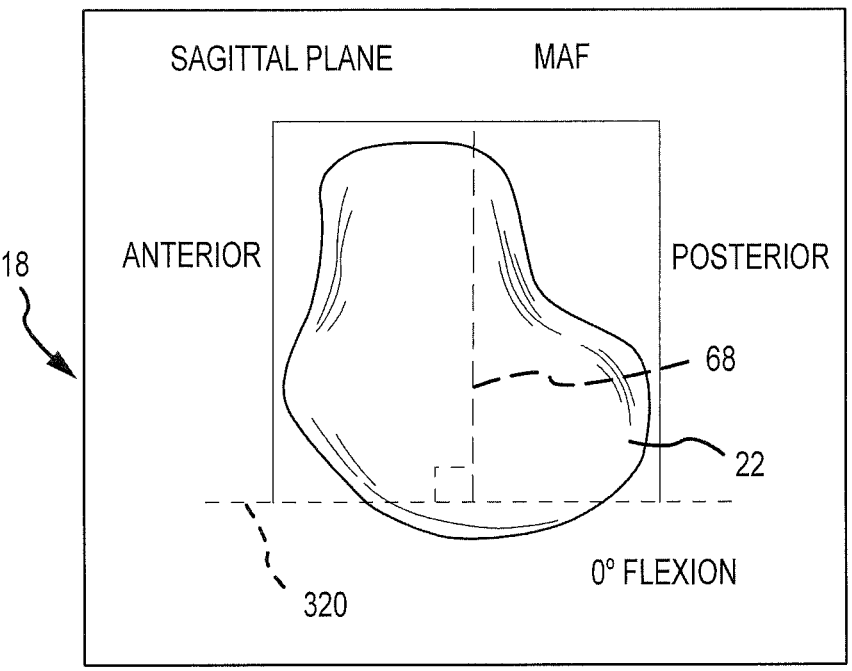
FIG. 29 is a sagittal view of the 3D femoral bone model with the flexion/extension orientation depicted.
Figure 30:
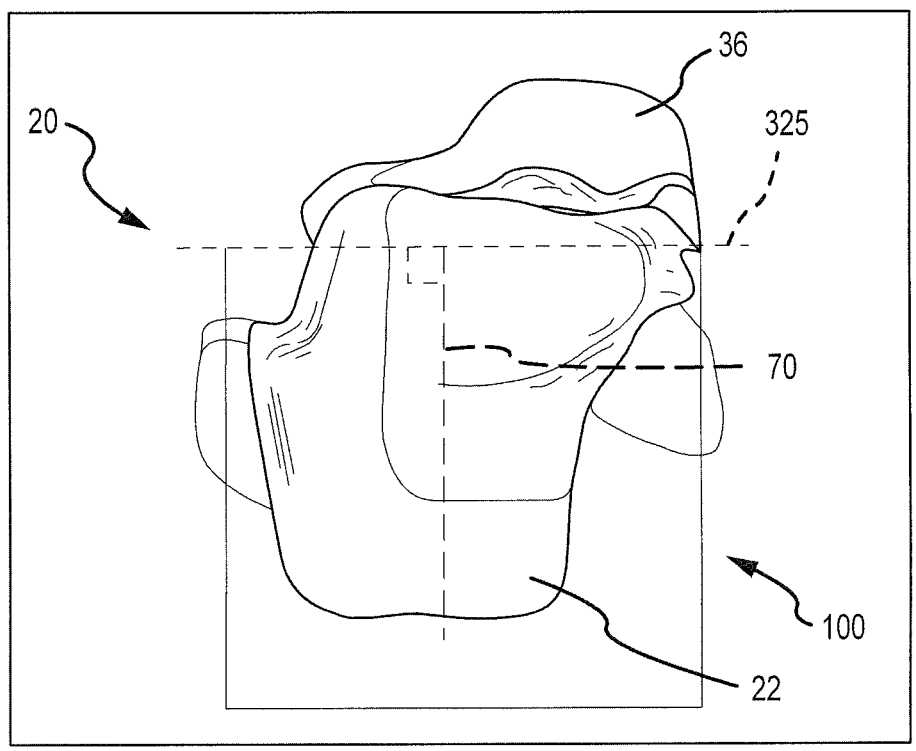
FIG. 30 is a sagittal view of the 3D tibial superimposed model with the flexion/extension orientation depicted.

As can be understood from FIG. 29, which is a sagittal view of the femoral bone model 22, the femoral resection plane 320 is caused to be orthogonal to the femoral mechanical axis 68 in the sagittal view. Similarly, as can be understood from FIG. 30, which is a sagittal view of the tibial superimposed model 100, the tibial resection plane 325 is caused to be orthogonal to the tibial mechanical axis 70 in the sagittal view. The flexion/extension orientations for both the femur 18 and tibia 20 have now been established for the POP. Variations to flexion/extension orientation can be made via the implant sizing operations as described below.

Figure 31:
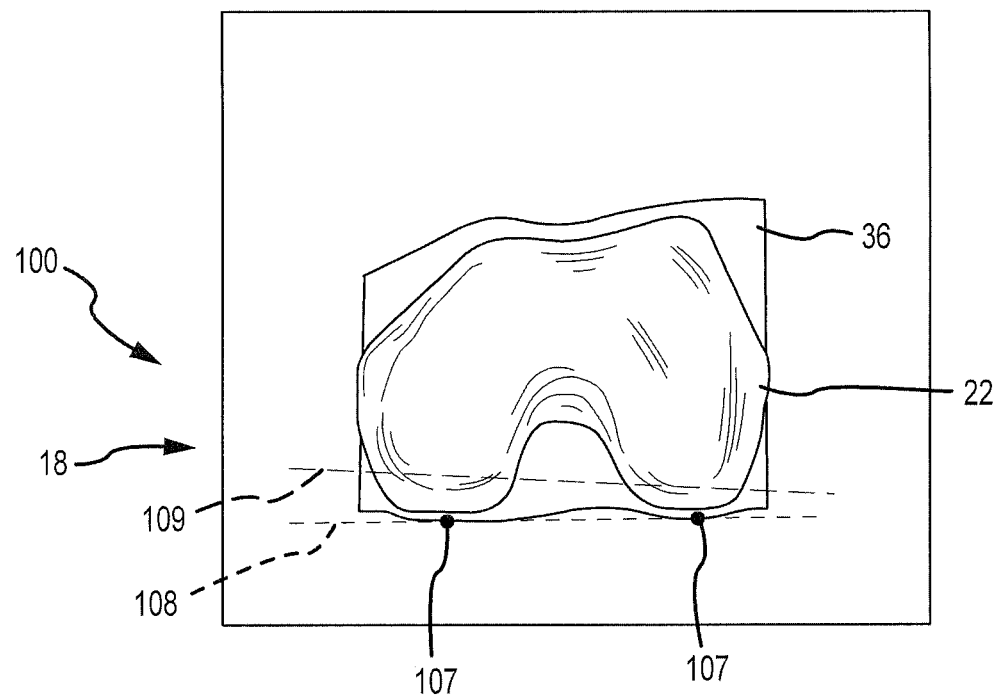
FIG. 31 is an axial or transverse view of the 3D femoral bone model with the external/internal orientation depicted.

As indicated in FIG. 31, which is the same axial view of the femur superimposed model 100 as shown in FIG. 24, an external rotation of approximately three degrees (plus or minus a degree or so, depending on the implant intended to be implanted is provided, as can be understood from the angular difference between lines 108 and 109. Specifically, the implant is rotated externally the desired amount from the previously identified posterior condylar line 108 about the center of the implant. The internal/external rotational orientation for the femur 18 has now been established for the POP.

As can be understood from FIG. 26, external rotation can be visualized off of the medial one third of the tibial tubercle identified by point 112. Specifically, from the previously identified tibial rotational reference (i.e., the medial one third of the tibial tubercle indicated by point 112), the tibial implant is aligned with the rotational reference. The internal/external rotational orientation for the tibia 20 has now been established for the POP.

Figure 1M:
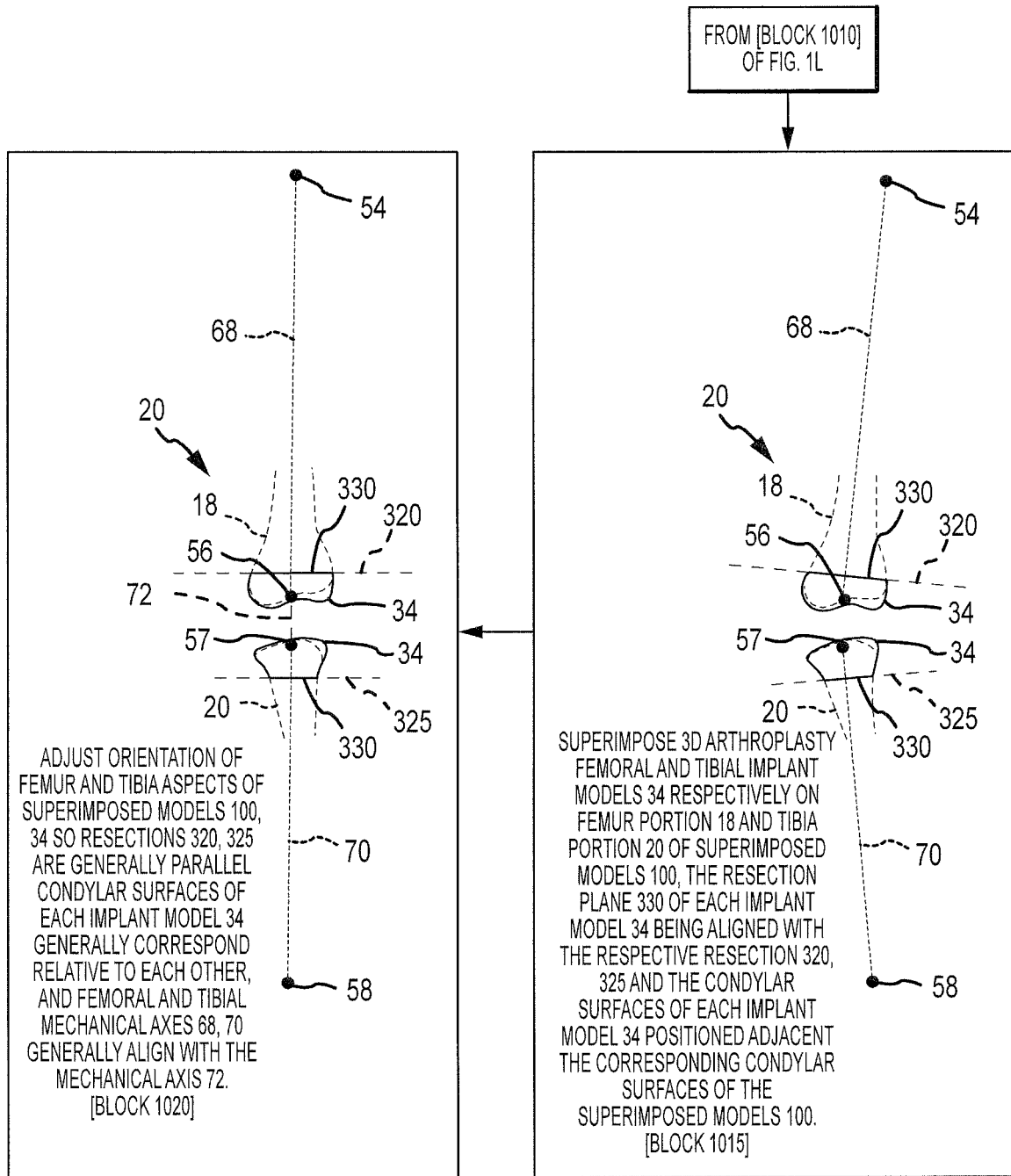

As shown in FIG. 1M, 3D arthroplasty femoral and tibial implant models 34 are respectively superimposed on the femur portion 18 and tibia portion 20 of the superimposed models 100 [Block 1015]. In doing so, the resection plane 330 of each implant model 34 is aligned with the respective resection line 320, 325 and orthogonal to the respective mechanical axis 68, 70. Since the depth of resection DR is based off of the dimension of the candidate implant, the condylar surfaces of each implant model 34 end up being positioned adjacent the corresponding condylar surfaces of the superimposed models 100 [Block 1015].

Figure 32:
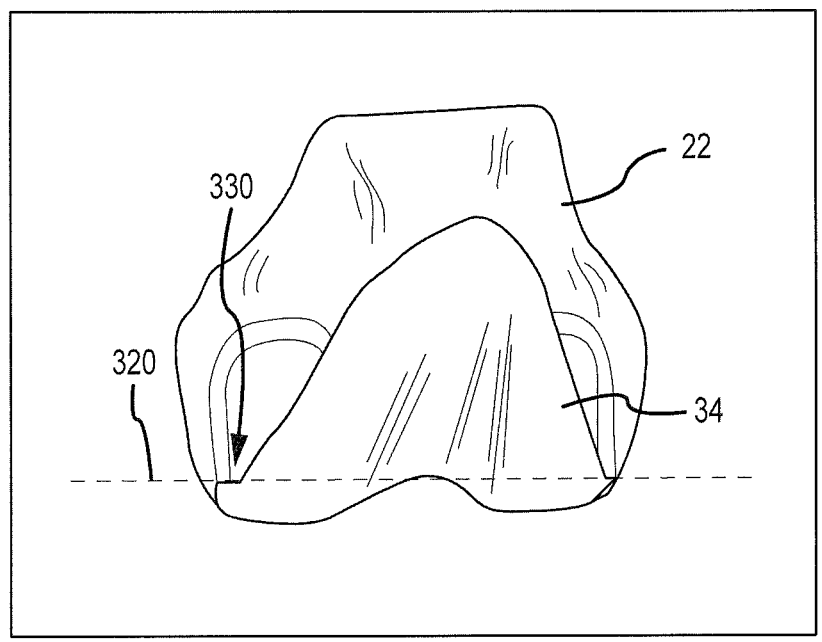
FIG. 32 is a coronal view of the 3D femoral bone model superimposed with a 3D femoral implant model with the superior/inferior translation depicted.
Figure 33:
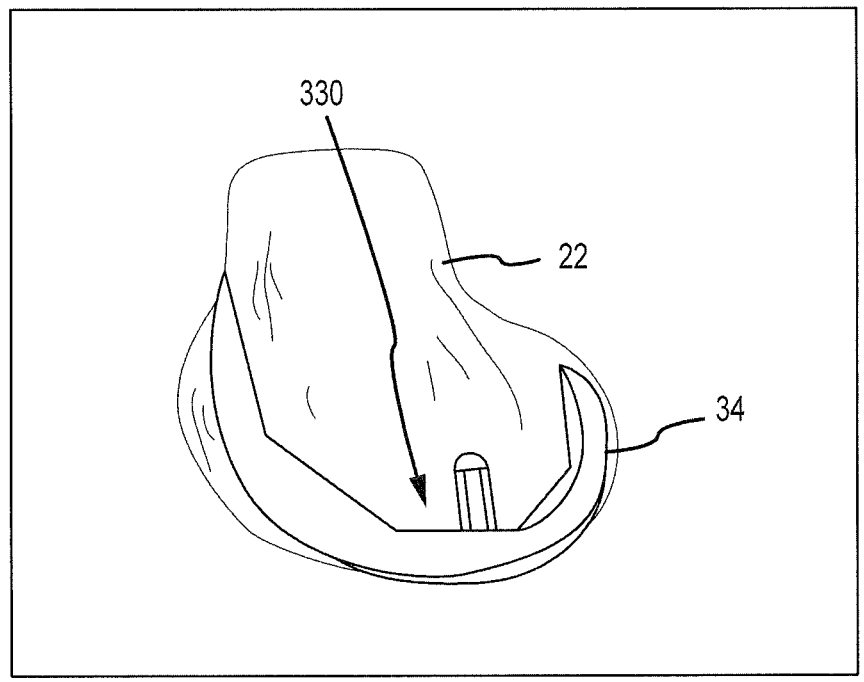
FIG. 33 is a sagittal view of the 3D femoral bone model superimposed with a 3D femoral implant model with the anterior/posterior translation depicted and flexion/extension depicted.

For example, as shown in FIGS. 32 and 33, which are, respectively, coronal and sagittal views of the femoral bone model 22 of the superimposed model 100, in one embodiment, the resection plane 330 of the femoral implant model 34 includes the resection line 320, the femoral implant resection plane 330 being orthogonal to the femoral mechanical axis 68. Also, the resection line 320 via the above-described operation of Block 1010 of FIG. 1L is located such that the condylar surfaces of the femoral implant model 34 are adjacent the condylar surfaces of the femoral bone model 22 and, in some cases, essentially coextensive with each other over portions of the condylar surfaces.

Figure 34:
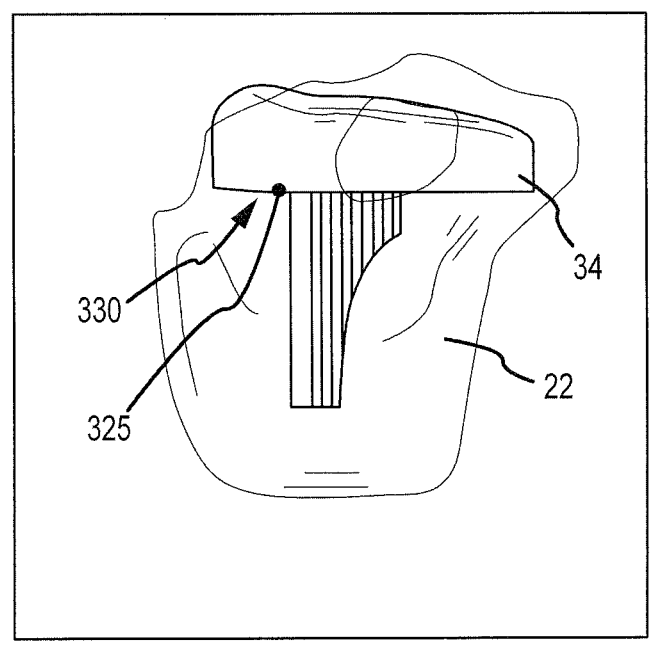
FIG. 34 is a sagittal view of the 3D tibial bone model superimposed with a 3D tibial implant model with the superior/inferior translation depicted and flexion/extension (i.e., tibial slope depicted).

Similarly, as can be understood from FIG. 34, which is a sagittal view of the tibial bone model 22 of the superimposed model 100, in one embodiment, the resection plane 330 of the tibial implant model 34 includes the resection line 325 (shown as a point), the tibial implant resection plane 330 being orthogonal to the tibial mechanical axis 70. Also, the resection line 325 via the above-described operation of Block 1010 of FIG. 1L is located such that the condylar surfaces of the tibial implant model 34 are adjacent the condylar surfaces of the tibial bone model. 22 and, in some cases, essentially coextensive with each other over portions of the condylar surfaces.

Figure 35:
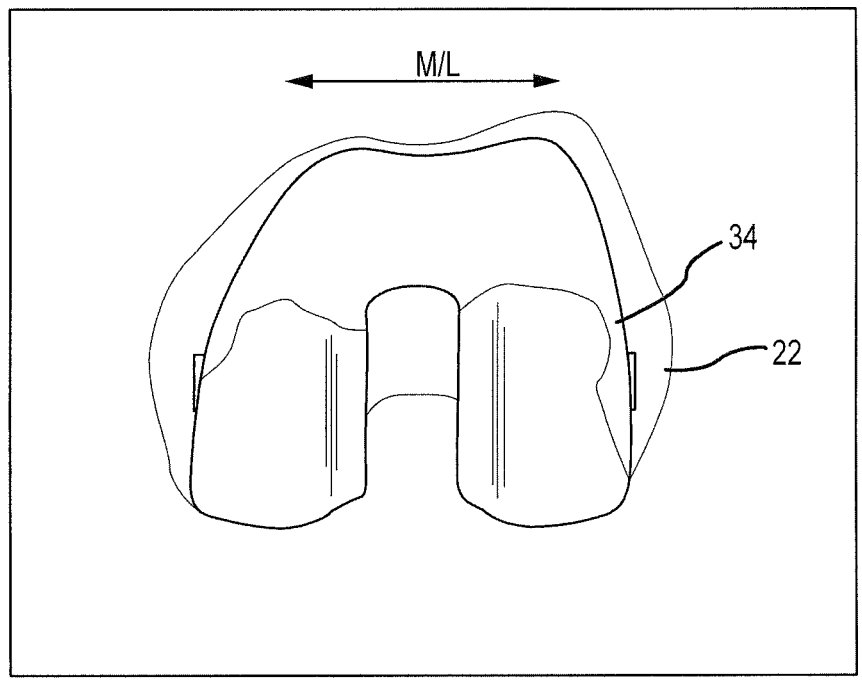
FIG. 35 is an axial or transverse view of the 3D femoral bone model superimposed with a 3D femoral implant model with the medial/lateral translation depicted.
Figure 36:
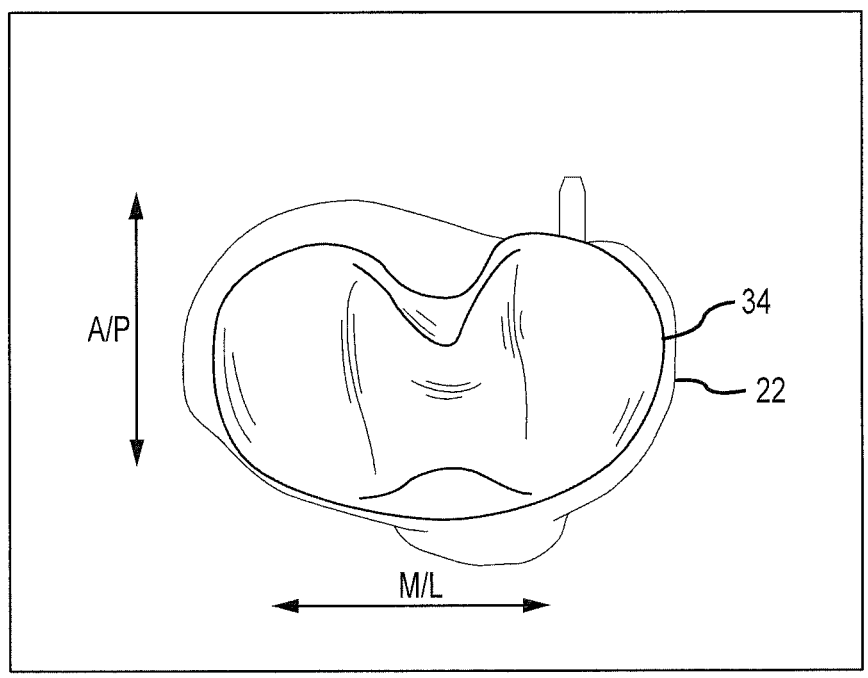
FIG. 36 is an axial or transverse view of the 3D tibial bone model superimposed with a 3D tibial implant model with the medial/lateral and anterior/posterior translations depicted.

As can be understood from FIG. 35, which is an axial view of the femoral implant model 34 superimposed on the femoral bone model 22, the femoral implant model 34 is centered medial-lateral relative to the femoral bone model 22 to have symmetric medial-lateral overhang, thereby completing the medial-lateral translation of the implant model. Similarly, as can be understood from FIG. 36, which is an axial view of the tibial implant model 34 superimposed on the tibial bone model 22, the tibial implant model 34 is centered medial-lateral and anterior-posterior relative to the tibial bone model 22 to have equal bone exposed circumferentially, the size of the tibial implant model 34 being adjusted as necessary, thereby completing the medial-lateral translation and the anterior-posterior translation of the implant model.

Femoral implant model sizing may be completed by first sizing the femoral implant model 34 in the sagittal view so as to fit the distal condyles and anterior cortex of the femoral bone model 22. Inspections for fit are made in the coronal and axial views. The best implant size is determined based on the distance from the posterior condylar line to the anterior cortex. If notching of the femoral shaft is present, the femoral implant model 34 flexed up to a maximum of approximately five degrees and reassessed for notching. If notching is still present, then the femoral implant model 34 is upsized and returned to a neutral alignment. If notching is again present, then the femoral implant model 34 is flexed up to a maximum of approximately five degrees and the medial-lateral overhang is assessed and a size for the femoral implant model is selected.

As can be understood from FIG. 33, the posterior position of the femoral implant model 34 is maintained relative to the femoral bone model 22 while the anterior-posterior position is modified by increasing or decreasing the size of the femoral implant model 34. This completes the anterior-posterior translation of the femoral implant model.

As can be understood from FIG. 1M, in one embodiment, the orientation of femur and tibia aspects of superimposed models 100, 34 are adjusted so resections 320, 325 are generally parallel, the condylar surfaces of each implant model 34 generally correspond relative to each other, and the femoral and tibial mechanical axes 68, 70 generally align with the mechanical axis 72 [Block 1020]. Similar to described above with respect to Block 195 of FIG. 1H, the various models and axes depicted as described in Block 1020 may be sent to the physician as a coronal view snapshot for review. In a manner similar to that described above with respect to FIG. 1I, the physician may review the provided coronal view snapshot and accept the POP as depicted therein or propose modifications to the POP. Once the POP is approved by the physician, the POP is employed as saw cut and drill hole data 44 [Block 240 of FIG. 1K] and then combined with the jig data 46 to form integrated jig data 48 [Block 270 of FIG. 1K], the manufacture of the jigs 2A, 2B then preceding as described in Blocks 275-285 of FIG. 1K.

The discussion provided herein is given in the context of TKR and TKR jigs and the generation thereof. However, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

Although the present invention has been described with reference to preferred embodiments, persons skilled in the art will recognize that changes may be made in form and detail without departing from the spirit and scope of the invention.

We claim:

1. A method of preoperatively planning an arthroplasty on a patient, the method comprising:
    obtaining at least one first image of a knee region of the patient;
    obtaining at least one second image of a leg region of the patient including a hip region, the knee region, and an ankle region, the at least one first image and the at least one second image resulting from separate imaging events;
    determining a hip center and an ankle center from the at least one second image;
    determining at least one mechanical axis of the leg region based on the hip center and the ankle center from the at least one second image;
    generating a bone model of the knee region of the patient using the at least one first image and the at least one mechanical axis; and
    preparing a preoperative surgical plan based on the bone model of the knee region of the patient.

2. The method of claim 1, further comprising merging the at least one first image and the at least one second image by positionally matching in a computerized coordinate system first anatomical landmarks in the at least one first image and second anatomical landmarks in the at least one second image.

3. The method of claim 1, wherein the bone model comprises a femoral bone model, and a tibial bone model, the at least one mechanical axis comprises a femoral mechanical axis associated with the femoral bone model, and a tibial mechanical axis associated with the tibial bone model.

4. The method of claim 3, wherein the femoral bone model and the femoral mechanical axis, and tibial bone model and the tibial mechanical axis are positioned relative to each other in a computerized coordinate system with the location and orientation of the femoral mechanical axis and the tibial mechanical axis as determined from the at least one second image.

5. The method of claim 3, wherein preparing the preoperative surgical plan comprises determining, in a computerized coordinate system, a femoral arthroplasty resection relative to anatomical information associated with the femoral bone model, and a tibial arthroplasty resection relative to anatomical information associated with the tibial bone model.

6. The method of claim 5, wherein determining the femoral arthroplasty resection comprises superimposing femoral implant data over the femoral bone model.

7. The method of claim 6, wherein the femoral implant data comprises at least one of a femoral implant model or resection planes associated with the femoral implant model.

8. The method of claim 5, wherein determining the tibial arthroplasty resection comprises superimposing tibial implant data over the tibial bone model.

9. The method of claim 8, wherein the tibial implant data comprises at least one of a tibial implant model or resection planes associated with the tibial implant model.

10. The method of claim 1, wherein the at least one second image is a coronal image.

11. The method of claim 1, wherein the at least one first image and the at least one second image are of the same imaging modality.

12. The method of claim 11, wherein the imaging modality is MRI.

13. The method of claim 1, wherein the at least one first image excludes the hip region and the ankle region.

14. A method of preoperatively planning an arthroplasty on a patient, the method comprising:
- obtaining at least one first image of a knee region of the patient;
- obtaining at least one second image of a leg region of the patient including a hip region, the knee region, and an ankle region, the at least one first image and the at least one second image resulting from separate imaging events;
- determining, within a first coordinate system, coordinate locations for a hip center and an ankle center from the at least one second image;
- determining, within a first coordinate system, at least one mechanical axis of the leg region based on the hip center and the ankle center from the at least one second image;
- generating, within a second coordinate system, a bone model of the knee region of the patient using the at least one first image;
- merging the at least one mechanical axis of the leg region from the first coordinate system and the bone model of the knee region from the second coordinate system into a common coordinate system; and
- preparing a preoperative surgical plan based on the bone model of the knee region of the patient.

15. The method of claim 14, wherein the at least one first image of the knee region includes a depiction of soft tissue and bone.

16. The method of claim 14, wherein the at least one first image and the at least one second image are both magnetic resonance images.

17. The method of claim 14, wherein the at least one first image excludes the hip region and the ankle region.

18. The method of claim 14, wherein the bone model comprises a femoral bone model, and a tibial bone model, the at least one mechanical axis comprises a femoral mechanical axis associated with the femoral bone model, and a tibial mechanical axis associated with the tibial bone model.

19. The method of claim 18, wherein preparing the preoperative surgical plan comprises determining, in the common coordinate system, a femoral arthroplasty resection relative to anatomical information associated with the femoral bone model, and a tibial arthroplasty resection relative to anatomical information associated with the tibial bone model.

20. The method of claim 14, further comprising displaying the at least one mechanical axis on the bone model of the knee region.

* * * * *